US008663602B2

(12) United States Patent
Hellerstein

(10) Patent No.: US 8,663,602 B2
(45) Date of Patent: *Mar. 4, 2014

(54) METHOD FOR HIGH-THROUGHPUT SCREENING OF COMPOUNDS AND COMBINATIONS OF COMPOUNDS FOR DISCOVERY AND QUANTIFICATION OF ACTIONS, PARTICULARLY UNANTICIPATED THERAPEUTIC OR TOXIC ACTIONS, IN BIOLOGICAL SYSTEMS

(75) Inventor: Marc K. Hellerstein, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/031,084

(22) Filed: Feb. 18, 2011

(65) Prior Publication Data

US 2011/0195865 A1 Aug. 11, 2011

Related U.S. Application Data

(63) Continuation of application No. 10/997,323, filed on Nov. 23, 2004, now abandoned.

(60) Provisional application No. 60/525,261, filed on Nov. 25, 2003.

(51) Int. Cl.
*A61K 49/00* (2006.01)

(52) U.S. Cl.
USPC ......... 424/9.2; 424/1.11; 424/1.65; 424/1.81; 424/9.1

(58) Field of Classification Search
USPC ........... 424/1.11, 1.49, 1.65, 1.69, 1.73, 1.81, 424/1.85, 1.89, 9.1, 9.2; 702/19; 514/1, 1.1
See application file for complete search history.

(56) References Cited

U.S. PATENT DOCUMENTS

| | | |
|---|---|---|
| 4,065,552 A | 12/1977 | Costa |
| 4,332,784 A | 6/1982 | Smith et al. |
| 4,889,126 A | 12/1989 | Doddrell et al. |
| 4,940,658 A | 7/1990 | Allen et al. |
| 5,026,909 A | 6/1991 | Zolotarev et al. |
| 5,042,488 A | 8/1991 | Ackerman |
| 5,167,948 A | 12/1992 | Wenzel |
| 5,209,919 A | 5/1993 | Turteltaub et al. |
| 5,317,098 A | 5/1994 | Shizuya et al. |
| 5,338,686 A | 8/1994 | Hellerstein |
| 5,354,662 A | 10/1994 | Stone et al. |
| 5,376,355 A | 12/1994 | Turteltaub et al. |
| 5,394,236 A | 2/1995 | Murnick |
| 5,432,058 A | 7/1995 | Lange, III et al. |
| 5,439,803 A | 8/1995 | Ross et al. |
| 5,506,147 A | 4/1996 | Kolhouse et al. |
| 5,597,548 A | 1/1997 | Sherry et al. |
| 5,665,377 A | 9/1997 | Gonella |
| 5,665,562 A | 9/1997 | Cook |
| 5,783,445 A | 7/1998 | Murnick |
| 5,855,921 A | 1/1999 | Somlyai |
| 5,910,403 A | 6/1999 | Hellerstein |
| 5,916,537 A | 6/1999 | Kajiwara et al. |
| 5,922,554 A | 7/1999 | Fielding et al. |
| 5,924,995 A | 7/1999 | Klein et al. |
| 5,961,470 A | 10/1999 | Wagner et al. |
| 6,010,846 A | 1/2000 | Hellerstein |
| 6,031,228 A | 2/2000 | Abramson |
| 6,071,245 A | 6/2000 | Kohno et al. |
| 6,117,656 A | 9/2000 | Seed |
| 6,284,219 B1 | 9/2001 | Ajami |
| 6,329,208 B1 | 12/2001 | Jones et al. |
| 6,355,416 B1 | 3/2002 | Abramson |
| 6,461,806 B1 | 10/2002 | Hellerstein |
| 6,461,870 B2 | 10/2002 | Yatscoff et al. |
| 6,468,802 B1 | 10/2002 | Yatscoff et al. |
| 6,599,750 B2 | 7/2003 | Yatscoff et al. |
| 6,602,715 B2 | 8/2003 | Yatscoff et al. |
| 6,610,270 B1 | 8/2003 | Ajami |

(Continued)

FOREIGN PATENT DOCUMENTS

| | | |
|---|---|---|
| CA | 2494715 A1 | 2/2004 |
| EP | 0826377 B1 | 11/2002 |

(Continued)

OTHER PUBLICATIONS

Landau et al., "Use of 2H2O for Estimating Rates of Gluconeogenesis", Journal of Clinical Investigation, vol. 95, Jan. 1995, pp. 172-178.
Office Action received for Australian Patent Application No. 2004293106, mailed on Jul. 28, 2010, 3 Pages.
Extended European Search Report received for European Patent Application No. 06784805.1, mailed on Mar. 21, 2011, 7 Pages.
Extended European Search Report received for European Patent Application No. 06759050.5, mailed on Mar. 31, 2011, 7 Pages.
Office Action received for Japanese Patent Application No. 2006-541461, mailed on May 31, 2011, 6 pages (2 pages of English translation and 4 pages of Office Action).

(Continued)

*Primary Examiner* — D L Jones
(74) *Attorney, Agent, or Firm* — Morrison & Foerster LLP

(57) ABSTRACT

The invention enables high-throughput screening of compounds in living systems to detect unanticipated or unintended biological actions. The invention also allows for screening, detection, and confirmation of new indications for approved drugs. Screening and detection of toxic effects of compounds also can be achieved by using the methods of the invention. The methods comprise administering isotope-labeled substrates to a living system so that the label is incorporated into molecules in a manner that reveals flux rates through metabolic pathways thought to be involved in a disease. Comparisons between living systems exposed to compounds and living systems not so exposed reveals the effects of the compounds on the flux rates through the metabolic pathways. Combinations or mixtures of compounds can be systematically screened to detect unanticipated or unintended biological actions, including synergistic actions, in the same manner.

14 Claims, 8 Drawing Sheets

(56) References Cited

U.S. PATENT DOCUMENTS

| | | |
|---|---|---|
| 6,625,547 B1 | 9/2003 | Korzekwa et al. |
| 6,642,059 B2 | 11/2003 | Chait et al. |
| 6,653,076 B1 | 11/2003 | Franza, Jr. et al. |
| 6,653,090 B1 | 11/2003 | Lopaschuk |
| 6,670,194 B1 | 12/2003 | Aebersold et al. |
| 6,680,203 B2 | 1/2004 | Dasseux et al. |
| 6,764,817 B1 | 7/2004 | Schneider |
| 6,783,751 B2 | 8/2004 | Heumann |
| 6,808,875 B2 * | 10/2004 | Hellerstein ............ 435/4 |
| 6,835,927 B2 | 12/2004 | Becker et al. |
| 6,849,396 B2 | 2/2005 | Schneider |
| 6,872,575 B2 | 3/2005 | Regnier |
| 6,887,712 B1 | 5/2005 | Medford et al. |
| 6,902,719 B2 | 6/2005 | Wagner |
| 6,906,320 B2 | 6/2005 | Sachs et al. |
| 7,001,587 B2 * | 2/2006 | Hellerstein ............ 424/9.1 |
| 7,022,834 B2 | 4/2006 | Hellerstein |
| 7,048,907 B2 | 5/2006 | Groman et al. |
| 7,057,168 B2 | 6/2006 | Miller et al. |
| 7,084,396 B2 | 8/2006 | Schneider |
| 7,255,850 B2 * | 8/2007 | Hellerstein ............ 424/1.37 |
| 7,256,047 B2 | 8/2007 | Malloy et al. |
| 7,262,020 B2 * | 8/2007 | Hellerstein ............ 435/29 |
| 7,307,059 B2 | 12/2007 | Hellerstein |
| 7,357,913 B2 * | 4/2008 | Hellerstein ............ 424/1.11 |
| 7,410,633 B2 * | 8/2008 | Hellerstein ............ 424/9.1 |
| 7,449,171 B2 * | 11/2008 | Hellerstein ............ 424/9.1 |
| 7,504,233 B2 | 3/2009 | Hellerstein |
| 7,910,323 B2 | 3/2011 | Hellerstein |
| 8,005,623 B2 * | 8/2011 | Hellerstein ............ 702/19 |
| 8,021,644 B2 | 9/2011 | Hellerstein |
| 8,084,016 B2 * | 12/2011 | Hellerstein ............ 424/9.1 |
| 8,129,335 B2 * | 3/2012 | Hellerstein ............ 514/1.1 |
| 8,401,800 B2 * | 3/2013 | Hellerstein ............ 702/19 |
| 2003/0068634 A1 | 4/2003 | Hellerstein |
| 2003/0119069 A1 | 6/2003 | Schneider et al. |
| 2003/0133871 A1 | 7/2003 | Hellerstein |
| 2003/0148533 A1 | 8/2003 | Malloy et al. |
| 2003/0180710 A1 | 9/2003 | Lee et al. |
| 2003/0180800 A1 * | 9/2003 | Lee et al. ............ 435/7.1 |
| 2003/0211036 A1 | 11/2003 | Degani et al. |
| 2003/0224420 A1 | 12/2003 | Hellerstein et al. |
| 2003/0228259 A1 | 12/2003 | Hellerstein |
| 2004/0081994 A1 | 4/2004 | Hellerstein |
| 2004/0091943 A1 | 5/2004 | Schneider |
| 2004/0115131 A1 | 6/2004 | Hellerstein |
| 2004/0121305 A1 | 6/2004 | Wiegand et al. |
| 2004/0152994 A1 | 8/2004 | Meier-Augenstein |
| 2004/0191916 A1 | 9/2004 | Gross et al. |
| 2004/0253647 A1 | 12/2004 | Mathews et al. |
| 2005/0003375 A1 | 1/2005 | Franza, Jr. et al. |
| 2005/0014181 A1 | 1/2005 | Galis et al. |
| 2005/0092910 A1 | 5/2005 | Geromanos et al. |
| 2005/0118724 A1 | 6/2005 | Bateman et al. |
| 2005/0153346 A1 | 7/2005 | Schneider |
| 2005/0175982 A1 | 8/2005 | Iwatani et al. |
| 2005/0180949 A1 | 8/2005 | Emtage et al. |
| 2005/0201937 A1 | 9/2005 | Hellerstein |
| 2005/0202406 A1 | 9/2005 | Hellerstein |
| 2005/0221278 A1 | 10/2005 | Iwatani et al. |
| 2005/0238577 A1 | 10/2005 | Hellerstein |
| 2005/0238581 A1 | 10/2005 | Kurland et al. |
| 2005/0255509 A1 | 11/2005 | Hellerstein et al. |
| 2005/0281745 A1 | 12/2005 | Lee et al. |
| 2006/0008796 A1 | 1/2006 | Hellerstein |
| 2006/0029549 A1 | 2/2006 | Hellerstein |
| 2006/0094057 A1 | 5/2006 | Hellerstein |
| 2006/0100903 A1 | 5/2006 | Lee et al. |
| 2006/0105322 A1 | 5/2006 | Iwatani et al. |
| 2006/0105339 A1 | 5/2006 | Hellerstein |
| 2006/0120961 A1 | 6/2006 | Schneider et al. |
| 2006/0204439 A1 | 9/2006 | Hellerstein |
| 2006/0251576 A1 | 11/2006 | Hellerstein |
| 2006/0280682 A1 | 12/2006 | Hellerstein |
| 2007/0248540 A1 | 10/2007 | Hellerstein |
| 2008/0003179 A1 | 1/2008 | Hellerstein |
| 2009/0041661 A1 | 2/2009 | Hellerstein |

FOREIGN PATENT DOCUMENTS

| | | |
|---|---|---|
| JP | 2001-211782 A | 8/2001 |
| JP | 2003-502016 A | 1/2003 |
| JP | 2003-79270 A | 3/2003 |
| SU | 968036 A1 | 10/1982 |
| WO | 90/11371 A1 | 10/1990 |
| WO | 93/20800 A1 | 10/1993 |
| WO | 93/25705 A1 | 12/1993 |
| WO | 95/13096 A1 | 5/1995 |
| WO | 98/51820 A1 | 11/1998 |
| WO | 00/12535 A2 | 3/2000 |
| WO | 00/13025 A1 | 3/2000 |
| WO | 00/55355 A2 | 9/2000 |
| WO | 00/63683 A1 | 10/2000 |
| WO | 01/80715 A2 | 11/2001 |
| WO | 01/84143 A1 | 11/2001 |
| WO | 03/061479 A1 | 7/2003 |
| WO | 03/068919 A2 | 8/2003 |
| WO | 03/087314 A2 | 10/2003 |
| WO | 2004/003493 A2 | 1/2004 |
| WO | 2004/011426 A2 | 2/2004 |
| WO | 2004/016156 A2 | 2/2004 |
| WO | 2004/021863 A2 | 3/2004 |
| WO | 2004/024941 A2 | 3/2004 |
| WO | 2004/025270 A2 | 3/2004 |
| WO | 2004/042360 A2 | 5/2004 |
| WO | 2004/016156 A3 | 6/2004 |
| WO | 2005/009597 A2 | 2/2005 |
| WO | 2005/015155 A2 | 2/2005 |
| WO | 2005/033652 A2 | 4/2005 |
| WO | 2006/050130 A2 | 5/2006 |
| WO | 2006/081521 A2 | 8/2006 |
| WO | 2006/107814 A2 | 10/2006 |

OTHER PUBLICATIONS

International Search Report and Written Opinion received for PCT Patent Application No. PCT/US2006/022915, mailed on Aug. 8, 2007, 5 pages.

Aydemir et al., "Effects of Defibrotide on Aorta and Brain Malondialdehyde and Antioxidants in Cholesterol-Induced Atherosclerotic Rabbits", International Journal of Clincal & Laboratory Research, vol. 30, 2000, pp. 101-107.

Bantscheff et al., "Quantitative Mass Spectrometry In Proteomics: A Critical Review", Anal. Bioanal. Chem., vol. 389, 2007, pp. 1017-1031.

Buchanan, T.A., "Pancreatic Beta-Cell Loss and Preservation in Type 2 Diabetes", Clinical Therapeutics, vol. 25, 2003, pp. B32-B46.

Chobanian et al., "Body Cholesterol Metabolism in Man. II. Measurement of the Body Cholesterol Miscible Pool and Turnover Rate", Journal of Clinical Investigation, vol. 41, No. 9, 1962, pp. 1738-1744.

Duane, William C., "Measurement of Bile Acid Synthesis by Three Different Methods in Hypertriglyceridemic And Control Subjects", Journal of Lipid Research, vol. 38, 1997, pp. 183-188.

Edes et al., "Glycemic Index and Insulin Response to a Liquid Nutritional Formula Compared with a Standard Meal", Journal of the American College of Nutrition, vol. 17, No. 1, 1998, pp. 30-35.

Ferezou et al., "Origins of Neutral Sterols in Human Feces Studied by Stable Isotope Labeling (Deuterium and Carbon-13) Existence of an External Secretion of Cholesterol", Digestion, vol. 21, No. 5, 1981, pp. 232-243.

Futami et al., "An Application of the On-line Respiratory Mass Spectrometer to the Detection of *Helicobacter pylori* Infection Using 13C-Labeled Urea", Journal of the Mass Spectrometry Society of Japan, vol. 47, No. 6, 1999, pp. 386-388.

Jones et al., "Modulation of Plasma Lipid Levels and Cholesterol Kinetics by Phytosterol Versus Phytostanol Esters", Journal of Lipid Research, vol. 41, 2000, pp. 697-705.

Murphy et al., "A New, Sensitive in Vivo Diagnostic Test of Insulin Resistance: The Deuterated Oral Glucose Tolerance Test (2H-OGTT)", Diabetes, American Diabetes Association, U.S., vol. 53, No. SUPPL. 02, Jan. 1, 2004, 2 pages.

(56) References Cited

OTHER PUBLICATIONS

Radziuk, J., "Insulin Sensitivity and its Measurement: Structural Commonalities among the Methods", The Journal of Endocrinology & Metabolism, vol. 85, No. 12, 2000, pp. 4426-4433.

Sakurai, Y., "The Meanings of Measuring Biological Metabolism Using a Stable Isotope Labeled Tracer: The Difference in Metabolism Between a Healthy Human and a Patient in Surgically Serious Condition", Medical Journal of Fukita Academy, vol. 20, No. 1, 1996, pp. 9-21.

Schoenheimer et al., "Deuterium as an Indicator in the Study of Intermediary Metabolism—III. The Role of the Fat Tissues", The Journal of Biological Chemistry, vol. 111, 1935, pp. 175-181.

Schoenheimer et al., "Deuterium as an Indicator in the Study of Intermediary Metabolism—IX. The Conversion of Stearic Acid into Palmitic Acid in the Organism", The Journal of Biological Chemistry, vol. 120, 1937, pp. 155-165.

Shen et al., "Purification of Oligodendrocyte and its Myelination to the Demyelinated Culture Model in Vitro", Acta Histochem. Cytochem, vol. 35, No. 2, 2002, p. 123.

Tayek et al., "Glucose Production, Recycling, and Gluconeogenesis in Normals and Diabetics: A Mass Isotopomer [U-13C] Glucose Study", American Journal of Physiology—Endocrinology and Metabolism, vol. 270, No. 4, Apr. 1, 1996, pp. E709-E717.

Wang et al., "Validation of a Single-Isotope-Labeled Cholesterol Tracer Approach for Measuring Human Cholesterol Absorption", Lipids, vol. 39, No. 1, 2004, pp. 87-91.

Australian Patent Office Search Report mailed on Aug. 26, 2005, for Singapore Patent Application No. 200500571-5, filed on Jul. 25, 2003, 5 pages.

Written Opinion mailed on Jul. 14, 2006, by the Australian Patent Office for Singapore Patent Application No. 200502593-7, filed Nov. 4, 2003, 5 pages.

Australian Search Report and Written Opinion mailed on Aug. 5, 2009, for Singapore Patent Application No. 200717391-7, filed on May 3, 2006, 7 pages.

Supplementary Partial European Search Report received for European Patent Application No. 03749756.7, mailed on Aug. 17, 2005, 6 pages.

Supplementary Partial European Search Report received for European Patent Application No. 03713429.3, mailed on Mar. 9, 2006, 6 pages.

Supplementary Partial European Search Report received for European Patent Application No. 02806603.3, mailed on Jul. 25, 2008, 5 pages.

Supplementary Partial European Search Report received for European Patent Application No. 03768624.3, mailed on Sep. 22, 2006, 4 pages.

Supplementary European Search Report received for European Patent Application No. 05733311.4, mailed on Sep. 19, 2008, 9 pages.

Supplementary European Search Report received for European Patent Application No. 05725448.4, mailed on Jun. 30, 2009, 7 pages.

Supplementary European Search Report received for European Patent Application No. 04809469.2, mailed on Jul. 28, 2009, 4 pages.

Office Action received for European Patent Application No. 04812281.6, mailed on Jan. 18, 2011, 6 pages.

International Search Report received for PCT Patent Application No. PCT/US2003/04183, mailed on Jun. 29, 2004, 4 pages.

International Search Report received for PCT Patent Application No. PCT/US2003/10554, mailed on Aug. 20, 2004, 4 pages.

International Search Report received for PCT Patent Application No. PCT/US2003/20052, mailed on Apr. 13, 2004, 3 pages.

International Search Report received for PCT Patent Application No. PCT/US2003/23340, mailed on Aug. 18, 2004, 4 pages.

International Search Report received for PCT Patent Application No. PCT/US2003/27623, mailed on Jul. 8, 2004, 4 pages.

International Search Report received for PCT Patent Application No. PCT/US2003/29361, mailed on Jan. 19, 2005, 4 pages.

International Search Report received for PCT Patent Application No. PCT/US2003/29526, mailed on Aug. 18, 2004, 3 pages.

International Search Report received for PCT Patent Application No. PCT/US2003/35107, mailed on Jul. 9, 2004, 2 pages.

International Search Report received for PCT Patent Application No. PCT/US2004/21063, mailed on Apr. 4, 2005, 2 pages.

International Search Report received for PCT Patent Application No. PCT/US2004/39722, mailed on Mar. 25, 2005, 3 pages.

International Search Report and Written Opinion received for PCT Patent Application No. PCT/US2005/05660, mailed on Oct. 11, 2007, 11 pages.

International Search Report and Written Opinion received for PCT Patent Application No. PCT/US2005/10429, mailed on Aug. 8, 2006, 15 pages.

International Search Report received for PCT Patent Application No. PCT/US2005/08265, mailed on Aug. 1, 2005, 4 pages.

International Search Report and Written Opinion received for PCT Patent Application No. PCT/US2006/017167, mailed on Feb. 5, 2008, 11 pages.

"NCBI Blast: Protein Sequence (17 letters).", Available at: <http://blast.ncbi.nlm.nih.gov/Blast.cgi> visited on May 29, 2008, 5 pages.

"New Diagnostic Technique Could Help Treat AIDS", Agence France-Presse, Dow Jones News. Feb. 17, 1998, pp. 1-2.

Abou-Donia et al., "Mechanisms of Joint Neurotoxicity of n-Hexane, Methyl Isobutyl Ketone and O-Ethyl 0-4-Nitrophenyl Phenylphosphonothioate in Hens", The Journal of Pharmacology and Experimental Therapeutics, vol. 257, No. 1, 1991, pp. 282-289.

Abu-Qare et al., "Quantification of Nicotine, Chlorpyrifos and Their Metabolites in Rat Plasma and Urine Using High-Performance Liquid Chromatography", Journal of Chromatography B., vol. 757, 2001, pp. 295-300.

Ackermans et al., "The Quantification of Gluconeogenesis in Healthy Men by 2H2O and [2-13C]Glycerol Yields Different Results: Rates of Gluconeogenesis in Healthy Men Measured with H2HO are Higher than those Measured with [2-13C]Glycerol", The Journal of Clinical Endocrinology & Metabolism, vol. 86, No. 5, 2001, pp. 2220-2226.

Adami et al., "The Aetiology and Pathogenesis of Human Breast Cancer", Mutation Research, vol. 333, 1995, pp. 29-35.

Airhart et al., "Compartmentation of Free Amino Acids for Protein Synthesis in Rat Liver", The Biochemical Journal, vol. 140, 1974, pp. 539-545.

Ajie et al., "In Vivo Study of the Biosynthesis of Long-Chain Fatty Acids Using Deuterated Water", The American Journal of Physiology, vol. 269, 1995, pp. E247-E252.

Anderson et al., "Direct HIV Cytopaticity Cannot Account for CD4 Decline in AIDS in the Presence of Homeostasis: A Worst-Case Dynamic Analysis", Journal of Acquired Immune Deficiency Syndromes and Human Retrovirology, vol. 17, 1998, pp. 245-252.

Antelo et al., "Adipose Triglyceride (TG) Turnover and De Novo Lipogenesis (DNL) in Humans: Measurement by Long-Term 2H2O Labeling and Mass Isotopomer Distribution Analysis (MIDA)", Experimental Biology, FASEB#361.10, 2002, p. A400 (Abstract Only).

Attardi et al., "Biogenesis of Mitochondria", Annual Review of Cell Biology, vol. 4, 1988, pp. 289-333.

Bach et al., "Stem Cells: The Intestinal Stem Cell as a Paradigm", Carcinogenesis, vol. 21, No. 3, 2000, pp. 469-476.

Backhouse et al., "Effects of Haloperidol on Cell Proliferation in the Early Postnatal Rat Brain", Neuropathology and Applied Neurobiology, vol. 8, No. 2, 1982, pp. 109-116.

Bandsma et al., "Contribution of Newly Synthesized Cholesterol to Rat Plasma and Bile Determined by Mass Isotopomer Distribution Analysis: Bile-Salt Flux Promotes Secretion of Newly Synthesized Cholesterol into Bile", The Biochemical Journal, vol. 329, 1998, pp. 699-703.

Bandsma et al., "The Contribution of Newly Synthesized Cholesterol to Bile Salt Synthesis in Rats Quantified by Mass Isotopomer Distribution Analysis", Biochemica et Biophysica Acta, vol. 1483, 2000, pp. 343-351.

(56) References Cited

OTHER PUBLICATIONS

Bertani et al., "Measurement of Total Body Water (TBW) Through In Vivo Dilution of Tracer Compounds: Use of D2O and its Determination by FT Infrared Spectroscopy", Annali Di Chimica, vol. 92, 2002, pp. 135-138.
Bickenbach, "Identification and Behavior of Label-Retaining Cells in Oral Mucosa and Skin", Journal of Dental Research, vol. 60, 1981, pp. 1611-1620.
Bier, D. M., "The Use of Stable Isotopes in Metabolic Investigation", Balliere's Clinical Endocrinology and Metabolism, vol. 1, No. 4, Nov. 1987, pp. 817-836.
Bier, D. M., "Stable Isotopes in Biosciences, their Measurement and Models for Amino Acid Metabolism", European Journal of Pediatrics, vol. 156, 1997, pp. S2-S8.
Bingham, Sheila A., "The Use of 24-h Urine Samples and Energy Expenditure to Validate Dietary Assessments", The American Journal of Clinical Nutrition, vol. 59(suppl), 1994, pp. 227S-231S.
Black et al., "Labeling DNA with Stable Isotopes: Economical and Practical Considerations", BioTechniques, vol. 30, 2001, pp. 134-138, 140.
Blair et al., "Changes in Physical Fitness and All-Cause Mortality. A Perspective Study of Healthy and Unhealthy Men", JAMA, vol. 273, 1995, pp. 1093-1098.
Bonotto et al., "Study of the Distribution and Biological Effects of 3H in the Algae *Acetabularia, Chlamydomonas* and *Porphyra*", Current Topics in Radiation Research Quarterly, vol. 12, 1978, pp. 115-132.
Boros et al., "Genistein Inhibits Nonoxidative Ribose Synthesis in MIA Pancreatic Adenocarcinoma Cells: A New Mechanism of Controlling Tumor Growth", Pancreas, vol. 22, No. 1, 2001, pp. 1-7.
Boros et al., "Metabolic Profiling of Cell Growth and Death in Cancer: Applications in Drug Discovery", Drug Discovery Today, vol. 7, No. 6, Mar. 2002, pp. 364-372.
Bravo et al., "Decreased Hepatic Uptake and Processing of High Density Lipoprotein Unesterified Cholesterol and Cholesteryl Ester with Age in the Rat", Journal of Biochemistry, vol. 116, 1994, pp. 1086-1095.
Brown et al., "Treating Patients with Documented Atherosclerosis to National Cholesterol Education Program-Recommended Low-Density-Lipoprotein Cholesterol Goals with Atorvastatin, Fluvastatin, Lovastatin, and Simvastatin", Journal of the American College of Cardiology, vol. 32, 1998, pp. 665-672.
Bucy et al., "Analysis of Lymph Node Biopsies in HIV Infected Patients Before and After HAART", 5th Conference on Retroviruses and Opportunistic Infections, Session 86, vol. 519, 177 Pages (Abstract only).
Caldwell et al., "Quantification of Peptide Isotopomer Abundances and Determination of Protein (sic) Turnover Rates by Using Mass Isotopomer Distribution Analysis", 41st Annual Amer. Society Mass Spectrometry on Mass Spectrometry, 1993, p. 331a (Abstract only).
Cassella et al., "Mechanisms of Lymphocyte Killing by HIV", Current Opinion in Hematology, vol. 4, 1997, pp. 24-31.
Cesar et al., "Direct Measurement of CD4+ and CD8+ T Cell Proliferation Rates in Vivo in AIDS Patients Using a Stable Isotope-Mass Spectrometric Technique", 5th Conference on Retroviruses and Opportunistic Infections, Chicago Illinois, 1998, (Abstract only).
Chinkes et al., "Comparison of Mass Isotopomer Dilution Methods Used to Compute VLDL Production In Vivo", The American Journal of Physiology, vol. 271, 1996, pp. E373-E383.
Christiansen et al., "Effect of Dietary Energy Restriction on Glucose Production and Substrate Utilization in Type 2 Diabetes", Diabetes, vol. 49, Oct. 2000, pp. 1691-1699.
Clarke, R. B., "Isolation and Characterization of Human Mammary Stem Cells", Cell Proliferation, vol. 38, 2005, pp. 375-386.
Clayton, "Replication and Transcription of Vertebrate Mitochondrial DNA", Annual Review of Cell Biology, vol. 7, 1991, pp. 453-478.
Cohen et al., "Purine and Pyrimidine Metabolism in Human T Lymphocytes. Regulation of Deoxyribonucleotide Metabolism", The Journal of Biological Chemistry, vol. 258, No. 20, Oct. 25, 1983, pp. 12334-12340.
Cohen, J. "Failure Isn't What It Used to Be . . . But Neither is Success", Science, vol. 279, 1998, pp. 1133-1134.
Collins et al., "A Method for Measuring Mitochondrial Proliferation In Vivo Using 2H2O Incorporation Into Mitochondria DNA", FASEB Journal, vol. 14, No. 4, Mar. 15, 2000, p. A620.
Collins et al., "Measurement of Mitochondrial DNA Synthesis In Vivo Using a Stable Isotope-Mass Spectrometric Technique", Journal of Applied Physiology, vol. 94, 2003, pp. 2203-2211.
Connors et al., "HIV Infection Induces Changes in CD4+ T-Cell Phenotype and Depletions Within the CD4+ T-Cell Repertoire that are Not Immediately Restored by Antiviral or Immune-Based Therapies", Nature Medicine, vol. 3, No. 5, 1997, pp. 533-540.
Conrads et al., "Stable Isotope Labelling in Proteomics", The Synthesis Cambridge Isotope Laboratories, vol. 3, No. 2, Jan. 2002, pp. 1-3.
Craig et al., "The Impact of Physical Activity on Lipids, Lipoproteins, and Blood Pressure in Preadolescent Girls", Pediatrics, vol. 98, 1996, pp. 389-395.
Crain, "Preparation and Enzymatic Hydrolysis of DNA and RNA for Mass Spectrometry", Methods in Enzymology, vol. 193, 1990, pp. 782-790.
Dalvie, D. "Recent Advances in the Applications of Radioisotopes in Drug Metabolism, Toxicology and Pharmacokinetics", Current Pharmaceutical Design, vol. 6, 2000, pp. 1009-1028.
Davis et al., "Effect of Pinitol Treatment on Insulin Action in Subjects with Insulin Resistance", Diabetes Care, vol. 23, No. 7, Jul. 2000, pp. 1000-1005.
Deeks et al., "CD4+ T Cell Kinetics and Activation in Human Immunodeficiency Virus-Infected Patients who Remain Viremic Despite Long-Term Treatment with Protease Inhibitor-Based Therapy", The Journal of Infectious Diseases, vol. 185, Feb. 1, 2002, pp. 315-323.
Deeks et al., "Viral Load and CD4+ T Cell Changes In Patients Failing Potent Protease Inhibitor Therapy", 5th Conference on Retroviruses and Opportunistic Infections, Session 53, vol. 419, 1998, p. 158 (Abstract only).
Dekker et al., "Glucose Homeostasis in Children with *falciparum* Malaria: Precursor Supply Limits Gluconeogenesis and Glucose Production", J. Clin. Endocrinol. Metabol., vol. 82, 1997, pp. 2514-2521.
Di Buono et al., "Comparison of Deuterium Incorporation and Mass Isotopomer Distribution Analysis for Measurement of Human Cholesterol Biosynthesis", Journal of Lipid Research, vol. 41, 2000, pp. 1516-1523.
Dimitrov et al., "Scientific Correspondence", Nature, vol. 375, 1995, pp. 194-195.
Emken et al., "Incorporation of Deuterium-Labeled Trans- and CIS-13-Octadeconoic Acids in Human Plasma Lipids", Journal of Lipid Research, vol. 24, 1983, pp. 34-41.
Emken, E. A., "Metabolism of Dietary Stearic Acid Relative to Other Fatty Acids in Human Subjects", The American Journal of Clinical Nutrition, vol. 60, (Suppl), 1994, pp. 1023S-1028S.
Etnier et al., "Metabolism of Organically Bound Tritium in Man", Radiation Research, vol. 100, 1984, pp. 487-502.
Fagerquist et al., "Elimination of the Concentration Dependence in Mass Isotopomer Abundance Mass Spectrometry of Methyl Palmitate Using Metastable Atom Bombardment", Journal of the American Society of Mass Spectrometry, vol. 12, 2001, pp. 754-761.
Fagerquist et al., "Molecular Ion Fragmentation and its Effects on Mass Isotopomer Abundances of Fatty Acid Methyl Esters Ionized by Electron Impact", Journal of the American Society of Mass Spectrometry, vol. 10, 1999, pp. 430-439.
Feldman et al., "Chlordiazepoxide-Fluoxetine Interactions on Food Intake in Free-Feeding Rats", Pharmacology Biochemistry & Behavior, vol. 8, No. 6, 1978, pp. 749-752.
Gasparini et al., "Amplification of DNA from Epithelial Cells in Urine", The New England Journal of Medicine, vol. 320, No. 12, 1989, p. 809.
Gerling et al., "Prediction of Liver Fibrosis According to Serum Collagen VI Level in Children with Cystic Fibrosis", The New England Journal of Medicine, vol. 336, No. 22, 1997, pp. 1611-1612.

(56) References Cited

OTHER PUBLICATIONS

Gorochov et al., "Perturbation of CD4+ and CD8+ T-Cell Repertoires During Progression to AIDS and Regulation of the CD4+ Repertoire During Antiviral Therapy", Nature Medicine, vol. 4, 1998, pp. 215-221.

Goz, "The Effects of Incorporation of 5-Halogenated Deoxyuridines into the DNA of Eukaryotic Cells", Pharmacological Reviews, vol. 29, 1977, pp. 249-272.

Gratzner, "Monoclonal Antibody to 5-Bromo- and 5-Iododeoxyuridine: A New Reagent for Detection of DNA Replication", Science, vol. 218, 1982, pp. 474-475.

Guo et al., "De Novo Lipogenesis in Adipose Tissue of Lean and Obese Women: Application of Deuterated Water and Isotope Ratio Mass Spectrometry", International Journal of Obesity and Related Metabolic Disorders, vol. 24, 2000, pp. 932-937.

Gygi et al., "Using Mass Spectrometry for Quantitative Proteomics", Proteomics: A Trends Guide, 2000, pp. 31-36.

Hansen et al., "A Practical Method for Uniform Isotopic Labeling of Recombinant Proteins in Mammalian Cells", Biochemistry, vol. 31, 1992, pp. 12713-12718.

Heck et al., "Posttranslational Amino Acid Epimerization: Enzyme-Catalyzed Isomerization of Amino Acid Residues in Peptide Chains", Proceedings of the National Academy of Sciences of the United States of America, vol. 93, Apr. 1996, pp. 4036-4039.

Hellerstein, "Mass Isotopomer Distribution Analysis: A Technique for Measuring Biosynthesis and Turnover of Polymers", The American Journal of Physiology, vol. 263, 1992, pp. E988-E1001.

Hellerstein et al., "Altered Fluxes Responsible For Reduced Hepatic Glucose Production and Gluconeogenesis by Exogenous Glucose in Rats", The American Journal of Physiology, vol. 272, 1997, pp. E163-E172.

Hellerstein et al., "Directly Measured Kinetics of Circulating T Lymphocytes in Normal and HIV-1-Infected Humans", Nature Medicine, vol. 5, 1999, pp. 83-89.

Hellerstein et al., "Effects of Cigarette Smoking and its Cessation on Lipid Metabolism and Energy Expenditure in Heavy Smokers", J. Clin. Invest., vol. 93, 1994, pp. 265-272.

Hellerstein et al., "Glycoconjugates as Noninvasive Probes of Intrahepatic Metabolism: Pathways of Glucose Entry into Compartmentalized Hepatic UDP-glucose Pools during Glycogen Accumulation", Proceedings of the National Academy of Sciences of the United States of America, vol. 83, No. 18, 1986, pp. 7044-7048.

Hellerstein et al., "Hepatic Gluconegenic Fluxes and Glycogen Turnover During Fasting in Humans. A Stable Isotope Study", The Journal of Clinical Investigation, vol. 100, No. 5, Sep. 1997, pp. 1305-1319.

Hellerstein et al., "Mass Isotopomer Distribution Analysis at Eight Years: Theoretical, Analytic, and Experimental Considerations", The American Journal of Physiology, vol. 276, 1999, pp. E1146-E1170.

Hellerstein et al., "Mass Isotopomer Distribution Analysis for Measuring Fluxes Through Intracellular Metabolic Pathways and Biosynthetic Rates of Polymers", IFAC Modeling and Control in Biomedical Systems, 1994, pp. 353-359.

Hellerstein et al., "Measurement of Hepatic Ra UDP-glucose in Vivo in Rats: Relation to Glycogen Deposition and Labeling Patterns", The American Journal of Physiology, vol. 272, 1997, pp. E155-E162.

Hellerstein et al., "Measurement of Synthesis Rates of Slow-turnover Proteins from 2H2O Incorporation into Non-essential Amino Acids (NEAA) and Application of Mass Isotopomer Distribution Analysis (MIDA)", Faseb Journal Experimental Biology, Meeting, vol. 16, 2002, p. A256 (Abstract only).

Hellerstein et al., "Model for Measuring Absolute Rates of Hepatic de Novo Lipogensis and Reesterification of Free Fatty Acids", The American Journal of Physiology, vol. 265, 1993, pp. E814-E820.

Hellerstein et al., "Subpopulations of Long-Lived and Short-Lived T Cells in Advanced HIV-1 Infection", The Journal of Clinical Investigation, vol. 112, No. 6, 2003, pp. 956-966.

Hellerstein et al., "T Cell Turnover in HIV-1 Disease", Immunity, vol. 7, 1997, pp. 583-589.

Hellerstein, M. K., "Carbohydrate-Induced Hypertriglyceridemia: Modifying Factors and Implications for Cardiovascular Risk", Curr. Opin. Lipidology, vol. 13, 2002, pp. 33-40.

Hellerstein, M. K., "Measurement of T-Cell Kinetics: Recent Methodologic Advances", Trends Immunology Today, vol. 20, No. 10, 1999, pp. 438-441.

Hellerstein, M. K., "Methods for Measurement of Fatty Acid and Cholesterol Metabolism", Current Opinion in Lipidology, vol. 6, 1995, pp. 171-181.

Hellerstein, M. K., "New Stable Isotope-Mass Spectrometric Techniques for Measuring Fluxes through Intact Metabolic Pathways in Mammalian Systems: Introduction of Moving Pictures into Functional Genomics and Biochemical Phenotyping", Metabolic Engineering, vol. 6, 2004, pp. 85-100.

Hellerstein, M. K., "No Common Energy: de Novo Lipogenesis as the Road Less Traveled", The American Journal of Clinical Nutrition, vol. 74, 2001, pp. 707-708.

Hellerstein, M. K., "Synthesis of Fat in Response to Alterations in Diet: Insights from New Stable Isotope Methodologies", Lipids, vol. 31 (Supp), 1996, pp. S117-S125.

Hellerstein, M. K., "The Changing Face of AIDS: Translators Needed", The American Journal of Clinical Nutrition, vol. 70, 1999, pp. 787-788.

Hellerstein, Marc K., "In Vivo Measurement of Fluxes Through Metabolic Pathways: The Missing Link in Functional Genomics and Pharaceutical Research", Annu. Rev. Nutr., vol. 3, 2003, pp. 379-402.

Ho et al., "Rapid Turnover of Plasma Virions and CD4 Lymphocytes in HIV-1 Infection", Nature, vol. 373, 1995, pp. 123-126.

Hoh et al., "De Novo Lipogenesis Predicts Short-Term Body-Composition Response by Bioelectrical Impedance Analysis to Oral Nutritional Supplements in HIV-Associated Wasting", The American Journal of Physiology, vol. 68, 1998, pp. 154-163.

Hsieh et al., "Dynamics of Keratinocytes in Vivo Using 2H2O Labeling: A Sensitive Marker of Epidermal Proliferation State", J Invest Dermatol, vol. 123, 2004, pp. 530-536.

Hudgins et al., "Human Fatty Acid Synthesis is Stimulated by a Eucaloric Low Fat, High Carbohydrate Diet", J. Clin. Invest., vol. 97, No. 9, 1996, pp. 2081-2091.

Hudgins et al., "Relationship Between Carbohydrate-Induced Hypertriglyceridemia and Fatty Synthesis in Lean and Obese Subjects", J. Lipid Res., vol. 41, 2000, pp. 595-604.

Hulzebos et al., "Measurement of Parameters of Cholic Acid Kinetics in Plasma using a Microscale Stable Isotope Dilution Technique: Application to Rodents and Humans", Journal of Lipid Research, vol. 42, 2001, pp. 1923-1929.

Humphrey et al., "A New Method for the Measurement of Protein Turnover", Biochem. J., vol. 148, 1975, pp. 119-127.

Humphrey et al., "A Sensitive Method for Measuring Protein Turnover Based on the Measurement of 2-3H-labeled Amino Acids in Proteins", Biochem. J., vol. 156, 1976, pp. 561-568.

Iyengar et al., "Human Stools as a Source of Viable Colonic-Epithelial Cells", The FASEB Journal, vol. 5, 1991, pp. 2856-2859.

James, J. S., "Clinical Implications of Virological Failure: Interview with Steven Deeks, M.D., San Francisco General Hospital", AIDS Treatment News, vol. 289, 1998, pp. 6-7.

Jennings et al., "The Use of Infrared Spectrophotometry for Measuring Body Water Spaces", Clinical Chemistry, vol. 45, No. 7, Jul. 1999, pp. 1077-1081.

Jones et al., "An Integrated 2H and 13C NMR Study of Gluconeogenesis and TCA Cycle Flux in Humans", American Journal of Physiology-Endocrinology and Metabolism, vol. 281, 2001, pp. E848-856.

Jones et al., "Evidence for Diurnal Periodicity in Human Cholesterol Synthesis", Journal of Lipid Research, vol. 31, 1990, pp. 667-673.

Jones et al., "Interaction of Dietary Fat Saturation and Cholesterol Level on Cholesterol Synthesis Measured Using Deuterium Incorporation", Journal of Lipid Research, vol. 35, 1994, pp. 1093-1101.

Jung et al., "Metabolic Adaptations to Dietary Fat Malabsorption in Chylomicron-Deficient Mice", Biochem. J., vol. 343, 1999, pp. 473-478.

Jungas et al., "Fatty Acid Synthesis in Adipose Tissue Incubated in Tritiated Water", Biochemistry, vol. 7, No. 10, 1968, pp. 3708-3717.

(56) References Cited

OTHER PUBLICATIONS

Katz, "Futile Cycles in the Metabolism of Glucose", Curr. Top Cell Regul., vol. 10, 1976, pp. 237-289.

Kelleher et al., "Model Equations for Condensation Biosynthesis Using Stable Isotopes and Radioisotopes", Am. J. Physiol., vol. 262, 1992, pp. E118-E125.

Khairallah et al., "Assessment of Protein Turnover in Prefused Rat Liver: Evidence for Amino Acid Compartmentation from Differential Labeling of Free and tRNA-bound Valine", J Biol Chem, vol. 251, No. 5, 1976, pp. 1375-1384.

Kim et al., "A New Stable Isotope-Mass Spectrometric (MS) Method to Measure Proliferation Rates of Colon Epithelial Cells", Faseb Journal, vol. 14, No. 4, 2000, p. A718.

Lammert et al., "Effects of Isoenergetic Overfeeding of Either Carbohydrate or Fat in Young Men", British Journal of Nutrition. vol. 84, 2000, pp. 233-245.

Lee, "Cardiorespiratory Fitness, Body Composition, and All-Cause Cardiovascular Disease Mortality in Men 1-3", Am. J. Clin. Nutr., vol. 69, 1999, pp. 373-380.

Lefebvre, "Naturally Labeled 13C-Glucose: A New Tool to Measure Oxidation Rates of Exogenous Glucose", Diabetes, vol. 28 (Suppl. 1), Jan. 1979, pp. 63-65.

Leung et al., "A Deficiency of Microsomal Triglyceride Transfer Protein Reduces Apolipoprotein B Secretion", The Journal of Biological Chemistry, vol. 275, No. 11, 2000, pp. 7515-7520.

Lewanczuk et al., "Comparison of the [13 C] Glucose Breath Test to the Hyperinsulinemic-Euglycernic Clamp When Determining Insulin Resistance", Diabetes Care, vol. 27, No. 2, 2004, pp. 441-447.

Lipkin, "Cell Proliferation Kinetics in the Gastrointestinal Tract of Man I. Cell Renewal in Colon and Rectum", Journal of Clinical Investigations, vol. 42, No. 6, 1963, pp. 767-776.

Lipkin, "Proliferation and Differentiation of Normal and Diseased Gastrointestinal Cells", In Physiology of the Gastrointestinal Tract, L.R. Johnson ed., Raven Press, New York, 1987, pp. 255-284.

Lutton et al., "Critical analysis of the Use of 14C-acetate for Measuring In Vivo Rat Cholesterol Synthesis", Reprod. Nutr. Dev., vol. 30, 1990, pp. 71-84.

Macallan et al., "Measurement of Cell Proliferation by Labeling of DNA with Stable Isotope-Labeled Glucose: Studies in Vitro, in Animals, and in Humans", Proc. Natl. Acad. Sci., vol. 95, 1998, pp. 708-713.

Maentausta et al., "Radioimmunoassay of Conjugated Cholic Acid, Chenodeoxycholic Acid, and Deoxycholic Acid from Human Serum, with Use of 125I-Labeled Ligands", Clin. Chem., vol. 25, No. 2, 1979, pp. 264-268.

Malberg et al., "Chronic Antidepressant Treatment Increases Neurogenesis in Adult Rat Hippocampus", The Journal of Neuroscience, vol. 20, No. 24, Dec. 15, 2000, pp. 9104-9110.

Margolick et al., "Failure of T-cell Homeostasis Preceding AIDS in HIV-1 Infection", Nature Medicine, vol. 1, No. 7, 1995, pp. 674-680.

Maric et al., "Functional Ionotropic Glutamate Receptors Emerge During Terminal Cell Division and Early Neuronal Differentiation of Rat Neuroepithelial Cells", Journal of Neuroscience Research, vol. 61, No. 6, 2000, pp. 652-662.

Marin et al., "Dynamic Profiling of the Glucose Metabolic Network in Fasted Rat Hepalocytes using [1,2-13C2] Glucose", Biochemical Journal, vol. 381, 2004, pp. 287-294.

Martin et al., "Discovery of a Human Liver Glycogen Phosphorylase Inhibtor That Lowers Blood Glucose in Vivo", Proc. Natl. Acad. Sci. USA, vol. 95, No. 4, 1998, pp. 1776-1781.

Mathur-De Vre et al., "Molecular Aspects of Tritiated Water and Natural Water in Radiation Biology", Prog. Biophys. Molec. Biol., vol. 43, 1984, pp. 161-193.

McCloskey, "Electronlonization Mass Spectra of Trimethylsilyl Derivatives of Nucleotides", Meth. Enz., vol. 193, 1990, pp. 825-841.

McCune et al., "Factors Influencing T-Cell Turnover in HIV-1 Seropositive Patients", J. Clin. Invest., vol. 105, 2000, pp. R1-R8.

McCune, J.M., "Thymic Function in HIV-1 Disease", Seminars in Immunology, vol. 9, 1997, pp. 397-404.

McFarland et al., "Inhibition of DNA Synthesis in Neonatal Rat Brain Regions Caused by Acute Nicotine Administration", Developmental Brain Research, vol. 58, No. 2, Feb. 22, 1991, pp. 223-229.

McLean et al., "In Vivo Estimates of Division and Death Rates of Human T Lymphocytes", Proc. Natl. Acad. Sci. USA, vol. 92, 1995, pp. 3707-3711.

Meier et al., "Rates of Protein Synthesis and Turnover in Fetal Life", Am J Physiol., vol. 240, No. 3, 1981, pp. E320-E324.

Mellors et al., "Prognosis in HIV-1 Infection Predicted by the Quantity of Virus in Plasma", Science, vol. 272, 1996, pp. 1167-1170.

Mellors et al., "Quantitation of HIV-1 RNA in Plasma Predicts Outcome after Seroconversion", Ann. Intern. Med., vol. 122, 1995, pp. 573-579.

Messmer et al., "In Vivo Measurements Document the Dynamic Cellular Kinetics of Chronic Lymphocytic Leukemia B Cells", J. Clin. Invest., vol. 115, Feb. 10, 2005, pp. 755-764.

Mewissen et al., "Comparitive Incorporation of Tritium from Tritiated Water Versus Tritiated Thymidine, Uridine or Leucine", Curr. Top Rad. Res. Quart., vol. 12, 1977, pp. 225-254.

Michie et al., "Lifespan of Human Lymphocyte Subsets Defined by CD45 Isoforms.", Nature, vol. 360, 1992, pp. 264-265.

Mikkola et al., "Serum Cholesterol Efflux Potential is an Independent Predictor of Coronary Artery Atherosclerosis", Atherosclerosis, vol. 170, 2003, pp. 31-38.

Mindham et al., "Application of Simultaneous Spleen and Liver Perfusion to the Study of Reverse Cholesterol Transport", Biochemical Journal, vol. 302, 1994, pp. 207-213.

Missell et al., "A new in Vivo Stable Isotope Method for Measuring Mammary Epithelial Cell Proliferation", Faseb Journal Experimental Biology, vol. 14, No. 4, 2000, p. 550.

Mohri et al., "Increased Turnover of T Lymphocytes in HIV-1 Infection and its Reduction by Antiretroviral Therapy", J. Exp. Med., vol. 194, No. 9, 2001, pp. 1277-1287.

Morris et al., "Evidence that a Slowly Cycling Subpopulation of Adult Murine Epidermal Cells Retains Carcinogen", Cancer Research, vol. 46, 1997, pp. 3061-3066.

Morris et al., "Evidence that Cutaneous Carcinogen-Initiated Epithelial Cells from Mice are Quiescent Rather than Actively Cycling", Cancer Research, vol. 57, 1997, pp. 3436-3443.

Morsches, "Tierexperimentelle Untersuchungen Uber Die Beziehungen Zwischen Der Hydroxyprolinausscheidung Im Urin Und Den Hydroxyprolinfraktionen Im Serum", Der Hautarzt, vol. 27, 1976, pp. 234-242.

Mosier, D. E., "CD4,sup.+ Cell Turnover", Nature, vol. 375, 1995, pp. 193-194.

Murali-Krishna et al., "Counting Antigen-Specific CD8 T Cells: A Reevaluation of Bystander Activation during Viral Infection", Immunity, vol. 8, 1998, pp. 177-187.

Nagasaka et al., "Endogenous Glucose Production and Glucose Effectiveness in Type 2 Diabetes Subjects Derived From Stable-Labeled Minimal Modal Approach", Diabetes, vol. 48, May 1999, pp. 1054-1056.

Naik et al., "Pharmacological Activation of Liver X Receptors Promotes Reverse Cholesterol Transport In Vivo", Circulation, vol. 113, 2006, pp. 90-97.

Nanjee et al., "Intravenous apoA-lecithin Discs Increase Pre-Beta-HDL Concentration in Tissue-Fluid and Stimulate Reverse Cholesterol Transport in Humans", Journal of Lipid Research, vol. 42, 2001, pp. 1586-1593.

Neese et al., "Advances in the Stable Isotope-Mass Spectrometric Measurement of DNA Synthesis and Cell Proliferation", Analytical Biochemistry, vol. 298, No. 2, 2001, pp. 189-195.

Neese et al., "Gluconeogenesis and Intrahepatic Triose Phosphate Flux in Response to Fasting or Substrate Loads", Journal of Biological Chemistry, vol. 270, No. 24, 1995, pp. 14452-14463.

Neese et al., "Measurement of Endogenous Synthesis of Plasma Cholesterol in Rats and Humans Using MIDA", Am. J. Physiol., vol. 264, 1993, pp. E139-E147.

Neese et al., "Measurement in Vivo of Proliferation Rates of Slow Turnover Cells by 2H2O Labeling of the Deoxyribose Moiety of DNA", Proceedings of the National Academy of Sciences, vol. 99, No. 24, Nov. 26, 2002, pp. 15345-15350.

(56) References Cited

OTHER PUBLICATIONS

Neher et al., "Pyruvate and Thiamine Pyrophosphate Potentiate Cyclic Nucleotide-Induced Steroidogenesis in Isolated Rat Adrenocortical Cells", J. Steroid Biochem., vol. 18, 1983, pp. 1-6.

Ong et al., "Stable Isotope Labeling by Amino Acids in Cell Culture, SILAC, as a Simple and Accurate Approach to Expression Proteomics", Molecular and Cellular Proteomics, vol. 1, 2002, pp. 376-386.

Oshima et al., "COX Selectivity and Animal Models for Colon Cancer", Current Pharmaceutical Design, vol. 8, 2002, pp. 1021-1034.

Ouguerram et al., "A New Labeling Approach Using Stable Isotopes to Study In Vivo Plasma Cholesterol Metabolism in Humans", Metabolism, vol. 51, No. 1, Jan. 2002, pp. 5-11.

Oyaizu et al., "Role of Apoptosis in HIV Disease Pathogenesis", J. of Clinical Immunology, vol. 15, No. 5, 1995, pp. 217-231.

Paku, S. "Origin and Structual Evolution of the Early Proliferating Oval Cells in Rat Liver", American Journal of Pathology, vol. 158, No. 4, Apr. 2001, pp. 1313-1323.

Palmer et al., "Telomere Length, Telomerase Activity, and Replicative Potential in HIV Infection: Analysis of CD4+ and CD8+ T Cells from HIV-discordant Monozygotic Twins", J. Experimental Medicine, vol. 185, No. 7, 1997, pp. 1381-1386.

Panteleo, Giuseppe, "Unraveling the Strands of HIV's Web", Nature Medicine, vol. 5, No. 1, 1999, pp. 27-28.

Papageorgopoulos et al., "Measuring Protein Synthesis by Mass Isotopomer Distribution Analysis (MIDA)", Analytical Biochemistry, vol. 267, 1999, pp. 1-16.

Papageorgopoulos et al., "Toward the Measurement of Protein Synthesis by Mass Isotopomer Distribution Analysis (MIDA): Resolution of Isotopomers in a [d.sub.3 ]-Leucine Enriched Synthetic Oligopeptide Using Electrospray/Quadrupole Mass Spectrometry (ESI/MS)", Federation of American Societies for Experimental Biology, vol. 1022, 1993, p. A177.

Park et al., "Measurement of Small Intestinal Cell Turnover with [6,6, 2H2] Glucose", Berkeley Scientific, Abstract, vol. 1, No. 2, 1997, pp. 41-43.

Parks et al., "Carbohydrate-induced Hypertriacylglycerolemia: Historical Perspective and Review of Biological Mechanisms", Am. J. Nutr., vol. 71, 2000, pp. 412-433.

Parks et al., "Dependence of Plasma a-Tocopherol Flux on Very Low-Density Triglyceride Clearance in Humans", Free Radical Biology & Medicine, vol. 29, No. 11, pp. 1151-1159.

Parks et al., "Effects of a Low-Fat, High-Carbohydrate Diet on VLDL-Triglyceride Assembly, Production, and Clearance", J. Clin. Invest. vol. 104, No. 8, 1999, pp. 1087-1096.

Pasa-Tolic et al., "High Throughput Proteome-Wide Precision Measurements of Protein expression Using Mass Spectrometry", J. Am. Chem. Soc., vol. 121, 1999, pp. 7949-7950.

Patsalos et al., "Pattern of Myelin Breakdown During Sciatic Nerve Wallerian Degeneration: Reversal of the Order of Assembly", The Journal of Cell Biology, vol. 87, 1980, pp. 1-5.

Patterson et al., "Concentration Dependence of Methyl-Palmitate Isotope Ratios by Electron Impact Ionization Gas Chromatography/ Mass Spectrometry", Biol. Mass Spectrom., vol. 22, 1993, pp. 481-486.

Patterson et al., "Measurement of Very Low Stable Isotope Enrichments by Gas Chromatography/Mass Spectrometry: Application to Measurement of Muscle Protein Synthesis", Metabolism, vol. 46, No. 8, Aug. 1997, pp. 943-948.

Patton et al., "Measurements of Fatty Acid Synthesis by Incorporation of Deuterium from Deuterated Water", Biochemistry, vol. 18, No. 14, 1979, pp. 3186-3188.

Perelson et al., "Decay Characteristics of HIV-1 Infected Compartments During Combination Therapy", Nature 387, 1997, pp. 188-191.

Perelson et al., "HIV-1 Dynamics In Vivo: Virion Clearance Rate, Infected Cell Life-Span, and Viral Generation Time", Science, vol. 271, 1996, pp. 1582-1586.

Perochon et al., "Radiolabeling of the Lipids of Chinese Hamster Ovary Cells with the Probe [3-(Trifluoromethyl)-3-(m-[125]iodophenyl)diazirine", Analytical Biochemistry, vol. 254, 1997, pp. 109-118.

Pozharisski et al., "Study of Kinetics of Epithelial Cell Populations in Normal Tissues of the Rat's Intestines and in Carcinogensis", Exp. Path., Bd., vol. 18, 1980, pp. 387-406.

Previs et al., "Estimation of Protein Turnover In Vivo Using D2O", Diabetes Abstract Book, 61st Scientific Sessions, vol. 50, Supplement 2, A301, 2001, 1248-p.

Propper et al., "Use of Positron Emission Tomography in Pharmacokinetic Studies to Investigate Therapeutic Advantage in a Phase I Study of 120-Hour Intravenous Infusion XR5000", Journal of Clinical Oncology, vol. 21, No. 2, Jan. 2003, pp. 203-210.

Ramakers et al., "Chronic Suppression of Bioelectric Activity and Cell Survival in Primary Cultures of Rat Cerebral Cortex Biochemical Observations", European Journal Of Neuroscience, vol. 3, No. 2, 1991, pp. 154-161.

Ravichandran et al., "In Vivo Labeling Studies on the Biosynthesis and Degradation of Collagen in Experimental Myocardial Infarction", Biochemistry Journal, vol. 24, No. 3, 1991, pp. 405-414.

Reichard, P., "From Deoxynucleotides to DNA Synthesis", Federation Proceedings, vol. 37, No. 1, 1978, pp. 9-14.

Reichard, P., "Interactions Between Deoxyribonucleotide and DNA Synthesis", Ann. Rev. Biochem. vol. 57, 1988, pp. 349-374.

Rittenberg et al., "Deuterium as an Indicator in the Study of Intermediary Metabolism—VIII. Hydrogenation of Fatty Acids in the Animal Organism", Journal of Biological Chemistry, vol. 117, Feb. 1937, pp. 485-490.

Rrittenberg et al., "Deuterium as an Indicator in the Study of Intermediary Metabolism—X. The Metabolism of Butyric and Caproic Acids", Journal of Biological Chemistry, vol. 120, Sep. 1937, pp. 503-510.

Rittler et al., "Effect of Tumor Removal on Mucosal Protein Synthesis in Patients with Colorectal Cancer", American Journal of Physiology-Endocrinology and Metabolism, vol. 284, 2003, pp. E1018-E1021.

Roberts, "Use of the Doubly Labeled Water Method for Measurement of Energy Expenditure, Total Body Water, Water Intake, and Metabolizable Energy Intake in Humans and Small Animals", Can. J. Physiol. Pharmacol., vol. 67, No. 10, 1989, pp. 1190-1198.

Robin et al. "Mitochondria DNA Molecules and Virtual Number of Mitochondria per Cell in Mammalian Cells", Journal of Cellular Physiology, vol. 136, 1988, pp. 507-513.

Robosky, L. C., "In Vivo Toxicity Screening Programs Using Metabonomics", Combinatorial Chemistry & High Throughput Screening, vol. 5, 2002, pp. 651-662.

Rocha et al., "Accumulation of Bromodeoxyuridine-Labelled Cells in Central and Peripheral Lymphoid Organs: Minimal Estimates of Production and Turnover Rates of Mature Lymphocytes", Eur. J. Immunol., vol. 20, 1990, pp. 1697-1708.

Roda et al., "Results with Six 'Kit' Radioimmunoassays for Primary Bile Acids in Human Serum Intercompared", Clin. Chem., vol. 26, No. 12, 1980, pp. 1677-1682.

Roederer, M. "T-Cell Dynamics of Immunodeficiency", Nature Medicine, vol. 1, No. 7, Jul. 1995, pp. 621-622.

Rooyackers et al., "Tracer Kinetics Are of Limited Value to Measure In Vivo Protein Synthesis and Degradation Rates in Muscle of Anesthetized Rats", Metabolism, vol. 45, No. 10, Oct. 1996, pp. 1279-1283.

Rosin et al., "The Use of Exfoliative Cell Samples to Map Clonal Genetic Alterations in the Oral Epithelium of High-Risk Patients", Cancer Research, vol. 57, Dec. 1, 1997, pp. 5258-5260.

Royale et al., "Techniques for Investigating Substrate Metabolism in Patients", Annals of the Royal College of Surgeons of England, vol. 63, 1981, pp. 415-419.

Santarelli et al., "Requirement of Hippocampal Neurogenesis for the Behavioral Effects of Antidepressants", Science, vol. 301, No. 5634, Aug. 8, 2003, pp. 805-809.

Sawada et al., "Comparison of Autoradiography, Liquid Scintillation Counting and Immunoenzymatic Staining of 5-bromo-2'-

(56) References Cited

OTHER PUBLICATIONS deoxyuridine for Measurement of Unscheduled DNA Synthesis and Replicative DNA Synthesis in Rat Liver", Mutation Research, vol. 344, 1995, pp. 109-116.

Scalise, K., "Tracking T-Cells in AIDS Patients: A Safe Reliable Method of Measuring Human Cell Generation Rates", Berkeleyan, Feb. 11-17, 1998, 3 pages.

Scheibner et al., "Bile Acid Synthesis from Newly Synthesized Vs. Preformed Cholesterol Precursor Pools in the Rat", Hepatology, vol. 17, 1993, pp. 1095-1102.

Scheibner et al., "Complex Feedback Regulation of Bile Acid Synthesis in the Hamster: The Role of Newly Synthsized Cholesterol", Hepatology, vol. 30, 1999, pp. 230-237.

Schneiter et al., "Kinetics of Dexamethasone Induced Alterations of Glucose Metabolism in Healthy Humans", American Journal of Physiology, 1998, pp. E806-E813.

Schoenheimer et al., "Deuterium as an Indicator in the Study of Intermediary Metabolism—V. The Desaturation of Fatty Acids in Organism", Journal of Biological Chemistry, vol. 113, Mar. 1936, pp. 505-510.

Schwarz et al., "Short-Term Alterations in Carbohydrate Energy Intake In Humans", J. Clin. Invest., vol. 96, 1995, pp. 2735-2743.

Seiler et al., "The influence of catabolic reactions on polyamine excretion", Biochem. J., vol. 225, 1985, pp. 219-226.

Shevchenko et al., "Rapid 'de Novo' Peptide Sequencing by a Combination of Nanoelectrospray, Isotopic Labeling and a Quadrupole/Time-of-flight Mass Spectrometer", Rapid Commun. Mass Spectrom., vol. 11, 1997, pp. 1015-1024.

Shigenaga et al., "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection", Methods in Enzymology, vol. 234, 1994, pp. 16-33.

Siler et al., "De Novo Lipogenesis, Lipid Kinetics, and Whole-Body Lipid Balances in Humans after Acute Alcohol Consumption1-3", American Journal of Clinical Nutrition, vol. 70, 1999, pp. 928-936.

Siler et al., "The Inhibition of Gluconeogenesis Following Alcohol in Humans", Am. J. Physiol., vol. 275, 1996, pp. E897-E907.

Siler et al., "VLDL-Triglyceride Production After Alcohol Ingestion, Studied Using [2-13C1] Glycerol", J. Lipid Res., vol. 39, 1998, pp. 2319-2328.

Smith et al., "The Phosphogluconate Odixative Pathway", in Principles of Biochemistry, 7th edition, McGraw-Hill Book Company, 1983, pp. 417-423.

Sosa-Peinado et al., "Overexpression and Biosynthetic Deuterium Enrichment of TEM-1 Beta-Lactamase for Structural Characterization by Magnetic Resonance Methods", Protein Expression and Purification, vol. 19, No. 2, Jul. 2000, pp. 235-245.

Sprent et al., "CD4+ Cell Turnover", Nature, vol. 375, 1995, 194 pages.

Stingl et al., "Purification and Unique Properties of Mammary Epithelial Stem Cells", Nature, vol. 439, Feb. 2006, pp. 993-997.

Stingl et al., "Characterization of Bipotent Mammary Epithelial Progenitor Cells in Normal Adult Human Breast Tissue", Breast Can Res and Treatment, vol. 67, 2001, pp. 93-109.

Sunter et al., "Cell Population Kinetics in the Epithelium of the Colon of the Male Rat", Virchows Archiv. 8 Cell Path., vol. 26, 1978, pp. 275-287.

Teixeira et al., "Poor CD4 T Cell Restoration After Suppression of HIV-1 Replication May Reflect Lower Thymic Function", AIDS, vol. 15, No. 14, 2001, pp. 1749-1756.

Tint et al., "Transformation of 5α-cholest-7-en-3β-ol to Cholesterol and Cholestanol in Cerebrotendinous Xanthomatosis", Journal of Lipid Research, vol. 15, 1974, pp. 256-262.

Traber et al., "Isolation of Intestinal Epithelial Cells for the Study of Differential Gene Expression Along the Crypt-Villus Axis", Am. J. Physiol., vol. 260, pp. G895-G903.

Trappe et al., "Effect of Ibuprofen and Acetaminophen on Postexercise Muscle Protein Synthesis", Am J Physiology Endocronol Metab, vol. 282, 2002, pp. E551-E556.

Turner, S. M., "Stable Isotopes, Mass Spectrometry, and Molecular Fluxes: Applications to Toxicology", Journal of Pharmacological and Toxicological Methods, vol. 53, 2006, pp. 75-85.

Turner et al., "Emerging Applications of Kinetic Biomarkers in Preclinical and Clinical Drug Development", Current Opinion in Drug Discovery & Development, vol. 8, No. 1, 2005, pp. 115-126.

Turner et al., "Measurement of Triglyceride (TG) Synthesis in Vivo 2H2O Incorporation into TG-Glycerol and Application of Mass Isotopomer Distribution Analysis (MIDA)", Experimental Biology, 2002, 16 [Meeting Abstract 361,9], A400.

Van Hinsbergh et al., "Palmilate Oxidation by Rat Skeletal Muscle Mitochondria", Archives of Biochemistry and Biophysics, vol. 190, No. 2, 1978, pp. 762-771.

Van Loan et al., "Monitoring Changes in Fat-Free Mass in HIV-Positive Men with Hypotestosteronemia and AIDS Wasting Syndrome Treated with Gonadal Hormone Replacement Therapy", AIDS, vol. 13, 1999, pp. 241-248.

Veenstra et al., "Proteome Analysis Using Selective Incorporation of Isotopically Labeled Amino Acids", J. Am. Soc. Mass. Spectrom., vol. 11, 2000, pp. 78-82.

Veerkamp et al., "14CO2 Production is no Adequate Measure of [14C]Fatty Acid Oxidation", Biochemical Medicine and Metabolic Biology, vol. 35, 1986, pp. 248-259.

Véniant et al., "Defining the Atherogenicity of Large and Small Lipoproteins Containing Apolipoproteins B100", J. Clin. Invest., vol. 106, No. 12, 2000, pp. 1501-1510.

Wadke, "Fatty Acid Synthesis by Liver Perfused with Deuterated and Tritiated Water", Biochemistry, vol. 12, No. 14, 1973, pp. 2619-2624.

Wain-Hobson, S., "Virological Mayhem", Nature, vol. 373, 1995, 102 pages.

Waldeman et al., "A Comparison Between Bromodeoxyuridine and 3 H Thymidine Labeling in Human Breast Tumors", Modern Path., vol. 4, No. 6, 1991, pp. 718-722.

Wang et al., "Effects of Nicotinic Acid on Fatty Acid Kinetics, Fuel Selection, and Pathways of Glucose Production in Women", Am. J. Physiol. Endocrinol. Metab., vol. 279, 2000, pp. E50-E59.

Waterlow, "Protein Turnover in the Whole Animal", Invest. Cell Pathol. vol. 3, 1980, pp. 107-119.

Wei et al., "Viral Dynamics in Human Immunodeficiency Virus Type 1 Infection", Nature, vol. 373, 1995, pp. 117-122.

Whittmann et al., "Application of MALDI-TOF MS to lysine-Producing *Corynebacterium glutamicum*: A Novel Approach for Metabolic Flux Analysis", Eur. J. Biochem., vol. 268, 2001, pp. 2441-2455.

Winett et al., "Exercise Regimens for Men With HIV", JAMA, vol. 284, No. 2, 2000, pp. 175-176.

Wolf, George, "The Effect of Fasting and Fructose and Glucose Infusion on Gluconeogenesis and Triose Phosphate Flux in Rats in Vivo", Nutrition Reviews, vol. 53, No. 10, 1995, pp. 299-302.

Wolfe, "Isotopic Measurement of Glucose and Lactate Kinetics", Ann. Med., vol. 22, 1990, pp. 163-170.

Wolfe et al., "Glucose Metabolism in Humans", ACS Symposium Series 258, Chapter 12, Turnund et al. ed., 1984, pp. 175-189.

Wolthers et al., "Rapid CD4+ T-Cell Turnover in HIV-1 Infection: A Paradigm Revisited", Immunology Today, vol. 19, No. 1, 1998, pp. 44-48.

Wolthers et al., "T Cell Telomere Length in HIV-1 Infection: No Evidence for Increased CD4+ T Cell Turnover", Science, vol. 274, 1996, pp. 1543-1547.

Wong et al., "From monoamines to genomic targets: a paradigm shift for drug discovery in depression", Nature Reviews Drug Discovery, vol. 3, Feb. 2004, pp. 136-151.

Wood et al., "Estimation of Pathways of Carbohydrate Metabolism", Biochemische Zeitschrift, vol. 338, 1963, pp. 809-847.

Zhang et al., "Kinetics of CD4+ T Cell Repopulation of Lymphoid Tissues after Treatment of HIV-1 Infection", Proc. Natl. Acad. Sci. USA, vol. 95, Feb. 1998, pp. 1154-1159.

Zhang et al., "Deuterium NMR Study of the Origin of Hydrogen in Fatty Acids Produced In Vivo in Chicken", European Journal of Lipid Science and Technology, vol. 108, 2006, pp. 125-133.

(56) References Cited

OTHER PUBLICATIONS

Zilversmit et al., "On the Calculation of 'Turnover Time' and 'Turnover Rate' from Experiments Involving the Use of Labeling Agents", J. of General Physiology, vol. 26, No. 3, 1943, pp. 325-331.

Asher et al., "Evaluation of Cell Death in EBV-Transformed Lymphocytes Using Agarose Gel Electrophoresis, Light Microscopy and Electron Microscopy, II. Induction of Non-Classic Apoptosis ("Para-Apoptosis") by Tritiated Thymidine", Leukemia & Lymphoma, vol. 19, 1995, pp. 107-119.

European Search Report received for European Patent Application No. 04812281.6, mailed on Oct. 6, 2010, 4 pages.

Comte et al., "Probing the Origin of Acetyl-CoA and Oxaloacetate Entering the Citric Acid Cycle from the 13C Labeling of Citrate Released by Perfused Rat Hearts", The Journal of Biological Chemistry, vol. 272, No. 42, Oct. 17, 1997, pp. 26117-26124.

Price et al., "Measurement of Human Plasma Proteome Dynamics with 2H2O and Liquid Chromatography Tandem Mass Spectrometry", Analytical Biochemistry, vol. 420, 2012, pp. 73-83.

Hinkson et al., "The Dynamic State of Protein Turnover: It's About Time", Trends in Cell Biology, vol. 21, No. 5, May 2011, pp. 293-303.

Linn et al., "Effect of Long-Term Dietary Protein Intake on Glucose Metabolism in Humans", Diabetologia, vol. 43, 2000, pp. 1257-1265.

Nordhoff et al., "Mass Spectrometry of Nucleic Acids", Mass Spectrometry Reviews, vol. 15, 1996, pp. 67-138.

Previs et al., "A Critical Evaluation of Mass Isotopomer Distribution Analysis of Gluconeogenesis in Vivo", American Journal of Physiology-Endocrinology and Metabolism, vol. 277, 1999, E154-E160.

Szymanski et al., "Beyond the Proteome: Non-Coding Regulatory RNAs", Genome Biology, vol. 3, No. 5, Apr. 15, 2002, pp. 1-8.

\* cited by examiner

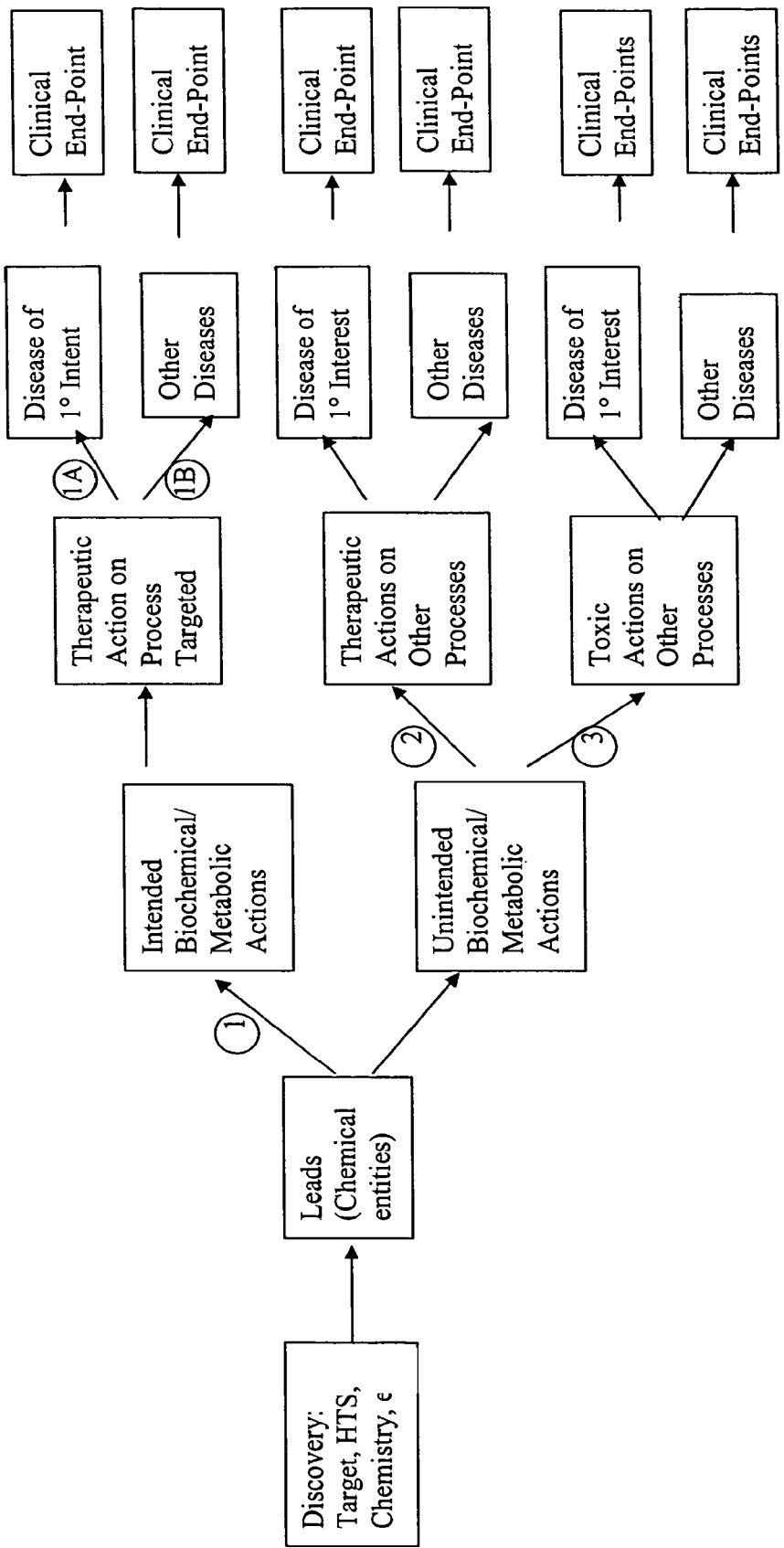
FIGURE 1 – Contemporary Model of Intended vs. Unintended Actions of Drugs

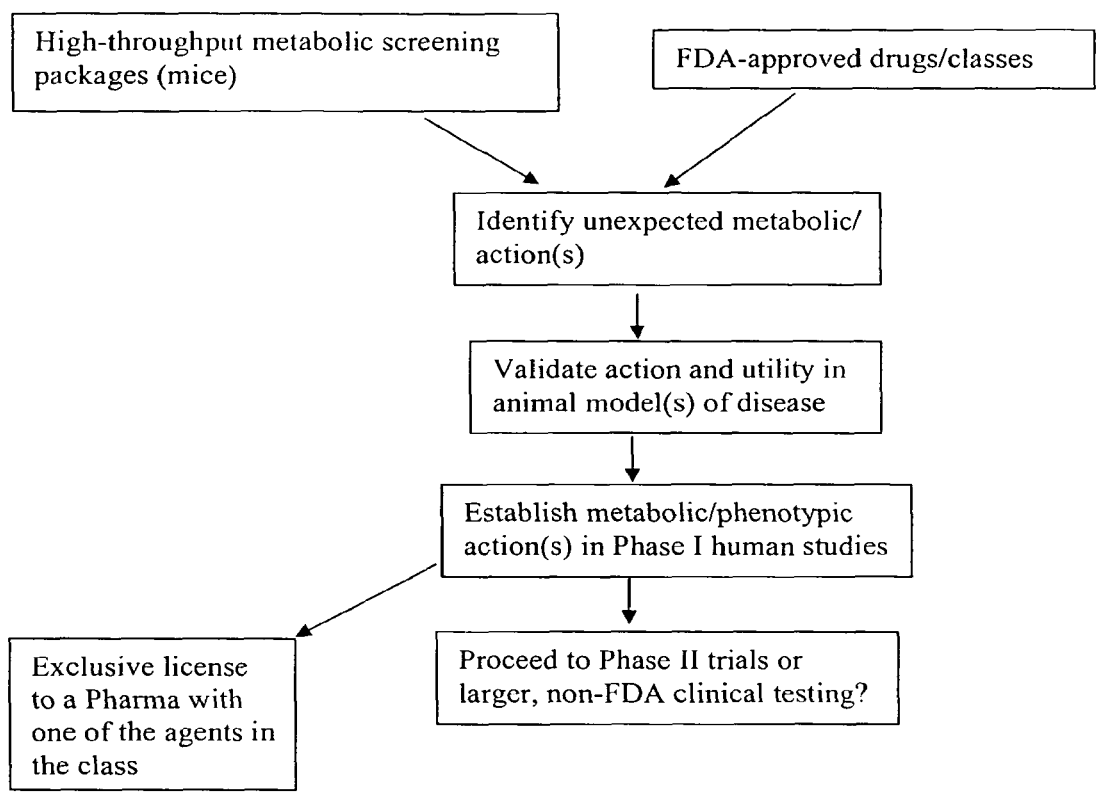
FIGURE 2 – Screening for New Indications of Approved Drugs

FIGURE 3 – Metabolic Pathway for DNA Synthesis
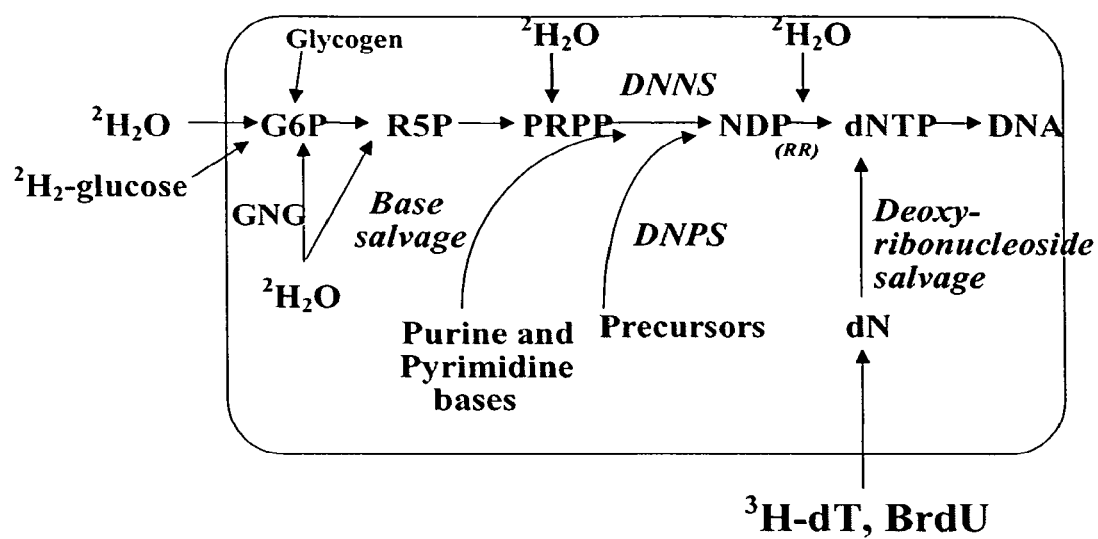

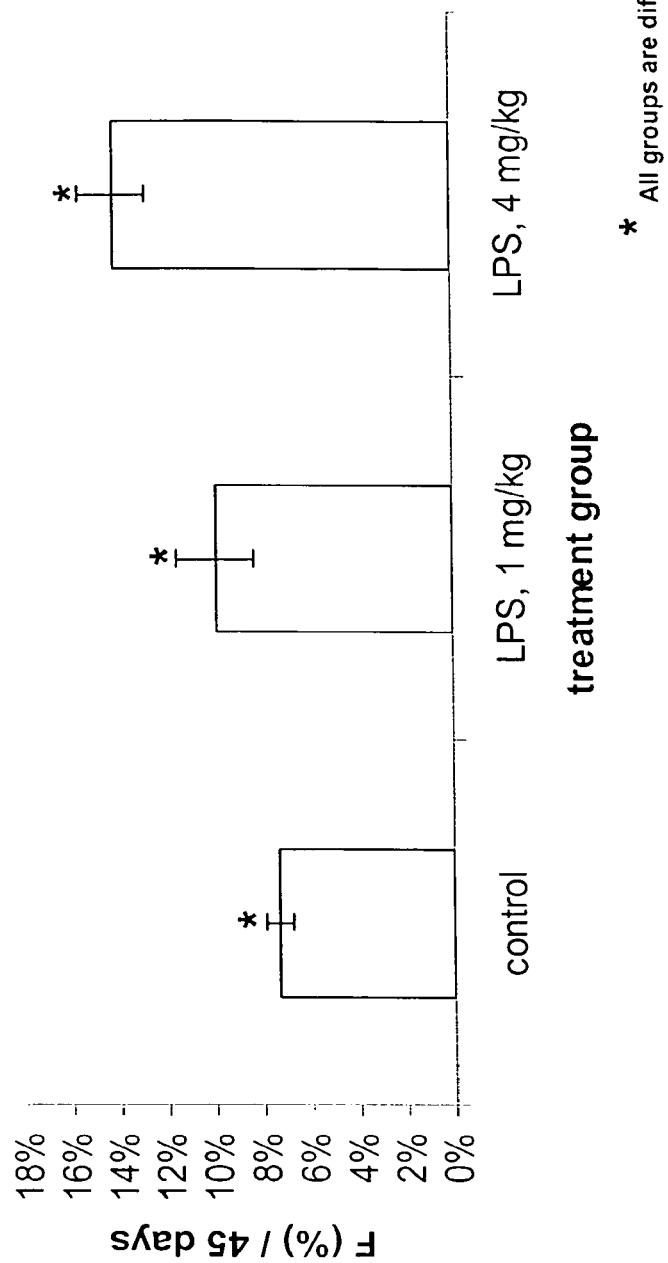

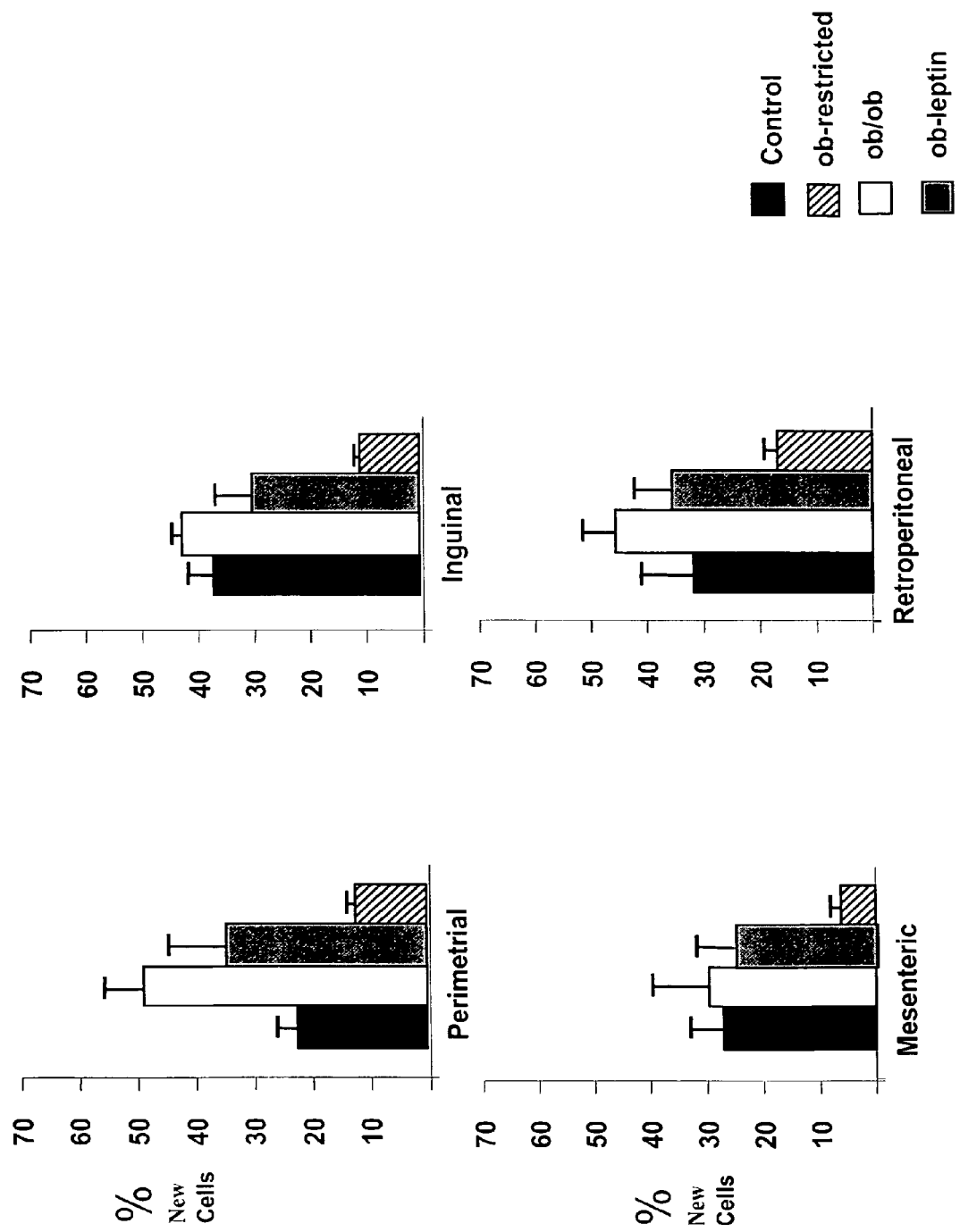
FIGURE 5 – Adipocyte Proliferation in various fat depots

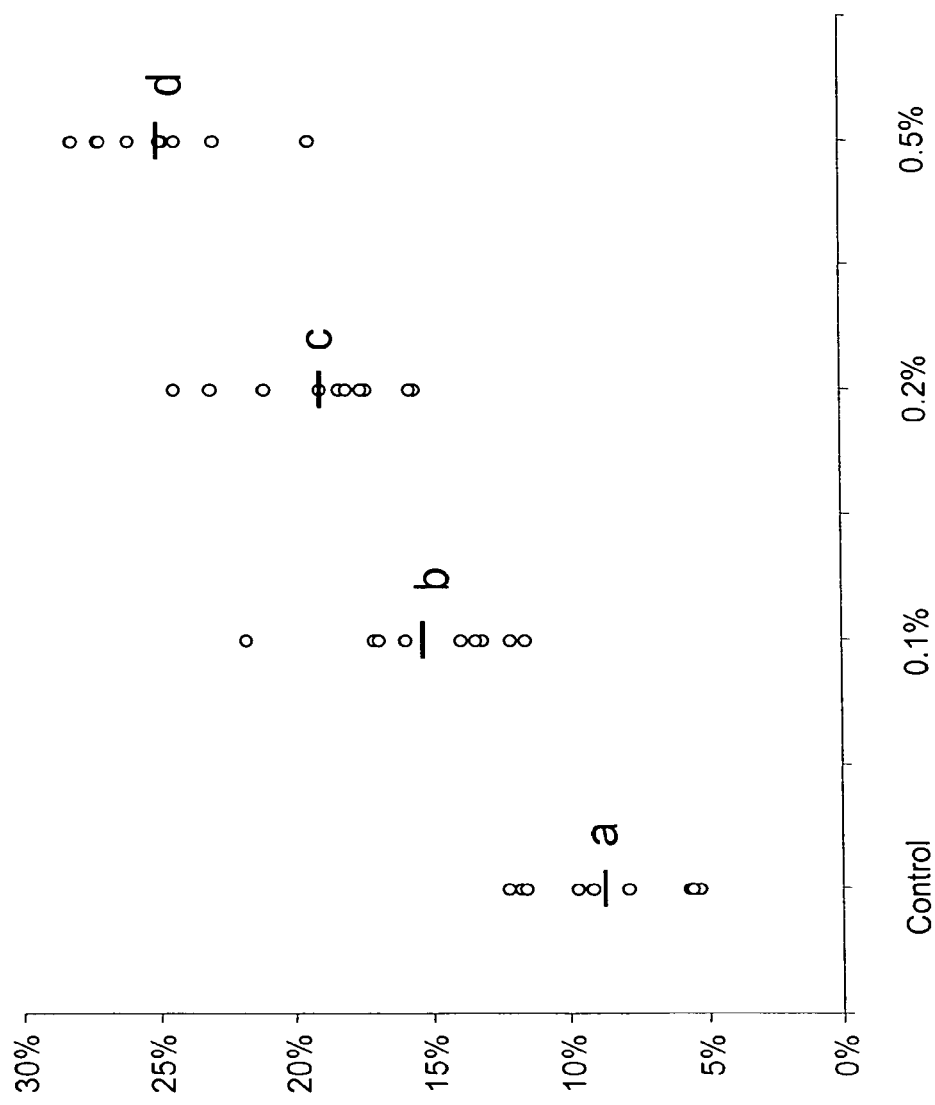
FIGURE 6 – Increase in mouse liver cell proliferation after treatment with griseofulvin

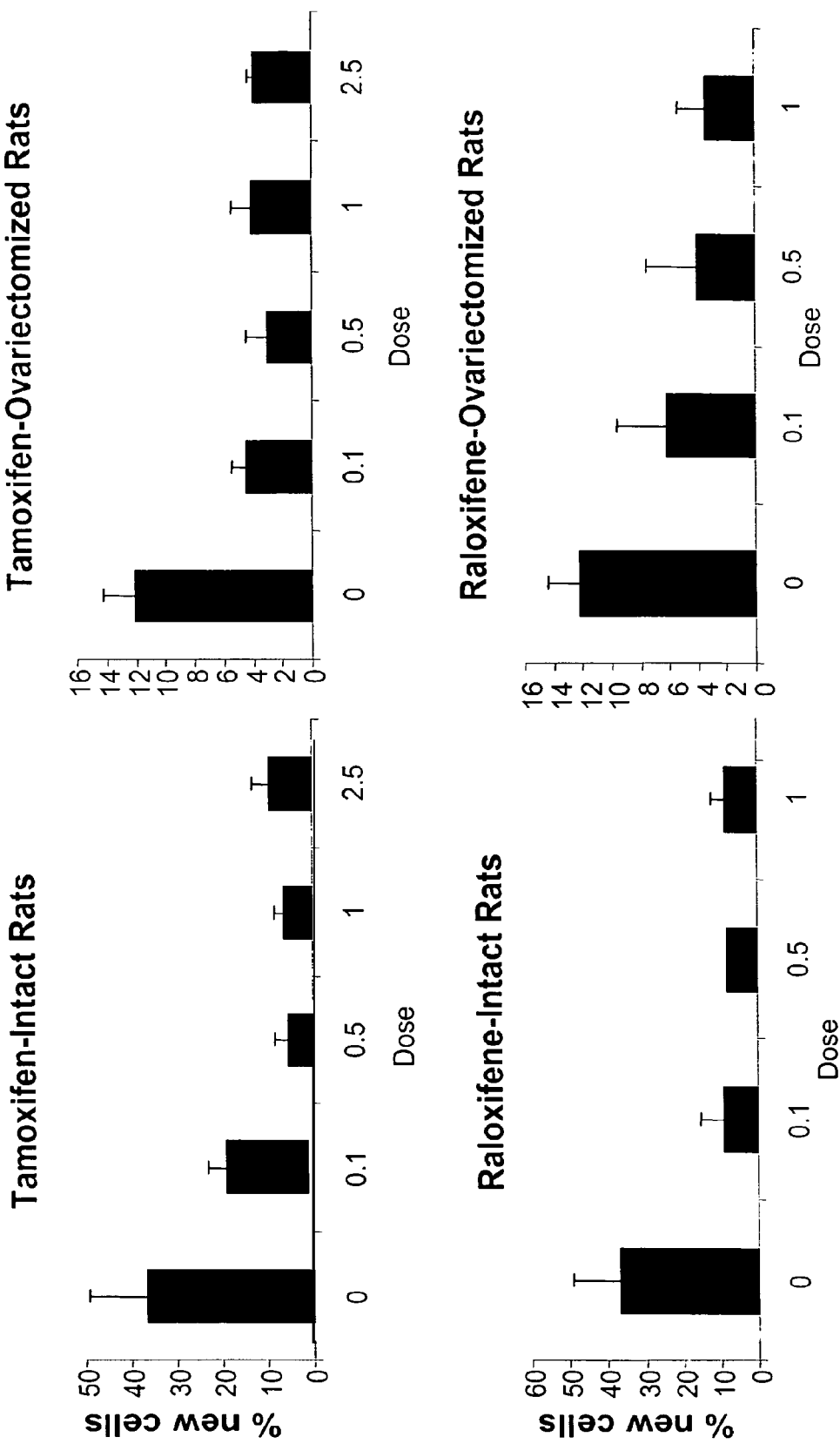
FIGURE 7 - One week of treatment and $^2H_2O$ labeling

FIGURE 8 - Increase in n After Rosiglitazone Treatment in Adipose Tissue
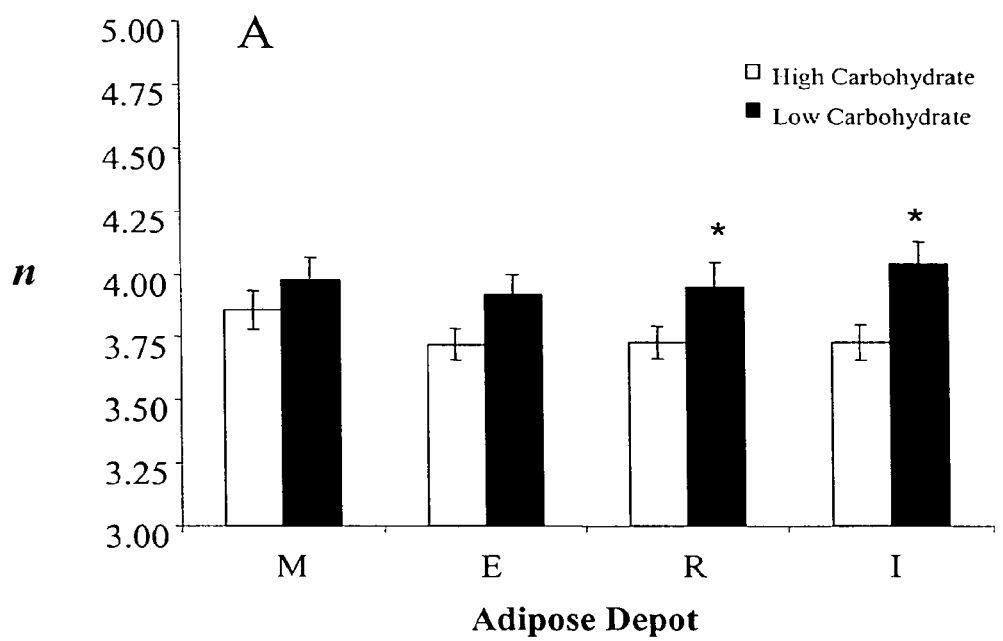
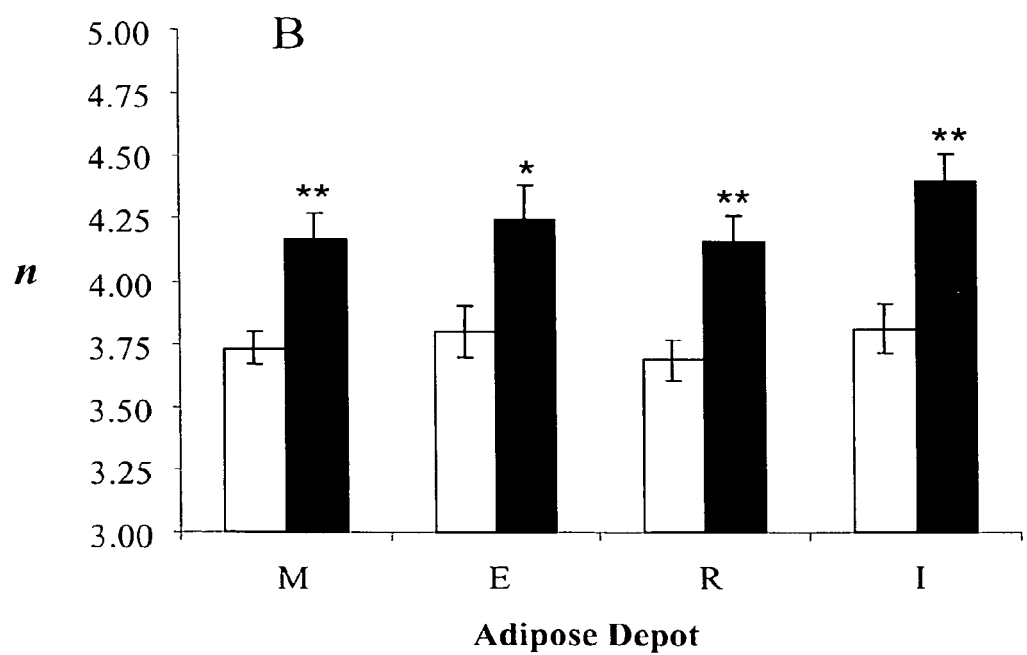

METHOD FOR HIGH-THROUGHPUT SCREENING OF COMPOUNDS AND COMBINATIONS OF COMPOUNDS FOR DISCOVERY AND QUANTIFICATION OF ACTIONS, PARTICULARLY UNANTICIPATED THERAPEUTIC OR TOXIC ACTIONS, IN BIOLOGICAL SYSTEMS

CROSS-REFERENCE TO RELATED APPLICATION

This application is a continuation patent application of U.S. patent application Ser. No. 10/997,323, with a filing date of Nov. 23, 2004, and claims the benefit of U.S. Provisional Patent Application Ser. No. 60/525,261 filed Nov. 25, 2003, which are incorporated herein by reference in their entirety.

FIELD OF THE INVENTION

The invention relates to methods for screening compounds, combinations of compounds, or mixtures of compounds (i.e., drugs and drug candidates, including chemical entities, whether new or known, and biological factors, whether new or known) for actions in biological systems. The disclosed methods measure and quantify molecular flux rates through metabolic pathways (synthesis and breakdown or input and removal rates from pools of molecules) in vivo as targets of drug action. The disclosed methods are capable of high-throughput, large-scale, automated applications. The methods are particularly applicable to detecting and establishing unanticipated or unintended actions of drugs or drug candidates during drug discovery, development and approval (DDDA). The methods disclosed herein are particularly suitable for establishing secondary therapeutic claims ("new uses" or "new indications") and determining toxicities both of known compounds and new compounds.

BACKGROUND OF THE INVENTION

The contemporary system of drug discovery, development and approval (DDDA) is highly specific and target-directed. The system is built on a model of intended biochemical and molecular actions. New compounds (i.e., chemical entities or biological factors) are identified, optimized and evaluated based on their actions on intended therapeutic targets. These intended therapeutic targets are typically proteins or genes believed to be involved in a disease process of interest (the drug target). Increasingly, other cellular macromolecules are also becoming important as drug targets (e.g., mRNA).

Actions on the drug target are evaluated against large numbers of compounds by use of high-throughput screening (HTS) assays that measure the activity or state of the protein or gene target. Compounds showing potentially useful activity on the drug target are termed lead compounds (also known as "drug leads"). Once identified, drug leads are filtered and selected on the basis of their activity on the disease process targeted and, ultimately, on clinical end-points. FDA approval is ultimately given for single, well-defined clinical indications that are identified and defined and tested in advance in specified diseases.

Drug leads are therefore both discovered and developed in the context of a highly constrained set of protocols built on a model of intended actions. Drug targets are specific and are identified in advance for discovery initiatives. Stated differently, FDA approval of a drug lead is not obtained by administration of the compound to diverse people with a variety of random medical disorders to see if it helps one or more of these, but occurs within an explicit context of prospectively defined effects in specific disease states.

This approach of contemporary DDDA has major flaws. First, identifying "hits" by HTS assays against molecular targets hypothesized to be involved in a disease does not in fact establish or prove activity against the disease. Activity against disease still has to be validated independently. Indeed, true in vivo activity and efficacy of drug leads may be unreliably or misleadingly assessed by HTS molecular assays. Second, subsequent validation of drug leads against physiologic models of disease often remains highly inefficient for the chronic conditions that are the major therapeutic targets of current drug research, thereby leading to a downstream roadblock in the DDDA system in the filtering steps. Third, unintended toxic actions of drugs are not identified by this approach. Fourth, unintended or secondary therapeutic actions (i.e., other actions besides the effects on the specific molecular target screened) also are not identified efficiently by this approach, thereby missing out on the detection and discovery of other potential therapeutic uses of compounds on which a pharmaceutical company is already investing time and money to develop. Fifth, synergistic effects of combination therapies on a disease process, occurring by interactions among compounds that act on different biochemical steps in the disease pathway, are not detectable by screening approaches which only measure one step in a disease pathway at a time.

The ideal solution to the problem of unintended actions and functional importance of compounds discovered through screening for specific, intended molecular actions is therefore evident: a systematic method for measuring and identifying unintended actions and functional consequences of compounds, combinations of compounds, and mixtures of compounds. The availability of a systematic procedure for efficient, high-throughput discovery and confirmation of unintended actions of compounds or combinations of compounds or mixtures of compounds on functionally relevant biological processes would therefore radically alter the entire DDDA process. Such methods are disclosed herein, in addition to methods for screening and comparing compounds and combinations of compounds and mixtures of compounds for actions on intended processes.

SUMMARY OF THE INVENTION

The present invention is directed to methods for measuring and quantifying molecular flux rates within one or more metabolic pathways of interest, in response to exposure to one or more compounds, combinations of compounds, or mixtures of compounds, the methods enabling an investigator to discover an unanticipated or unexpected action or actions (or both) elicited by the one or more compounds, combination of compounds, or mixtures of compounds. The methods of the invention include high-throughput screening assays. In one embodiment of the invention, the unanticipated or unexpected action is a therapeutic action. In another embodiment of the invention, the unanticipated or unexpected action is a toxic effect. The methods of the invention permit the identification of compounds that alter the metabolic flux rates of once or more metabolic pathways.

In the present invention, one or more isotope-labeled substrates (i.e., metabolic precursors) are administered to a cell, tissue or organism for a period of time sufficient for the isotope label to be incorporated into one or more targeted molecules in at least one targeted metabolic pathway of interest. More than one isotope label may be administered. Measurement of the isotopic content and/or pattern or the rate of change of the isotopic content and/or pattern in the one or more targeted molecules is performed to calculate the molecular flux rate in the one or more pathways of interest. One or more compounds are administered (constituting exposure) to a living system and the molecular flux rates are measured in the presence and absence of exposure. In a further embodiment of the invention, the molecular flux rates are measured in response to a specific dose or a range of doses of the one or more compounds. In another embodiment of the invention, the molecular flux rates are measured in response to exposure to a combination of compounds. In still another embodiment of the invention, the molecular flux rates are measured in response to exposure to a mixture of compounds.

The one or more compounds can be a new chemical entity, a chemical entity drug lead (i.e., a "small molecule" drug lead), or a known chemical entity drug (i.e., a "small molecule" drug), for example an already-approved drug listed in the Physician's Desk Reference (PDR) or the Merck Index (e.g., a drug approved by the FDA or other corresponding agencies outside the U.S.). The one or more compounds also can be a new biological factor or a known biological factor including an already-approved biological factor drug. The one or more compounds can be selected randomly or on the basis of a specific biochemical rationale concerning a hypothesized role in the molecular pathogenesis of one or more diseases.

The invention allows for the comparison between the molecular flux rates measured from exposed cells, tissues, or organisms of the living system to the molecular flux rates measured from non-exposed cells, tissues, or organisms of the living system. Differences between the exposed and non-exposed molecular flux rates are identified and this information is then used to determine whether one or more compounds (or combinations of compounds or mixtures of compounds) elicit a metabolic action on the one or more pathways of interest on the exposed cell, tissue, or organism. The metabolic action of the compound (or combination of compounds or mixture of compounds) on the exposed cell, tissue or organism may be unexpected or unanticipated (based on prevailing biochemical knowledge and concepts about the compound and molecular flux within the pathway) or may be anticipated or expected. The one or more compounds (or combination of compounds or mixture of compounds) can be administered to a mammal and the molecular flux rates calculated and evaluated against the molecular flux rates calculated from an unexposed mammal of the same species. The mammal may be a human.

In another embodiment of the invention, the molecular flux rates are measured in one or more metabolic pathways involved in the molecular pathogenesis of a disease. In a further embodiment, the one or more metabolic pathways are the cause of the disease or contribute to the initiation, progression, activity, pathologic consequences, symptoms, or severity of the disease.

In another embodiment of the invention, the molecular flux rates from one or more metabolic pathways are measured concurrently. In a further embodiment, the molecular flux rates are measured using stable isotope-labeling techniques. The stable isotope label may include specific heavy isotopes of elements present in biomolecules, such as $^2H$, $^{13}C$, $^{15}N$, $^{18}O$, $^{33}S$, $^{34}S$. In another embodiment, the molecular flux rates are measured using radioactive isotope-labeling techniques. The radioactive isotope label may include $^3H$, $^{14}C$, $^{35}S$, $^{125}I$, $^{131}I$.

Isotope-labeled precursors include, but are not limited to, $^2H_2O$, $H_2{}^{18}O$, $^3H_2O$, $^{15}NH_3$, $^{13}CO_2$, $H^{13}CO_3$, $^2H$-labeled amino acids, $^{13}C$-labeled amino acids, $^{15}N$-labeled amino acids, $^{18}O$-labeled amino acids, $^{34}S$ or $^{33}S$-labeled amino acids, $^3H$-labeled amino acids, and $^{14}C$-labeled amino acids.

The isotope substrate may be chosen from $^2H_2O$, $^2H$-glucose, $^2H$-labeled amino acids, $^{13}C$-labeled amino acids, $^2H$-labeled organic molecules, $^{13}C$-labeled organic molecules, and $^{15}N$-labeled organic molecules labeled water. The isotope substrate may be labeled water, for example, $^2H_2O$, $H_2{}^{18}O$, or $^3H_2O$. The labeled water may be $^2H_2O$.

Stable isotope-labeled substrates are incorporated into one or more molecules of one or more metabolic pathways of interest. In this manner, the molecular flux rates can be determined by measuring, over specific time intervals, isotopic content and/or pattern or rate of change of isotopic content and/or pattern in the targeted molecules, for example by using mass spectrometry, allowing for the determination of the molecular flux rates within the one or more metabolic pathways of interest, by use of analytic and calculation methods known in the art.

Alternatively, the use of radiolabeled substrates is contemplated for use in the present invention wherein the radiolabeled substrates are incorporated into one or more molecules of one or more metabolic pathways of interest. In this manner, the molecular flux rates can be determined by measuring radiation and/or radioactivity of the targeted molecules of interest within the one or more metabolic pathways of interest by using techniques well known in the art such as scintillation counting. The molecular flux rates within the one or more metabolic pathways of interest are then calculated, using methods known in the art.

In another embodiment of the invention, isolated isotopically perturbed molecules are provided, the isotopically perturbed molecules including one or more isotopes. The isolated isotopically perturbed molecules are products of the labeling methods described herein. The isolated isotopically perturbed molecules are collected by sampling techniques known in the art and are analyzed using appropriate analytical tools. In one embodiment of the invention, the isolated isotopically perturbed molecules are comprised of one or more stable isotopes. In another embodiment, the isolated isotopically perturbed molecules are comprised of one or more radioactive isotopes.

In yet another embodiment of the invention, one or more kits are provided that comprise isotope-labeled precursors and instructions for using them. The kits may contain stable-isotope labeled precursors or radioactive-labeled isotope precursors or both. Stable-isotope labeled precursors and radioactive-labeled isotope precursors may be provided in one kit or they may be separated and provided in two or more kits. The kits may further comprise one or more tools for administering the isotope-labeled precursors. The kits also may comprise one or more tools for collecting samples from a subject.

In yet another embodiment of the invention, one or more information storage devices are provided that comprise data generated from the methods of the present invention. The data may be analyzed, partially analyzed, or unanalyzed. The data may be imprinted onto paper, plastic, magnetic, optical, or other medium for storage and display.

In yet another embodiment of the invention, one or more compounds, combinations of compounds, or mixtures of compounds identified and at least partially characterized by the methods of the present invention are contemplated.

BRIEF DESCRIPTION OF THE DRAWINGS

FIG. 1 shows a schematic diagram illustrating the contemporary model of drug discovery (testing for an intended action) versus a strategy of testing for unintended actions.

FIG. 2 shows a schematic diagram illustrating the method of screening for new indications of approved drugs.

FIG. 3 shows a schematic diagram of an example metabolic pathway (DNA synthesis, both de novo and salvage) and various component elements. Locations of stable or radioactive isotope labeling are shown. G6P=Glucose-6-phosphate. R5P=ribose-5-phosphate. PRPP=5-phosphoribosyl-α-pyrophospate. NDP=nucleotide diphosphate. dNTP=deoxynucleotide triphosphate. RR=ribonucleotide reductase. dN=deoxynucleotide. $^3$H-dT=tritiated deoxythymidine. BrdU=5-bromo-2-deoxyuridine. GNG=gluconeogenesis. DNNS=de novo nucleotide synthesis. DNPS=de novo precursor synthesis.

FIG. 4 depicts the fractional replacement (turnover) of murine neurons in vivo. Neurons were isolated from mice concurrently treated with intraperitoneal lipopolysaccharide (LPS) a known neuroinflammatory stimulus, and deuterated water for 45 days. Fractional replacement of neurons was determined by GC/MS analysis of DNA from isolated neurons. Both doses of LPS resulted in a statistically significant increase in neuron turnover with respect to control ($p<0.05$), and statistically significant dose dependence was also observed ($p<0.05$).

FIG. 5 shows a decrease in adipocyte proliferation (i.e., fat cell proliferation) in ob/ob mice after treatment with leptin.

FIG. 6 shows mouse liver cell proliferation during griseofulvin administration (a=control, b=0.1% dose, c=0.2% dose, and d=0.5% dose, 5 days exposure).

FIG. 7 depicts a decrease in mammary epithelial cell proliferation in both intact female rats and ovariectomized rats after treatment with very low doses of selective estrogen receptor modulators (tamoxifen and raloxifene).

FIG. 8a shows that the addition of rosiglitazone to a high carbohydrate (HC) diet significantly increased n in the epididymal and inguinal adipose depots after 26 days of diet and 15 days of $^2$H$_2$O. FIG. 8b shows that by 75 days of diet, n was significantly higher in all adipose depots in the rosiglitazone group.

DETAILED DESCRIPTION OF THE INVENTION

The present invention is directed to methods of detecting actions, particularly unintended or unanticipated actions, of compounds, combinations of compounds, or mixtures of compounds (e.g., new chemical entities, known drug agents including already-approved small molecular entities, new biological factors, or known biological factors including already-approved biological factors), in living systems by measuring molecular flux rates (i.e., synthesis and breakdown or input and removal rates) within metabolic pathways of interest. Molecular flux rates within targeted metabolic pathways are used as biomarkers for establishing and quantifying the actions of compounds. An isotope-labeled substrate molecule is administered or contacted to one or more cells, tissues, or organisms of a living system (i.e., exposing the one or more cells, tissues, or organisms to the isotope-labeled substrate molecule, thereby constituting exposure to said one or more cells, tissues, or organisms). The isotopic content and/or pattern or rate of change of isotopic content and/or pattern of one or more targeted molecules within one or more metabolic pathways of interest is then measured, optimally by use of mass spectrometry, to determine molecular flux rates within the one or more metabolic pathways of interest.

A compound, combination of compounds, or mixture of compounds is also administered or contacted to one or more cells, tissues, or organisms. The molecular flux rates through one or more pathways of interest in the one or more cells, tissues, or organisms are then measured and compared with molecular flux rates through the pathways in one or more cells, tissues, or organisms not exposed to the compound, combination of compounds, or mixture of compounds. Combinations or mixtures of compounds including combinations or mixtures of known drug agents (including small molecule agents and biological factors) are tested for their effects on molecular flux rates through pathways of interest, to identify and quantify synergistic or antagonistic actions of specific combinations. In this manner, a systematic, high-throughput method for identifying unintended actions or confirming biological importance of compounds or combinations of compounds is provided thereby overcoming current limitations of DDDA that only measure a single, intended molecular action of a compound. Thus, the Applicant has discovered methods allowing for drug effects (unanticipated or unintended or confirming biological importance) to be measured on any fully assembled biological system (i.e., the ability to measure molecular flux rates in multiple metabolic pathways, both concurrently and independently, in living systems).

The methods of the present invention allow for high-throughput screening of compounds, combinations of compounds, or mixtures of compounds thereby allowing for the systematic discovery of secondary or unanticipated actions of entire classes of therapeutic agents that were developed or approved for other actions (i.e., thereby providing a method for "mining" the Physicians Desk Reference or Merck Index for new uses of known drugs or agents, a process that is referred to as "drug repositioning" or "drug repurposing"). The methods of the present invention also allow for the discovery of unanticipated toxic effects of compounds, combinations of compounds, or mixtures of compounds.

The invention has applications in drug discovery, development and approval as well as in subsequent medical diagnostics, clinical management of patients and disease prevention.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Cabs, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); and Mass isotopomer distribution analysis at eight years: theoretical, analytic and experimental considerations by Hellerstein and Neese (Am J Physiol 276 (Endocrinol Metab. 39) E1145-E1162, 1999). Furthermore, procedures employing commercially available assay kits and reagents will typically be used according to manufacturer-defined protocols unless otherwise noted.

II. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, Mass isotopomer distribution analysis at eight years: theoretical, analytic and experimental considerations by Hellerstein and Neese (Am J Physiol 276 (Endocrinol Metab. 39) E1146-E1162, 1999). As appropriate, procedures involving the use of commercially available kits and reagents are generally carried out in accordance with manufacturer defined protocols and/or parameters unless otherwise noted.

"Molecular flux rates" refers to the rate of synthesis and/or breakdown of molecules within a cell, tissue, or organism. "Molecular flux rates" also refers to a molecule's input into or removal from a pool of molecules, and is therefore synonymous with the flow into and out of said pool of molecules.

"Metabolic pathway" refers to any linked series of two or more biochemical steps in a living system, the net result of which is a chemical, spatial or physical transformation of a molecule or molecules. Metabolic pathways are defined by the direction and flow of molecules through the biochemical steps that comprise the pathway. Molecules within metabolic pathways can be of any biochemical class, e.g., including but not limited to lipids, proteins, amino acids, carbohydrates, nucleic acids, polynucleotides, porphyrins, glycosaminoglycans, glycolipids, intermediary metabolites, inorganic minerals, ions, etc.

"Flux rate through a metabolic pathway" refers to the rate of molecular transformations through a defined metabolic pathway. The unit of flux rates through pathways is chemical mass per time (e.g., moles per minute, grams per hour). Flux rate through a metabolic pathway optimally refers to the transformation rate from a clearly defined biochemical starting point to a clearly defined biochemical end-point, including all the stages in between in the defined metabolic pathway of interest.

"Isotopes" refer to atoms with the same number of protons and hence of the same element but with different numbers of neutrons (e.g., $^1$H vs. $^2$H or D).

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition, therefore each isotopologue has a unique exact mass but may not have a unique structure. An isotopologue is usually comprised of a family of isotopic isomers (isotopomers) which differ by the location of the isotopes on the molecule (e.g., $CH_3NHD$ and $CH_2DNH_2$ are the same isotopologue but are different isotopomers).

"Isotope-labeled water" or "heavy water" includes water labeled with one or more specific heavy isotopes of either hydrogen or oxygen. Specific examples of isotope-labeled water include $^2H_2O$, $^3H_2O$, and $H_2^{18}O$.

"Action" includes any biological process or event induced in a living system by a compound.

"Unanticipated or unintended action" includes any biological process or event induced in a living system by a compound that was not previously used as an outcome measure in the design or development of the compound (e.g., in a high-throughput screening assay of an enzyme target, in a computer-simulated model of an enzyme's active site, or in an in vivo physiologic model of an altered process); and therefore has not been explicitly predicted on a rational basis, from compelling biochemical evidence, and is not taught as an action to expect from exposure to a particular compound.

"Compound" is used herein to describe any composition of matter including a chemical entity or a biological factor that is administered, approved or under testing as potential therapeutic agent or is a known therapeutic agent. Thus the term encompasses chemical entities and biological factors as defined, infra.

"Chemical entity" includes any chemical, whether new (i.e., a "new chemical entity" or NCE) or known (e.g., a small molecule drug lead or small molecule already-approved drug), that is administered to one or more cells, tissues, or organisms for the purpose of screening it for biological or biochemical activity toward the goal of discovering its use as a potential therapeutic agent[s] (drug[s])).

"Biological factor" as used herein means any compound made by a living system that is administered to one or more cells, tissues, or organisms for the purpose of screening it for biological or biochemical activity toward the goal of discovering its use as a potential therapeutic agent[s] (drug[s])). Examples of biological factors include, but are not limited to, antibodies, hormones, enzymes, enzyme cofactors, peptides, secreted proteins, intracellular proteins, membrane-bound proteins, lipids, phospholipids, carbohydrates, fatty acids, amino acids, nucleic acids (including deoxyribonucleic acids and ribonucleic acids), steroids, and the like. Biological factors also include those compounds made by a living system that have been subsequently altered, modified, or optimized, for example, by way of laboratory techniques.

"Drug leads" or "drug candidates" are herein defined as compounds that are being evaluated, either preclinically or clinically, as potential therapeutic agents (drugs).

"Known drugs" or "known agents" refers to compounds that have been approved for therapeutic use as drugs in human beings or animals in the United States.

By "high-throughput screening" is meant the rapid and efficient screening of large numbers of compounds for potential actions.

"Living system" includes, but is not limited to, cells, cell lines, tissues, animal models of disease, guinea pigs, rabbits, dogs, cats, other pet animals, mice, rats, non-human primates, and humans.

A "biological sample" encompasses any sample obtained from a cell, tissue, organism, or individual. The definition encompasses blood and other liquid samples of biological origin, that are accessible from an organism through sampling by invasive means (e.g., surgery, open biopsy, endoscopic biopsy, and other procedures involving non-negligible risk) or by minimally invasive or non-invasive approaches (e.g., urine collection, blood drawing, needle aspiration, and other procedures involving minimal risk, discomfort or effort). The definition also includes samples that have been manipulated in any way after their procurement, such as by treatment with reagents, solubilization, or enrichment for certain components, such as proteins or organic metabolites. The term "biological sample" also encompasses a clinical sample such as serum, plasma, other biological fluid, or tissue samples, and also includes cells in culture, cell supernatants and cell lysates.

"Biological fluid" refers, but is not limited to, urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, intestinal secretions, or other biological fluid.

"Exact mass" refers to mass calculated by summing the exact masses of all the isotopes in the formula of a molecule (e.g., 32.04847 for $CH_3NHD$).

"Nominal mass" refers to the integer mass obtained by rounding the exact mass of a molecule.

"Mass isotopomer" refers to family of isotopic isomers that is grouped on the basis of nominal mass rather than isotopic composition. A mass isotopomer may comprise molecules of different isotopic compositions, unlike an isotopologue (e.g., $CH_3NHD$, $^{13}CH_3NH_2$, $CH_3{}^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3{}^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^1H$, $^{16}O$, $^{14}N$, etc. Other mass isotopomers are distinguished by their mass differences from $M_0$ ($M_1$, $M_2$, etc.). For a given mass isotopomer, the location or position of isotopes within the molecule is not specified and may vary (i.e., "positional isotopomers" are not distinguished).

"Mass isotopomer envelope" refers to the set of mass isotopomers comprising the family associated with each molecule or ion fragment monitored.

"Isotopic content" refers to the content of isotopes in a molecule or population of molecules relative to the content in the molecule or population of molecules naturally (i.e., prior to administration or contacting of isotope labeled precursor subunits). The term "isotope enrichment" is used interchangeably with isotopic content herein.

"Isotopic pattern" refers to the internal relationships of isotopic labels within a molecule or population of molecules, e.g., the relative proportions of molecular species with different isotopic content, the relative proportions of molecules with isotopic labels in different chemical loci within the molecular structure, or other aspects of the internal pattern rather than absolute content of isotopes in the molecule.

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is said to be 100%. The preferred form for applications involving probability analysis, such as mass isotopomer distribution analysis (MIDA), however, is proportion or fractional abundance, where the fraction that each species contributes to the total abundance is used. The term "isotope pattern" may be used synonomously with the term "mass isotopomer pattern."

"Monoisotopic mass" refers to the exact mass of the molecular species that contains all $^1H$, $^{12}C$, $^{14}N$, $^{16}O$, $^{32}S$, etc. For isotopologues composed of C, H, N, O, P, S, F, Cl, Br, and I, the isotopic composition of the isotopologue with the lowest mass is unique and unambiguous because the most abundant isotopes of these elements are also the lowest in mass. The monoisotopic mass is abbreviated as $m_0$ and the masses of other mass isotopomers are identified by their mass differences from $m_0$ ($m_1$, $m_2$, etc.).

"Isotopically perturbed" refers to the state of an element or molecule that results from the explicit incorporation of an element or molecule with a distribution of isotopes that differs from the distribution that is most commonly found in nature, whether a naturally less abundant isotope is present in excess (enriched) or in deficit (depleted).

By "molecule of interest" is meant any molecule (polymer and/or monomer), including but not limited to, amino acids, carbohydrates, fatty acids, peptides, sugars, lipids, nucleic acids, polynucleotides, glycosaminoglycans, polypeptides, or proteins that are present within a metabolic pathway within a living system.

"Monomer" refers to a chemical unit that combines during the synthesis of a polymer and which is present two or more times in the polymer.

"Polymer" refers to a molecule synthesized from and containing two or more repeats of a monomer.

"Protein" refers to a polymer of amino acids. As used herein, a "protein" may refer to long amino acid polymers as well as short polymers such as peptides.

By "amino acid" is meant any amphoteric organic acid containing the amino group (i.e., $NH_2$). The term encompasses the twenty common (often referred in the art as "standard" or sometimes as "naturally occurring") amino acids as well as the less common (often referred in the art as "nonstandard") amino acids. Examples of the twenty common amino acids include the alpha-amino acids (or cramino acids), which have the amino group in the alpha position, and generally have the formula $RCH—(NH_2)—COOH$. The α-amino acids are the monomeric building blocks of proteins and can be obtained from proteins through hydrolysis. Examples of nonstandard amino acids include, but are not limited to γ-aminobutyric acid, dopamine, histamine, thyroxine, citrulline, ornithine, homocysteine, and S-adenosylmethionine.

"Lipid" refers to any of a heterogeneous group of fats and fatlike substances characterized by being water insoluble and being extractable by nonpolar (or organic) solvents such as alcohol, ether, chloroform, benzene, etc. All contain as a major constituent aliphatic hydrocarbons. The lipids, which are easily stored in the body, serve as a source of fuel, are an important constituent of cell structure, and serve other biological functions. Lipids include, but are not limited to fatty acids, neutral fats (e.g., triacylglycerols), waxes and steroids (e.g., cholesterol). Complex lipids comprise the glycolipids, lipoproteins and phospholipids.

"Fatty acids" are carboxylic acids with long-chain hydrocarbon side groups. They are comprised of organic, monobasic acids, which are derived from hydrocarbons by the equivalent of oxidation of a methyl group to an alcohol, aldehyde, and then acid. Fatty acids can be either saturated or unsaturated.

By "DNA" is meant a polymeric form of deoxyribonucleotides (adenine, guanine, thymine, or cytosine) in double-stranded or single-stranded form, either relaxed or supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. The term captures molecules that include the four bases adenine, guanine, thymine, or cytosine, as well as molecules that include base analogs which are known in the art.

A "nucleic acid" sequence refers to a DNA or RNA sequence. The term captures sequences that include any of the known base analogues of DNA and RNA such as, but not limited to 4-acetylcytosine, 8-hydroxy-$N^6$-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, beta-D-mannosylqueosine, 5-methoxycarbonylmethyluracil, 5-methoxyuracil, 2-methylthio-$N^6$-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

By "carbohydrate" is meant any compound of carbon, oxygen and hydrogen, of general formula $Cx(H_2O)y$, including sugars (monosaccharides and disaccharides) and their derivatives, and polysaccharides such as starch and cellulose.

By "sugar" is meant the common name for any sweet, crystalline, simple carbohydrate that is an aldehyde or ketone derivative of a polyhydric alcohol. Sugars are mainly disaccharides like sucrose and monosaccharides like fructose or glucose; all are soluble in dilute alcohol or water and are white in their pure form. The term encompasses monosaccharides, disaccharides, trisaccharides, heterosaccharides, or polysaccharides (which are comprised of monosaccharide residues). Monosaccharides include glucose (both D-glucose and L-glucose), mannose, fructose galactose and sugar derivatives including, but not limited to N-acetylmuramic acid, N-acetylneuraminic acid and other sialic acids, N-acetylmannosamine, glucuronic acid, glucosamine, etc. Polysaccharides include disaccharides such as sucrose, maltose and lactose and longer chain sugar molecules such as starch, glycogen, cellulose, chitin, etc. By the term "oligosaccharide" is meant a molecule comprised of a few covalently linked monosaccharide monomers.

By "glycosaminoglycan" is meant a polymer comprised of a network of long, unbranched chains made up of repeating units of disaccharides that contain amino group sugars, at least one of which has a negatively charged side group (carboxylate or sulfate). Examples of glycosaminoglycans include, but are not limited to hyaluronate (D-glucuronic acid-N-acetyl-D-glucosamine: MW up to 10 million), chondroitin sulfate (D-glucuronic acid-N-acetyl-D-galactosamine-4 or 6-sulfate), dermatan sulfate (D-glucuronic acid or L-iduronic acid-N-acetyl-D-galactosamine), keratan sulfate (D-galactose-N-acetyl-D-glucosamine sulfate), and heparan sulfate (D-glucuronic acid or L-iduronic acid-N-acetyl-D-glucosamine). "Mucopolysaccharide" is a term that is synonymous with glycosaminoglycan.

By "glycoprotein" is meant a protein or polypeptide that is covalently linked to one or more carbohydrate molecules. Glycoproteins include proteoglycans and many, if not most, of the important integral membrane proteins protruding through the exterior leaflet into the extracellular space, as well as many, if not most, of the secreted proteins.

By "proteoglycan" is meant any of a diverse group of macromolecules comprising proteins and glycosaminoglycans. "Mucoprotein" is a term that is synonymous with proteoglycan.

"Isotope labeled substrate" includes any isotope-labeled precursor molecule that is able to be incorporated into a molecule of interest in a living system. Examples of isotope labeled substrates include, but are not limited to, $^2H_2O$, $^3H_2O$, $H_2^{18}O$, $^2H$-glucose, $^2H$-labeled amino acids, $^3H$-labeled amino acids, $^2H$-labeled organic molecules, $^3H$-labeled organic molecules, $^{13}C$-labeled organic molecules, $^{14}C$-labeled organic molecules, $^{13}CO_2$, $^{14}CO_2$, $^{15}N$-labeled organic molecules and $^{15}NH_3$.

"Labeled sugar" refers to a sugar incorporating one or more stable or radioactive isotopes. As used herein, the term "labeled sugar" is used interchangeably with "isotopically labeled sugar."

"Labeled fatty acid" refers to a fatty acid incorporating one or more stable or radioactive isotopes. As used herein, the term "labeled fatty acid" is used interchangeably with "isotopically labeled fatty acid."

"Labeled Water" or "heavy water" includes water labeled with one or more specific heavy isotopes of either hydrogen or oxygen. Specific examples of labeled water include, but are not limited to, $^2H_2O$, $^3H_2O$, and $H_2^{18}O$. As used herein, the term "labeled water" is used interchangeably with "isotopically labeled water."

"Deuterated water" refers to water incorporating one or more $^2H$ isotopes.

"Labeled glucose" refers to glucose labeled with one or more stable or radioactive isotopes. Specific examples of labeled glucose or $^2H$-labeled glucose include, but are not limited to, [6,6-$^2H_2$]glucose, [1-$^2H_1$]glucose, and [1,2,3,4,5,6-$^2H_7$]glucose.

"Administer[ed]" includes a living system exposed to a compound, combination of compounds, or mixture of compounds. Such exposure can be from, but is not limited to, topical application, oral ingestion, inhalation, subcutaneous injection, intraperitoneal injection, intravenous injection, and intraarterial injection, in animals or other higher organisms.

By "secondary therapeutic action" is meant a biological response to a compound, combination of compounds, or mixture of compounds that was unanticipated or unexpected. Often, the biological response to a compound has been previously established or was explicitly predicted or can be reasonably predicted from empirical data or other sources of information, or was used as the basis to discover and/or develop the compound. In the context of the present invention, a secondary therapeutic action is one that was not explicitly established or predicted or cannot be clearly predicted from pre-existing empirical data or other sources of information. Such a secondary therapeutic action may constitute a "new use" or "new indication" of the compound when another therapeutic action has been previously detected or established.

By "toxic effect" is meant an adverse response by a living system to a compound. In the context of the present invention, a toxic effect is one that is unanticipated or unexpected in response to a compound and that might affect the therapeutic use and/or potential use of the compound.

An "individual" is a vertebrate, preferably a mammal, more preferably a human.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

"At least partially identified" in the context of drug discovery and development means at least one clinically relevant pharmacological characteristic of a compound has been identified using one or more of the methods of the present invention. This characteristic may be a desirable one, for example, increasing or decreasing molecular flux rates through a metabolic pathway that contributes to a disease process, altering signal transduction pathways or cell surface receptors that alter the activity of metabolic pathways relevant to a disease, inhibiting activation of an enzyme and the like. Alternatively, a pharmacological characteristic of a compound may be an undesirable one for example, the production of one or more toxic effects. There are a plethora of desirable and undesirable characteristics of compounds well known to those skilled in the art and each will be viewed in the context of the particular compound being developed and the targeted disease. Of course, a compound can be more than at least partially identified, for example, when several characteristics have been identified (desirable or undesirable or both) that are sufficient to support a particular milestone decision point along the drug development pathway. Such milestones include, but are not limited to, pre-clinical decisions for in vitro to in vivo transition, pre-IND filing go/no go decision, phase I to phase II transition, phase IIa to phase IIb transition, phase II to phase III transition, NDA filing, and FDA approval for marketing. Therefore, "at least partially" identified includes the identification of one or more pharmacological characteristics useful in evaluating a compound in the drug discovery/drug development process. A pharmacologist or physician or other researcher may evaluate all or a portion of the identified desirable and undesirable characteristics of a compound to establish its therapeutic index. This may be accomplished using procedures well known in the art.

"Manufacturing compounds" in the context of the present invention includes any means, well known to those skilled in the art, employed for the making of a compound as a product. A product is not limited to a final approved therapeutic agent but may constitute a non-final compound in the DDDA process, e.g., a prodrug or chemical intermediary (i.e., a lead compound that has been out-licensed for further optimization), whose manufacture is in response to a commercial need. Manufacturing processes include, but are not limited to, medicinal chemical synthesis (i.e., synthetic organic chemistry), combinatorial chemistry, biotechnology methods such as hybridoma monoclonal antibody production, recombinant DNA technology, and other techniques well known to the skilled artisan. Such a product may be a final drug agent that is marketed for therapeutic use, a component of a combination product that is marketed for therapeutic use, or any intermediate product used in the development of the final drug agent product, whether as part of a combination product or a single product.

III. Methods of the Invention

The present invention is directed to methods of detecting actions, particularly unintended or unexpected actions, of compounds in living systems by measuring the molecular flux rates of one or more molecules in one or more metabolic pathways of interest within a living system. First, at least one isotope-labeled substrate molecule is administered to one or more cells, tissues or organisms for a period of time sufficient to be incorporated in vivo into one or more targeted molecules of interest within one or more targeted metabolic pathways. In one embodiment, the isotope-labeled substrate molecules are labeled with one or more stable isotopes (i.e., non-radioactive isotope). In another embodiment, the isotope-labeled substrate molecule is labeled with one or more radioactive isotopes. In yet another embodiment, both stable and radioactive isotopes are used to label one or more isotope-labeled substrate molecules.

The targeted molecule of interest is obtained by biochemical isolation procedures from the one or more cells, tissues, or organisms, and is identified by mass spectrometry, liquid scintillation, or by other means known in the art. The relative and absolute abundances of the ions within the mass isotopomeric envelope corresponding to each identified molecule of interest (i.e., the isotopic content and/or pattern of the molecule or the rate of change of the isotopic content and/or pattern of the molecule) are quantified. In one embodiment, the relative and absolute abundances of the ions within the mass isotopomeric envelope corresponding to each identified molecule of interest are quantified by mass spectrometry. Molecular flux rates through the targeted metabolic pathways of interest are then calculated by use of equations known in the art and discussed, infra. Molecular flux rates through the targeted metabolic pathways of interest are compared in the presence or absence of exposure to one or more compounds, combinations of compounds, or mixtures of compounds, or in response to different levels of exposure to compounds, or in response to different levels of exposure to combinations of compounds or mixtures of compounds.

A. Administering Isotope-Labeled Precursor(s)

As a first step in the methods of the invention, isotope-labeled precursors are administered.

1. Administering an Isotope-Labeled Precursor Molecule

Modes of administering the one or more isotope-labeled substrates may vary, depending upon the absorptive properties of the isotope-labeled substrate and the specific biosynthetic pool into which each compound is targeted. Precursors may be administered to organisms, plants and animals including humans directly for in vivo analysis. In addition, precursors may be administered in vitro to living cells or ex vivo in tissues or organs. Specific types of living cells include hepatocytes, adipocytes, myocytes, fibroblasts, neurons, pancreatic β-cells, intestinal epithelial cells, leukocytes, lymphocytes, erythrocytes, microbial cells and any other cell-type that can be maintained alive and functional in vitro.

Generally, an appropriate mode of administration is one that produces a steady state level of precursor within the biosynthetic pool and/or in a reservoir supplying such a pool for at least a transient period of time. Intravascular or oral routes of administration are commonly used to administer such precursors to organisms, including humans. Other routes of administration, such as subcutaneous or intra-muscular administration, optionally when used in conjunction with slow release precursor compositions, formulations, or techniques, are also appropriate. Compositions for injection are generally prepared in sterile pharmaceutical excipients.

a. Labeled Precursor Molecules (1) Isotope Labels

The first step in measuring molecular flux rates involves administering one or more isotope-labeled precursor molecules to one or more cells, tissues, or organisms. The isotope labeled precursor molecule may contain a stable isotope or a radioisotope. Isotope labels that can be used in accordance with the methods of the present invention include, but are not limited to, $^2H$, $^{13}C$, $^{15}N$, $^{18}O$, $^3H$, $^{14}C$, $^{35}S$, $^{32}P$, $^{125}I$, $^{131}I$, or other isotopes of elements present in organic systems. These isotopes, and others, are suitable for all classes of chemicals (i.e., precursor molecules) envisioned for use in the present invention. Such precursor molecules include, but are not limited to, amino acid precursors, protein precursors, lipid precursors, carbohydrate precursors, nucleic acid precursors, porphyrin precursors, glycosaminoglycan precursors, and proteoglycan precursors (see examples of each, infra).

In one embodiment, the isotope label is $^2H$.

(2) Precursor Molecules (Isotope-Labeled Substrates)

The precursor molecule may be any molecule having an isotope label that is incorporated into a molecule of interest by passage through a metabolic pathway in vivo in a living system. Precursor molecules that may be used include, without limitation: $H_2O$; $CO_2$; $NH_3$; acetyl CoA (to form cholesterol, fatty acids); ribonucleic acids (to form RNA); deoxyribonucleic acids (to form DNA); glucose (to form glycogen); amino acids (to form peptides/proteins); phosphoenol-pyruvate (to form glucose/UDP-glucose); and glycine/succinate (to form porphyrin derivatives). Isotope labels may be used to modify all precursor molecules disclosed herein to form isotope-labeled precursor molecules.

The entire precursor molecule may be incorporated into one or more molecules of interest within a metabolic pathway. Alternatively, a portion of the precursor molecule may be incorporated into one or more molecules of interest.

The individual being administered one or more isotope labeled substrates (i.e., one or more precursor molecules) may be a mammal. In one variation, the mammal may be a rodent (rat or mouse), primate, hamster, guinea pig, dog, or pig. The mammal may be wild-type. In another embodiment, the mammal may be an engineered animal including, but not limited to, a transgenic animal, a gene knock-out animal, or a gene knock-in animal. In one embodiment, the mammal may be healthy. In another embodiment, the mammal may have a disease or medical condition. Mammals having a disease or having a medical condition may have a congenital disease or medical condition or an acquired disease or medical condition. Examples of mammals having either a congenital disease or medical condition or an acquired disease or medical condition are well known to those of skill in the art.

In still another embodiment, the mammal may be a human.

i. Protein Precursors

A protein precursor molecule may be any protein precursor molecule known in the art. These precursor molecules may be amino acids, $CO_2$, $NH_3$, glucose, lactate, $H_2O$, acetate, and fatty acids.

The isotope label may include specific heavy isotopes of elements present in biomolecules, such as $^2H$, $^{13}C$, $^{15}N$, $^{18}O$, $^{33}S$, $^{34}S$, or may contain other isotopes of elements present in biomolecules such as $^3H$, $^{14}C$, $^{35}S$, $^{125}I$, or $^{131}I$.

Precursor molecules of proteins may include one or more amino acids. The precursor may be any amino acid. The precursor molecule may be a singly or multiply deuterated amino acid. The precursor molecule may be one or more of $^{13}C$-lysine, $^{15}N$-histidine, $^{13}C$-serine, $^{13}C$-glycine, $^2H$-leucine, $^{15}N$-glycine, $^{13}C$-leucine, $^2H_5$-histidine, and any deuterated amino acid. By way of example, isotope labeled protein precursors include, but are not limited to $^2H_2O$, $H_2^{18}O$, $^{15}NH_3$, $^{13}CO_2$, $H^{13}CO_3$, $^2H$-labeled amino acids, $^{13}C$ labeled amino acids, $^{15}N$ labeled amino acids, $^{18}O$ labeled amino acids, $^{33}S$ or $^{34}S$ labeled amino acids, $^3H_2O$, $^3H$-labeled amino acids, and $^{14}C$ labeled amino acids. Labeled amino acids may be administered, for example, undiluted or diluted with non-labeled amino acids. All isotope labeled precursors may be purchased commercially, for example, from Cambridge Isotope Labs (Andover, Mass.).

Protein precursor molecules may also include any precursor for post-translational or pre-translationally modified amino acids. These precursors include but are not limited to precursors of methylation such as glycine, serine or $H_2O$; precursors of hydroxylation, such as $H_2O$ or $O_2$; precursors of phosphorylation, such as phosphate, $H_2O$ or $O_2$; precursors of prenylation, such as fatty acids, acetate, $H_2O$, ethanol, ketone bodies, glucose, or fructose; precursors of carboxylation, such as $CO_2$, $O_2$, $H_2O$, or glucose; precursors of acetylation, such as acetate, ethanol, glucose, fructose, lactate, alanine, $H_2O$, $CO_2$, or $O_2$; and other pre or post-translational modifications known in the art.

The degree of labeling present in free amino acids may be determined experimentally, or may be assumed based on the number of labeling sites in an amino acid. For example, when using hydrogen isotopes as a label, the labeling present in C—H bonds of free amino acid or, more specifically, in tRNA-amino acids, during exposure to $^2H_2O$ in body water may be identified. The total number of C—H bonds in each non essential amino acid is known—e.g., 4 in alanine, 2 in glycine, etc.

The precursor molecule for proteins may be water. The hydrogen atoms on C—H bonds are the hydrogen atoms on amino acids that are useful for measuring protein synthesis from $^2H_2O$ since the O—H and N—H bonds of proteins are labile in aqueous solution. As such, the exchange of $^2H$-label from $^2H_2O$ into O—H or N—H bonds occurs without the synthesis of proteins from free amino acids as described above. C—H bonds undergo incorporation from $H_2O$ into free amino acids during specific enzyme-catalyzed intermediary metabolic reactions. The presence of $^2H$-label in C—H bonds of protein-bound amino acids after $^2H_2O$ administration therefore means that the protein was assembled from amino acids that were in the free form during the period of $^2H_2O$ exposure—i.e., that the protein is newly synthesized. Analytically, the amino acid derivative used must contain all the C—H bonds but must remove all potentially contaminating N—H and O—H bonds.

Hydrogen atoms from body water may be incorporated into free amino acids. $^2H$ or $^3H$ from labeled water (i.e., $^2H_2O$ or $^3H_2O$) can enter into free amino acids in the cell through the reactions of intermediary metabolism, but $^2H$ or $^3H$ cannot enter into amino acids that are present in peptide bonds or that are bound to transfer RNA. Free essential amino acids may incorporate a single hydrogen atom from body water into the α-carbon C—H bond, through rapidly reversible transamination reactions. Free non-essential amino acids contain a larger number of metabolically exchangeable C—H bonds, of course, and are therefore expected to exhibit higher isotopic enrichment values per molecule from $^2H_2O$ or $^3H_2O$ in newly synthesized proteins.

One of skill in the art will recognize that labeled hydrogen atoms from body water may be incorporated into other amino acids via other biochemical pathways. For example, it is known in the art that hydrogen atoms from water may be incorporated into glutamate via synthesis of the precursor α-ketoglutarate in the citric acid cycle. Glutamate, in turn, is known to be the biochemical precursor for glutamine, proline, and arginine. By way of another example, hydrogen atoms from body water may be incorporated into post-translationally modified amino acids, such as the methyl group in 3-methyl-histidine, the hydroxyl group in hydroxyproline or hydroxylysine, and others. Other amino acid synthesis pathways are known to those of skill in the art.

Oxygen atoms ($H_2^{18}O$) may also be incorporated into amino acids through enzyme-catalyzed reactions. For example, oxygen exchange into the carboxylic acid moiety of amino acids may occur during enzyme catalyzed reactions. Incorporation of labeled oxygen into amino acids is known to one of skill in the art. Oxygen atoms may also be incorporated into amino acids from $^{18}O_2$ through enzyme catalyzed reactions (including hydroxyproline, hydroxylysine or other post-translationally modified amino acids).

Hydrogen and oxygen labels from labeled water may also be incorporated into amino acids through post-translational modifications. In one embodiment, the post-translational modification may already include labeled hydrogen or oxygen through biosynthetic pathways prior to post-translational modification. In another embodiment, the post-translational modification may incorporate labeled hydrogen, oxygen, carbon, or nitrogen from metabolic derivatives involved in the free exchange labeled hydrogens from body water, either before or after a post-translational modification step (e.g., methylation, hydroxylation, phosphorylation, prenylation, sulfation, carboxylation, acetylation or other known post-translational modifications).

Protein precursors that are suitable for administration into a subject include, but are not limited to $H_2O$, $CO_2$, $NH_3$ and $HCO_3$, in addition to the standard amino acids found in proteins.

The individual being administered protein precursors may be a mammal. In one variation, the mammal may be a rodent (rat or mouse), primate, hamster, guinea pig, dog, or pig. The mammal may be wild-type. In another embodiment, the mammal may be an engineered animal including, but not limited to, a transgenic animal, a gene knock-out animal, or a gene knock-in animal. In one embodiment, the mammal may be healthy. In another embodiment, the mammal may have a disease or medical condition. Mammals having a disease or having a medical condition may have a congenital disease or medical condition or an acquired disease or medical condition. Examples of mammals having either a congenital disease or medical condition or an acquired disease or medical condition are well known to those of skill in the art.

In still another embodiment, the mammal may be a human.

ii. Precursors of Organic Metabolites

Precursors of organic metabolites may be any precursor molecule capable of entering into the organic metabolite pathway. Organic metabolites and organic metabolite precursors include, but are not limited to, $H_2O$, $CO_2$, $NH_3$, $HCO_3$, amino acids, monosaccharides, carbohydrates, lipids, fatty acids, nucleic acids, glycolytic intermediates, acetic acid, and tricarboxylic acid cycle intermediates.

Isotope labeled organic metabolite precursors include, but are not limited to, $^2H_2O$, $^{15}NH_3$, $^{13}CO_2$, $H^{13}CO_3$, $^2H$-labeled amino acids, $^{13}C$-labeled amino acids, $^{15}N$-labeled amino acids, $H_2^{18}O$, $^{18}O$-labeled amino acids, $^{33}S$ or $^{34}S$-labeled amino acids, $^3H_2O$, $^3H$-labeled amino acids, $^{14}C$-labeled amino acids, $^{14}CO_2$, and $H^{14}CO_2$.

Organic metabolite precursors may also be administered directly. Mass isotopes that may be useful in mass isotope labeling of organic metabolite precursors include, but are not limited to, $^2H$, $^3H$, $^{13}C$, $^{14}C$, $^{15}N$, $^{18}O$, $^{33}S$, $^{34}S$, $^{35}S$, $^{32}P$, $^{125}I$, $^{131}I$, or other isotopes of elements present in organic systems. It is often desirable, in order to avoid metabolic loss of isotope labels, that the isotope-labeled atom(s) be relatively non-labile or at least behave in a predictable manner within the subject. By administering the isotope-labeled precursors to the biosynthetic pool, the isotope-labeled precursors can become directly incorporated into organic metabolites formed in the pool.

The individual being administered organic metabolite precursors may be a mammal. In one variation, the mammal may be a rodent (rat or mouse), primate, hamster, guinea pig, dog, or pig. The mammal may be wild-type. In another embodiment, the mammal may be an engineered animal including, but not limited to, a transgenic animal, a gene knock-out animal, or a gene knock-in animal. In one embodiment, the mammal may be healthy. In another embodiment, the mammal may have a disease or medical condition. Mammals having a disease or having a medical condition may have a congenital disease or medical condition or an acquired disease or medical condition. Examples of mammals having either a congenital disease or medical condition or an acquired disease or medical condition are well known to those of skill in the art.

In still another embodiment, the mammal may be a human.

iii. Precursors of Nucleic Acids

Precursors of nucleic acids (i.e., RNA, DNA) are any substrates suitable for incorporation into RNA and/or DNA synthetic pathways. Examples of substrates useful in labeling the deoxyribose ring of DNA include, but are not limited to, [6,6-$^2H_2$] glucose, [U-$^{13}C_6$] glucose and [2-$^{13}C_1$] glycerol (see U.S. Pat. No. 6,461,806, herein incorporated by reference). Labeling of the deoxyribose is superior to labeling of the information-carrying nitrogen bases in DNA because it avoids variable dilution sources. The stable isotope labels are readily detectable by mass spectrometric techniques.

In one embodiment, a stable isotope label is used to label the deoxyribose ring of DNA from glucose, precursors of glucose-6-phosphate or precursors of ribose-5-phosphate. In embodiments where glucose is used as the starting material, suitable labels include, but are not limited to, deuterium-labeled glucose such as [6,6-$^2H_2$] glucose, [1-$^2H_1$] glucose, [3-$^2H_1$] glucose, [$^2H_7$] glucose, and the like; $^{13}C$-1 labeled glucose such as [1-$^{13}C_1$] glucose, [U-$^{13}C_6$] glucose and the like; and $^{18}O$-labeled glucose such as [1-$^{18}O_2$] glucose and the like.

In embodiments where a glucose-6-phosphate precursor or a ribose-5-phosphate precursor is desired, a gluconeogenic precursor or a metabolite capable of being converted to glucose-6-phosphate or ribose-5-phosphate can be used. Gluconeogenic precursors include, but are not limited to, $^{13}C$-labeled glycerol such as [2-$^{13}C_1$] glycerol and the like, a $^{13}C$-labeled amino acid, deuterated water ($^2H_2O$) and $^{13}C$-labeled lactate, alanine, pyruvate, propionate or other non-amino acid precursors for gluconeogenesis. Metabolites which are converted to glucose-6-phosphate or ribose-5-phosphate include, but are not limited to, labeled ($^2H$ or $^{13}C$) hexoses such as [1-$^2H_1$] galactose, [U-$^{13}C$] fructose and the like; labeled ($^2H$ or $^{13}C$) pentoses such as [1-$^{13}C_1$] ribose, [1-$^2H_1$] xylitol and the like, labeled ($^2H$ or $^{13}C$) pentose phosphate pathway metabolites such as [1-$^2H_1$] seduheptalose and the like, and labeled ($^2H$ or $^{13}C$) amino sugars such as [U-$^{13}C$] glucosamine, [1-$^2H_1$] N-acetyl-glucosamine and the like.

The present invention also encompasses stable isotope labels which label purine and pyrimidine bases of DNA through the de novo nucleotide synthesis pathway. Various building blocks for endogenous purine synthesis can be used to label purines and they include, but are not limited to, $^{15}N$-labeled amino acids such as [$^{15}N$] glycine, [$^{15}N$] glutamine, [$^{15}N$] aspartate and the like, $^{13}C$-labeled precursors such as [1-$^{13}C_1$] glycone, [3-$^{13}C_1$] acetate, [$^{13}C$]HCO$_3$, [$^{13}C$] methionine and the like, and H-labeled precursors such as $^2H_2O$. Various building blocks for endogenous pyrimidine synthesis can be used to label pyrimidines and they include, but are not limited to, $^{15}N$-labeled amino acids such as [$^{15}N$] glutamine and the like, $^{13}C$-labeled precursors such as [$^{13}C$] HCO$_3$, [U-$^{13}C_4$] aspartate and the like, and $^2H$-labeled precursors (e.g., $^2H_2O$).

It is understood by those skilled in the art that in addition to the list above, other stable isotope labels which are substrates or precursors for any pathways which result in endogenous labeling of DNA are also encompassed within the scope of the invention. The labels suitable for use in the present invention are generally commercially available or can be synthesized by methods well known in the art.

The individual being administered nucleic acid precursors may be a mammal. In one variation, the mammal may be a rodent (rat or mouse), primate, hamster, guinea pig, dog, or pig. The mammal may be wild-type. In another embodiment, the mammal may be an engineered animal including, but not limited to, a transgenic animal, a gene knock-out animal, or a gene knock-in animal. In one embodiment, the mammal may be healthy. In another embodiment, the mammal may have a disease or medical condition. Mammals having a disease or having a medical condition may have a congenital disease or medical condition or an acquired disease or medical condition. Examples of mammals having either a congenital disease or medical condition or an acquired disease or medical condition are well known to those of skill in the art.

In still another embodiment, the mammal may be a human.

iv. Water as a Precursor Molecule

Water is a precursor of proteins and many organic metabolites. As such, labeled water may serve as a precursor in the methods taught herein.

H$_2$O availability is probably never limiting for biosynthetic reactions in a cell (because H$_2$O represents close to 70% of the content of cells, or >35 Molar concentration), but hydrogen and oxygen atoms from H$_2$O contribute stoichiometrically to many reactions involved in biosynthetic pathways:

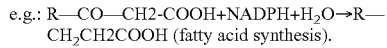

e.g.: R—CO—CH2-COOH+NADPH+H$_2$O→R—CH$_2$CH2COOH (fatty acid synthesis).

As a consequence, isotope labels provided in the form of H- or O-isotope-labeled water is incorporated into biological molecules as part of synthetic pathways. Hydrogen incorporation can occur in two ways: into labile positions in a molecule (i.e., rapidly exchangeable, not requiring enzyme-catalyzed reactions) or into stable positions (i.e., not rapidly exchangeable, requiring enzyme catalysis). Oxygen incorporation occurs in stable positions.

Some of the hydrogen-incorporating steps from cellular water into C—H bonds in biological molecules only occur during well-defined enzyme-catalyzed steps in the biosynthetic reaction sequence, and are not labile (i.e., exchangeable with solvent water in the tissue) once present in the mature end-product molecules. For example, the C—H bonds on glucose are not exchangeable in solution. In contrast, each of the following C—H positions exchanges with body water during reversal of specific enzymatic reactions: C-1 and C-6, in the oxaloacetate/succinate sequence in the Krebs' cycle and in the lactate/pyruvate reaction; C-2, in the glucose-6-phosphate/fructose-6-phosphate reaction; C-3 and C-4, in the glyceraldehyde-3-phosphate/dihydroxyacetone-phosphate reaction; C-5, in the 3-phosphoglycerate/glyceraldehyde-3-phosphate and glucose-6-phosphate/fructose-6-phosphate reactions.

Labeled hydrogen or oxygen atoms from water that are covalently incorporated into specific non-labile positions of a molecule thereby reveals the molecule's "biosynthetic history"—i.e., label incorporation signifies that the molecule was synthesized during the period that isotope-labeled water was present in cellular water.

Conversely, labile hydrogens (non-covalently associated or present in exchangeable covalent bonds) in these biological molecules do not reveal the molecule's biosynthetic history. Labile hydrogen atoms can be easily removed by incubation with unlabelled water (H$_2$O) (i.e., by reversal of the same non-enzymatic exchange reactions through which $^2H$ or $^3H$ was incorporated in the first place), as the following reaction demonstrates:

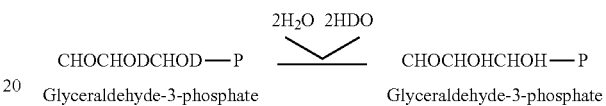

CHOCHODCHOD—P $\xrightleftharpoons[]{2H_2O\ 2HDO}$ CHOCHOHCHOH—P

Glyceraldehyde-3-phosphate      Glyceraldehyde-3-phosphate

As a consequence, a potentially contaminating hydrogen label that does not reflect biosynthetic history, but is incorporated via non-synthetic exchange reactions, can be easily removed in practice by incubation with natural abundance H$_2$O.

Analytic methods are available for measuring quantitatively the incorporation of labeled hydrogen atoms into biological molecules (e.g., liquid scintillation counting for $^3H$; mass spectrometry or NMR spectroscopy for $^2H$ and $^{18}O$). For further discussions on the theory of isotope-labeled water incorporation, see, for example, Jungas R L. *Biochemistry*. 1968 7:3708-17, incorporated herein by reference.

Labeled water may be readily obtained commercially. For example, $^2H_2O$ may be purchased from Cambridge Isotope Labs (Andover, Mass.), and $^3H_2O$ may be purchased, e.g., from New England Nuclear, Inc. In general, $^2H_2O$ is non-radioactive and thus, presents fewer toxicity concerns than radioactive $^3H_2O$. $^2H_2O$ may be administered, for example, as a percent of total body water, e.g., 1% of total body water consumed (e.g., for 3 liters water consumed per day, 30 microliters $^2H_2O$ is consumed). If $^3H_2O$ is utilized, then a non-toxic amount, which is readily determined by those of skill in the art, is administered.

Relatively high body water enrichments of $^2H_2O$ (e.g., 1-10% of the total body water is labeled) may be achieved relatively inexpensively using the techniques of the invention. This water enrichment is relatively constant and stable as these levels are maintained for weeks or months in humans and in experimental animals without any evidence of toxicity. This finding in a large number of human subjects (>100 people) is contrary to previous concerns about vestibular toxicities at high doses of $^2H_2O$. The Applicant has discovered that as long as rapid changes in body water enrichment are prevented (e.g., by initial administration in small, divided doses), high body water enrichments of $^2H_2O$ can be maintained with no toxicities. For example, the low cost of commercially available $^2H_2O$ allows long-term maintenance of enrichments in the 1-5% range at relatively low expense (e.g., calculations reveal a lower cost for 2 months labeling at 2% $^2H_2O$ enrichment, and thus 7-8% enrichment in the alanine precursor pool, than for 12 hours labeling of $^2H$-leucine at 10% free leucine enrichment, and thus 7-8% enrichment in leucine precursor pool for that period).

Relatively high and relatively constant body water enrichments for administration of H$_2^{18}$O may also be accomplished, since the $^{18}O$ isotope is not toxic, and does not present a significant health risk as a result.

Isotope-labeled water may be administered via continuous isotope-labeled water administration, discontinuous isotope-labeled water administration, or after single or multiple administration of isotope-labeled water administration. In continuous isotope-labeled water administration, isotope-labeled water is administered to an individual for a period of time sufficient to maintain relatively constant water enrichments over time in the individual. For continuous methods, labeled water is optimally administered for a period of sufficient duration to achieve a steady state concentration (e.g., 3-8 weeks in humans, 1-2 weeks in rodents).

In discontinuous isotope-labeled water administration, an amount of isotope-labeled water is measured and then administered, one or more times, and then the exposure to isotope-labeled water is discontinued and wash-out of isotope-labeled water from body water pool is allowed to occur. The time course of delabeling may then be monitored. Water is optimally administered for a period of sufficient duration to achieve detectable levels in biological molecules.

Isotope-labeled water may be administered to an individual or tissue in various ways that are well known in the art. For example, isotope-labeled water may be administered orally, parenterally, subcutaneously, intravascularly (e.g., intravenously, intraarterially), or intraperitoneally. Several commercial sources of $^2H_2O$ and $H_2{}^{18}O$ are available, including Isotec, Inc. (Miamisburg Ohio, and Cambridge Isotopes, Inc. (Andover, Mass.). The isotopic content of isotope labeled water that is administered can range from about 0.001% to about 20% and depends upon the analytic sensitivity of the instrument used to measure the isotopic content of the biological molecules. For oral administration, 4% $^2H_2O$ in drinking water is administered. For human administration, 50 mL $H_2O^2$ is administered.

The individual being administered labeled water may be a mammal. In one variation, the mammal may be a rodent (rat or mouse), primate, hamster, guinea pig, dog, or pig. The mammal may be wild-type. In another embodiment, the mammal may be an engineered animal including, but not limited to, a transgenic animal, a gene knock-out animal, or a gene knock-in animal. In one embodiment, the mammal may be healthy. In another embodiment, the mammal may have a disease or medical condition. Mammals having a disease or having a medical condition may have a congenital disease or medical condition or an acquired disease or medical condition. Examples of mammals having either a congenital disease or medical condition or an acquired disease or medical condition are well known to those of skill in the art.

In still another embodiment, the mammal may be a human.

v. Precursors of Carbohydrates

Compositions comprising carbohydrates may include monosaccharides, polysaccharides, or other compounds attached to monosaccharides or polysaccharides.

Isotope labels may be incorporated into carbohydrates or carbohydrate derivatives by biochemical pathways known in the art. These include monosaccharides (including, but not limited to, glucose and galactose), amino sugars (such as N-Acetyl-Galactosamine), polysaccharides (such as glycogen), glycoproteins (such as sialic acid) glycolipids (such as galactocerebrosides), and glycosaminoglycans (such as hyaluronic acid, chondroitin-sulfate, and heparan-sulfate).

$^2H$-labeled sugars may be administered to an individual as monosaccharides or as polymers comprising monosaccharide residues. Labeled monosaccharides may be readily obtained commercially (e.g., Cambridge Isotopes, Massachusetts).

Relatively low quantities of compounds comprising $^2H$-labeled sugars need be administered. Quantities may be on the order of milligrams, $10^1$ mg, $10^2$ mg, $10^3$ mg, $10^4$ mg, $10^5$ mg, or $10^6$ mg. $^2H$-labeled sugar enrichment may be maintained for weeks or months in humans and in animals without any evidence of toxicity. The low cost of commercially available labeled monosaccharides, and low quantity that need to be administered, allow maintenance of enrichments at low expense.

In one embodiment, the labeled sugar is glucose. Glucose is metabolized by glycolysis and the citric acid cycle. Glycolysis releases most of the H-atoms from the C—H bonds of glucose; oxidation via the citric acid cycle ensures that all H-atoms are released to $H_2O$. The loss of $^3H$- or $^2H$-label by glucose has been used to assess glycolysis, an intracellular metabolic pathway for glucose. Some investigators have used release of $^3H$ from intravenously administered $^3H$-glucose into $^3H_2O$ as a measure of glycolysis. Release of $^2H$-glucose into $^2H_2O$ has not been described previously, ostensibly because of the expectation that the body water pool is too large relative to $^2H$ administration in labeled glucose to achieve measurable $^2H_2O$ levels. The Applicant has discovered otherwise, demonstrating that the release of $^2H$-glucose into $^2H_2O$ can be measured (see U.S. patent application Ser. No. 10/701,990, herein incorporated by reference). In a further variation, the labeled glucose may be [6,6-$^2H_2$]glucose, [1-$^2H_1$]glucose, and [1,2,3,4,5,6-$^2H_7$]glucose.

In another variation, labeled sugar comprises fructose or galactose. Fructose enters glycolysis via the fructose 1-phosphate pathway, and secondarily through phosphorylation to fructose 6-phosphate by hexokinase. Galactose enters glycolysis via the galactose to glucose interconversion pathway.

Any other sugar is envisioned by the present invention. Contemplated monosaccharides, include, but are not limited to, trioses, pentoses, hexose, and higher order monosaccharides. Monosaccharides further include, but are not limited to, aldoses and ketoses.

In another variation, compounds comprising polysaccharides may be administered. The polymers may comprise polysaccharides. For example, labeled glycogen, a polysaccharide, comprises glucose residues. In another variation, labeled polysaccharides may be introduced. As further variation, labeled sugar monomers may be administered as a component of sucrose (glucose α-(1,2)-fructose), lactose (galactose β-(1,4)-glucose), maltose (glucose α-(1,4)-glucose), starch (glucose polymer), or other polymers.

In another variation, the labeled sugar may be administered orally, by gavage, intraperitoneally, intravascularly (e.g., intravenously, intraarterially), subcutaneously, or other bodily routes. In particular, the sugars may be administered to an individual orally, optionally as part of a food or drink.

The individual being administered carbohydrate precursors may be a mammal. In one variation, the mammal may be a rodent (rat or mouse), primate, hamster, guinea pig, dog, or pig. The mammal may be wild-type. In another embodiment, the mammal may be an engineered animal including, but not limited to, a transgenic animal, a gene knock-out animal, or a gene knock-in animal. In one embodiment, the mammal may be healthy. In another embodiment, the mammal may have a disease or medical condition. Mammals having a disease or having a medical condition may have a congenital disease or medical condition or an acquired disease or medical condition. Examples of mammals having either a congenital disease or medical condition or an acquired disease or medical condition are well known to those of skill in the art.

In still another embodiment, the mammal may be a human.

vi. Precursors of Lipids and Other Fats

Labeled precursors of lipids may include any precursor in lipid biosynthesis. The precursor molecules of lipids may be $CO_2$, $NH_3$, glucose, lactate, $H_2O$, acetate, and fatty acids. The precursor may also include labeled water, e.g., $^2H_2O$, which is a precursor for fatty acids, glycerol moiety of acyl-glycerols, cholesterol and its derivatives; $^{13}C$ or $^2H$-labeled fatty acids, which are precursors for triglycerides, phospholipids, cholesterol ester, coamides and other lipids; $^{13}C$- or $^2H$-acetate, which is a precursor for fatty acids and cholesterol; $^{18}O_2$ (e.g., g from $H_2^{18}O$), which is a precursor for fatty acids, cholesterol, acyl-glycerides, and certain oxidatively modified fatty acids (such as peroxides) by either enzymatically catalyzed reactions or by non-enzymatic oxidative damage (e.g., to fatty acids); $^{13}C$- or $^2H$-glycerol, which is a precursor for acyl-glycerides; $^{13}C$- or $^2H$-labeled acetate, ethanol, ketone bodies or fatty acids, which are precursors for endogenously synthesized fatty acids, cholesterol and acylglycerides; and $^2H$ or $^{13}C$-labeled cholesterol or its derivatives (including bile acids and steroid hormones). All isotope labeled precursors may be purchased commercially, for example, from Cambridge Isotope Labs (Andover, Mass.).

Complex lipids, such as glycolipids and cerebrosides, can also be labeled from precursors, including $^2H_2O$, which is a precursor for the sugar-moiety of cerebrosides (including, but not limited to, N-acetylgalactosamine, N-acetylglucosamine-sulfate, glucuronic acid, and glucuronic acid-sulfate), the fatty acyl-moiety of cerebrosides and the sphingosine moiety of cerebrosides; $^2H$- or $^{13}C$-labeled fatty acids, which are precursors for the fatty acyl moiety of cerebrosides, glycolipids and other derivatives.

The precursor molecule may be or include components of lipids.

In one embodiment, $^2H$-labeled fatty acids may be administered to an individual as fats or other substrates containing the labeled fatty acids. $^2H$-labeled fatty acids may be readily obtained commercially. Relatively low quantities of labeled fatty acids need be administered. Quantities may be on the order of milligrams, $10^1$ mg, $10^2$ mg, $10^3$ mg, $10^4$ mg, $10^5$ mg, or $10^6$ mg. Fatty acid enrichment, particularly with $^2H$, may be maintained for weeks or months in humans and in animals without any evidence of toxicity. The low cost of commercially available labeled fatty acids, and low quantity that need to be administered, allow maintenance of enrichments at low expense.

The release of labeled fatty acids, particularly $^2H$-fatty acid, to labeled water, particularly $^2H_2O$, accurately reflects fat oxidation. Administration of modest amounts of labeled-fatty acid is sufficient to measure release of labeled hydrogen or oxygen to water. In particular, administration of modest amounts of $^2H$-fatty acid is sufficient to measure release of $^2H$ to deuterated water.

In another variation, the labeled fatty acids may be administered orally, by gavage, intraperitoneally, intravascularly (e.g., intravenously, intraarterially), subcutaneously, or other bodily routes. In particular, the labeled fatty acids may be administered to an individual orally, optionally as part of a food or drink.

The individual being administered lipid precursors may be a mammal. In one variation, the mammal may be a rodent (rat or mouse), primate, hamster, guinea pig, dog, or pig. The mammal may be wild-type. In another embodiment, the mammal may be an engineered animal including, but not limited to, a transgenic animal, a gene knock-out animal, or a gene knock-in animal. In one embodiment, the mammal may be healthy. In another embodiment, the mammal may have a disease or medical condition. Mammals having a disease or having a medical condition may have a congenital disease or medical condition or an acquired disease or medical condition. Examples of mammals having either a congenital disease or medical condition or an acquired disease or medical condition are well known to those of skill in the art.

In still another embodiment, the mammal may be a human.

vii. Precursors of Glycosaminoglycans and Proteoglycans

Glycosaminoglycans and proteoglycans are a complex class of biomolecules that play important roles in the extracellular space (e.g., cartilage, ground substance, and synovial joint fluid). Molecules in these classes include, for example, the large polymers built from glycosaminoglycan disaccharides, such as hyaluronan, which is a polymer composed of up to 50,000 repeating units of hyaluronic acid (HA) disaccharide, a dimer that contains N-acetyl-glucosamine linked to glucuronic acid; chondroitin-sulfate (CS) polymers, which are built from repeating units of CS disaccharide, a dimer that contains N-acetyl-galactosamine-sulfate linked to glucuronic acid, heparan-sulfate polymers, which are built from repeating units of heparan-sulfate, a dimer of N-acetyl (or N-sulfo)-glucosamine-sulfate linked to glucuronic acid; and keratan-sulfate polymers, which are built from repeating units of keratan-sulfate disaccharide, a dimer that contains N-acetyl-glucosamine-sulfate liked to galactose. Proteoglycans contain additional proteins that are bound to a central hyaluronan polymer and other glycosaminoglycans, such as CS, that branch off of the central hyaluronan chain.

Labeled precursors of glycosaminoglycans and proteoglycans include, but are not limited to, $^2H_2O$ (incorporated into the sugar moieties, including N-acetylglucosamine, N-acetylgalactosamine, glucuronic acid, the various sulfates of N-acetylglucosamine and N-acetylgalactosamine, galactose, iduronic acid, and others), $^{13}C$- or $^2H$-glucose (incorporated into said sugar moieties), $^2H$- or $^{13}C$-fructose (incorporated into said sugar moieties), $^2H$- or $^{13}C$-galactose (incorporated into said sugar moieties), $^{15}N$-glycine, other $^{15}N$-labeled amino acids, or $^{15}N$-urea (incorporated into the nitrogen-moiety of said amino sugars, such as N-acetylglycosamine, N-acetyl-galactosamine, etc.); $^{13}C$- or $^2H$-fatty acids, $^{13}C$- or $^2H$-ketone bodies, $^{13}C$-glucose, $^{13}C$-fructose, $^{18}O_2$ (e.g., administered as $H_2^{18}O$), $^{13}C$- or $^2H$-acetate (incorporated into the acetyl moiety of N-acetyl-sugars, such as N-acetyl-glucosamine or N-acetyl-galactosamine), and $^{18}O$ or $^{35}S$-labeled sulfate (incorporated into the sulfate moiety of chondroitin-sulfate, heparan-sulfate, keratan-sulfate, and other sulfate moieties). All isotope labeled precursors may be purchased commercially, for example, from Cambridge Isotope Labs (Andover, Mass.), The labeled glycosaminoglycan or proteoglycan precursors may be administered orally, by gavage, intraperitoneally, intravascularly (e.g., intravenously, intraarterially), subcutaneously, or other bodily routes. In particular, the labeled glycosaminoglycan or proteoglycan precursors may be administered to an individual orally, optionally as part of a food or drink.

The individual being administered glycosaminoglycan or proteoglycan precursors may be a mammal. In one variation, the mammal may be a rodent (rat or mouse), primate, hamster, guinea pig, dog, or pig. The mammal may be wild-type. In another embodiment, the mammal may be an engineered animal including, but not limited to, a transgenic animal, a gene knock-out animal, or a gene knock-in animal. In one embodiment, the mammal may be healthy. In another embodiment, the mammal may have a disease or medical condition. Mammals having a disease or having a medical condition may have a congenital disease or medical condition or an acquired disease or medical condition. Examples of mammals having either a congenital disease or medical condition or an acquired disease or medical condition are well known to those of skill in the art.

In still another embodiment, the mammal may be a human.

B. Obtaining One or More Targeted Molecules of Interest

In practicing the methods of the invention, in one aspect, targeted molecules of interest are obtained from one or more cells, tissues, or organisms according to methods known in the art. The methods may be specific to a particular molecule of interest. Molecules of interest may be isolated from one or more biological samples.

A plurality of molecules of interest may be acquired from the one or more cells, tissues, or organisms. The one or more biological samples may be obtained, for example, by blood draw, urine collection, biopsy, or other methods known in the art. The one or more biological samples may be one or more biological fluids. The one or more molecules of interest also may be obtained from specific organs or tissues, such as muscle, liver, adrenal tissue, prostate tissue, endometrial tissue, blood, skin, and breast tissue. Molecules of interest may be obtained from a specific group of cells, such as tumor cells or fibroblast cells. Molecules of interest also may be obtained, and optionally partially purified or isolated, from the one or more biological samples using standard biochemical methods known in the art.

The frequency of biological sampling can vary depending on different factors. Such factors include, but are not limited to, the nature of the molecules of interest, ease and safety of sampling, synthesis and breakdown/removal rates of the molecules of interest, and the half-life of an administered compound.

The molecules of interest may also be purified partially, or optionally, isolated, by any purification method known in the art including, but not limited to, high pressure liquid chromatography (HPLC), fast performance liquid chromatography (FPLC), chemical extraction, thin layer chromatography, gas chromatography, gel electrophoresis, and/or other separation methods known to those skilled in the art.

In another embodiment, the molecules of interest may be hydrolyzed or otherwise degraded to form smaller molecules. Hydrolysis methods include any method known in the art, including, but not limited to, chemical hydrolysis (such as acid hydrolysis) and biochemical hydrolysis (such as peptidase degradation). Hydrolysis or degradation may be conducted either before or after purification and/or isolation of the one or more molecules of interest. The one or more molecules of interest also may be partially purified, or optionally, isolated, by purification methods including, but not limited to, high performance liquid chromatography (HPLC), fast performance liquid chromatography (FPLC), gas chromatography, gel electrophoresis, and/or any other methods of separating chemical and/or biochemical compounds known to those skilled in the art.

C. Analysis

Conventional technologies (static methods) used to identify biological actions of compounds measure only composition, structure, or concentrations of molecules in a cell and do so at one point in time. In contrast, the methods of the present invention allow for the measurement of molecular flux rates of one or more molecules of interest in intact metabolic pathways as described, infra.

1. Mass Spectrometry

Isotopic enrichment in one or more molecules of interest can be determined by various methods such as mass spectrometry, including but not limited to gas chromatography-mass spectrometry (GC-MS), isotope-ratio mass spectrometry, GC-isotope ratio-combustion-MS, GC-isotope ratio-pyrrolysis-MS, liquid chromatography-MS, electrospray ionization-MS, matrix assisted laser desorption-time of flight-MS, Fourier-transform-ion-cyclotron-resonance-MS, and cycloidal-MS.

Mass spectrometers convert molecules into rapidly moving gaseous ions and separate them on the basis of their mass-to-charge ratios. The distributions of isotopes or isotopologues of ions, or ion fragments, may thus be used to measure the isotopic enrichment in a plurality of molecules.

Generally, mass spectrometers include an ionization means and a mass analyzer. A number of different types of mass analyzers are known in the art. These include, but are not limited to, magnetic sector analyzers, electrospray ionization, quadrupoles, ion traps, time of flight mass analyzers, and Fourier transform analyzers.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, two or more mass analyzers may be coupled (MS/MS) first to separate precursor ions, then to separate and measure gas phase fragment ions. These instruments generate an initial series of ionic fragments of a molecule, and then generate secondary fragments of the initial ions.

Different ionization methods are known in the art. One key advance has been the development of techniques for ionization of large, non-volatile macromolecules such as proteins and polynucleotides. Techniques of this type have included electrospray ionization (ESI) and matrix assisted laser desorption (MALDI). These have allowed MS to be applied in combination with powerful sample separation introduction techniques, such as liquid chromatography and capillary zone electrophoresis.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

When GC/MS (or other mass spectrometric modalities that analyze ions of molecules, rather than small inorganic gases) is used to measure mass isotopomer abundances of molecules, hydrogen-labeled isotope incorporation from isotope-labeled water is amplified 3 to 7-fold, depending on the number of hydrogen atoms incorporated into the molecule from isotope-labeled water in vivo.

In general, in order to determine a baseline mass isotopomer frequency distribution for the molecule of interest, such a sample is taken before infusion of an isotopically-labeled precursor. Such a measurement is one means of establishing in the cell, tissue or organism, the naturally occurring frequency of mass isotopomers of the molecule of interest. When a cell, tissue or organism is part of a population of subjects having similar environmental histories, a population isotopomer frequency distribution may be used for such a background measurement. Additionally, such a baseline isotopomer frequency distribution may be estimated, using known average natural abundances of isotopes. For example, in nature, the natural abundance of $^{13}C$ present in organic carbon in 1.11%. Methods of determining such isotopomer frequency distributions are discussed below. Typically, samples of the molecule of interest are taken prior to and following administration of an isotopically labeled precursor to the subject and analyzed for isotopomer frequency as described below.

a. Measuring Relative and Absolute Mass Isotopomer Abundances

Measured mass spectral peak heights, or alternatively, the areas under the peaks, may be expressed as ratios toward the parent (zero mass isotope) isotopomer. It is appreciated that any calculation means which provide relative and absolute values for the abundances of isotopomers in a sample may be used in describing such data, for the purposes of the present invention.

2. Calculating Labeled: Unlabeled Proportion of Molecules of Interest

The proportion of labeled and unlabeled molecules of interest is then calculated. The practitioner first determines measured excess molar ratios for isolated isotopomer species of a molecule. The practitioner then compares measured internal pattern of excess ratios to the theoretical patterns. Such theoretical patterns can be calculated using the binomial or multinomial distribution relationships as described in U.S. Pat. Nos. 5,338,686, 5,910,403, and 6,010,846, which are hereby incorporated by reference in their entirety. The calculations may include Mass Isotopomer Distribution Analysis (MIDA). Variations of Mass Isotopomer Distribution Analysis (MIDA) combinatorial algorithm are discussed in a number of different sources known to one skilled in the art. The method is further discussed by Hellerstein and Neese (1999), as well as Chinkes, et al. (1996), and Kelleher and Masterson (1992), and U.S. patent application Ser. No. 10/279,399, all of which are hereby incorporated by reference in their entirety.

In addition to the above-cited references, calculation software implementing the method is publicly available from Professor Marc Hellerstein, University of California, Berkeley.

The comparison of excess molar ratios to the theoretical patterns can be carried out using a table generated for a molecule of interest, or graphically, using determined relationships. From these comparisons, a value, such as the value p, is determined, which describes the probability of mass isotopic enrichment of a subunit in a precursor subunit pool. This enrichment is then used to determine a value, such as the value $A_x^*$, which describes the enrichment of newly synthesized molecules for each mass isotopomer, to reveal the isotopomer excess ratio which would be expected to be present, if all isotopomers were newly synthesized.

Fractional abundances are then calculated. Fractional abundances of individual isotopes (for elements) or mass isotopomers (for molecules) are the fraction of the total abundance represented by that particular isotope or mass isotopomer. This is distinguished from relative abundance, wherein the most abundant species is given the value 100 and all other species are normalized relative to 100 and expressed as percent relative abundance. For a mass isotopomer $M^x$, $$\text{Fractional abundance of } M_X = A_X = \frac{\text{Abundance } M_x}{\sum_{i=0}^{n} \text{Abundance } M_i},$$

where 0 to n is the range of nominal masses relative to the lowest mass (Mu) mass isotopomer in which abundances occur.

$$\Delta \text{ Fractional abundance (enrichment or depletion)} =$$

$$(A_x)_e - (A_x)_b = \left(\frac{\text{Abundance } M_x}{\sum_{i=0}^{n} \text{Abundance } M_i}\right)_e - \left(\frac{\text{Abundance } M_x}{\sum_{i=0}^{n} \text{Abundance } M_i}\right)_b,$$

where subscript a refers to enriched and b refers to baseline or natural abundance.

In order to determine the fraction of polymers that were actually newly synthesized during a period of precursor administration, the measured excess molar ratio ($EM_x$) is compared to the calculated enrichment value, $A_x^*$, which describes the enrichment of newly synthesized biopolymers for each mass isotopomer, to reveal the isotopomer excess ratio which would be expected to be present, if all isotopomers were newly synthesized.

3. Calculating Molecular Flux Rates

The method of determining rate of synthesis includes calculating the proportion of mass isotopically-labeled subunit present in the molecular precursor pool, and using this proportion to calculate an expected frequency of a molecule of interest containing at least one mass isotopically-labeled subunit. This expected frequency is then compared to the actual, experimentally determined isotopomer frequency of the molecule of interest. From these values, the proportion of the molecule of interest which is synthesized from added isotopically-labeled precursors during a selected incorporation period can be determined. Thus, the rate of synthesis during such a time period is also determined.

A precursor-product relationship then may be applied. For the continuous labeling method, the isotopic enrichment is compared to asymptotic (i.e., maximal possible) enrichment and kinetic parameters (e.g., synthesis rates) are calculated from precursor-product equations. The fractional synthesis rate ($k_s$) may be determined by applying the continuous labeling, precursor-product formula:

$$k_s = [-\ln(1-f)]/t,$$

where f=fractional synthesis=product enrichment/asymptotic precursor/enrichment
and t=time of label administration of contacting in the living system studied.

For the discontinuous labeling method, the rate of decline in isotope enrichment is calculated and the kinetic parameters of the one or more molecules of interest are calculated from exponential decay equations. In practicing the method, biopolymers are enriched in mass isotopomers, preferably containing multiple mass isotopically-labeled precursors. These higher mass isotopomers of the molecules of interest, e.g., molecules containing 3 or 4 mass isotopically labeled precursors, are formed in negligible amounts in the absence of exogenous precursor, due to the relatively low abundance of natural mass isotopically-labeled precursor, but are formed in significant amounts during the period of molecular precursor incorporation. The one or more molecules of interest taken from the one or more cells, tissues, or organisms at the sequential time points are analyzed by mass spectrometry, to determine the relative frequencies of a high mass isotopomer. Since the high mass isotopomer is synthesized almost exclusively before the first time point, its decay between the two time points provides a direct measure of the rate of decay of the molecule of interest.

The first time point may be 2-3 hours after administration of precursor has ceased, depending on mode of administration, to ensure that the proportion of mass isotopically-labeled subunit has decayed substantially from its highest level following precursor administration. In one embodiment, the following time points are typically 1-4 hours after the first time point, but this timing will depend upon the replacement rate of the biopolymer pool.

The rate of decay of the molecule of interest is determined from the decay curve for the three-isotope molecule of interest. In the present case, where the decay curve is defined by several time points, the decay kinetic can be determined by fitting the curve to an exponential decay curve, and from this, determining a decay constant.

Breakdown rate constants ($k_d$) may be calculated based on an exponential or other kinetic decay curve:

$$k_d = [-\ln f]/t.$$

As described, the method can be used to determine subunit pool composition and rates of synthesis and decay for substantially any biopolymer which is formed from two or more identical subunits which can be mass isotopically labeled. Other well-known calculation techniques and experimental labeling or de-labeling approaches can be used (e.g., see Wolfe, R. R. Radioactive and Stable Isotope Tracers in Biomedicine: Principles and Practice of Kinetic Analysis. John Wiley & Sons; (March 1992)) for calculation flux rates of molecules and flux rates through metabolic pathways of interest.

4. Liquid Scintillation Counting

Radioactive isotopes may be observed using a liquid scintillation counter. Radioactive isotopes such as $^3H$ emit radiation that is detected by a liquid scintillation detector. The detector converts the radiation into an electrical signal, which is amplified. Accordingly, the number of radioactive isotopes in a biological molecule may be measured.

In one embodiment, the radioisotope-enrichment value in a biological sample may be measured directly by liquid scintillation. In a further embodiment, the radio-isotope is $^3H$.

In another embodiment, the biological molecules or components thereof may be partially purified, or optionally isolated, and subsequently measured by liquid scintillation counting.

D. Uses of the Present Invention

The disclosed invention allows for systematic, high-throughput screening of compounds or combinations of compounds or mixtures of compounds for unexpected, unintended therapeutic actions of drugs and unexpected drug toxicities. FIG. 1 depicts the contemporary and traditional method of drug screening and drug development for intended actions in contrast to the true importance of the full spectrum of unintended or unanticipated events in therapeutics and drug toxicity. FIG. 2 diagrams the high-throughput screening method for detecting new therapeutic indications elicited by known drug agents.

As these new indications have not been explicitly established previously and are not clearly predictable from pre-existing information, they are by definition unanticipated and unintended within context of the known drug's approved uses. The invention includes methods that use isotope kinetic techniques to measure the flux rates through metabolic pathways relevant to disease. The discovery tools disclosed herein also allow vertical integration throughout the DDDA process—from preclinical testing through testing in human trials, which is distinct from current methods described in the art. The compound tested (or combinations of compounds or mixtures of compounds tested) can be already FDA-approved drugs, thereby allowing discovery of new therapeutic indications and claims for approved agents (see FIG. 2 and Table 4), or the compound tested (or combinations of compounds or mixtures of compounds tested) can be any chemical entity or biological factor lacking FDA approval.

The current state of the art in pharmaceutical research and development, i.e., rational drug design coupled with target validation, allows for a more systematic approach to drug discovery than the earlier approach, used in the 1930's-1970's, of random screening of natural or synthetic chemical entities against crude physiologic models of disease. However, as can be seen in Table 1, rational drug design coupled with target validation shares critical drawbacks with the earlier approach, notably a failure to detect unintended or unanticipated events such as secondary therapeutic indications and/or toxic effects of compounds. This is because the contemporary DDDA approach is focused on narrowly targeted criteria (such as HTS assays of enzyme targets or computer modeling of enzyme active sites), and compounds such as already-approved drug agents or new chemical entities or biological factors will unavoidably have unintended or unpredictable actions on many other biologically important processes outside the scope of the narrow target of interest. The activities of compounds, both therapeutic and toxic, are not restricted to the intended targets that are screened and tested using contemporary DDDA techniques simply because pharmacologists and physicians wished it were so.

TABLE 1

Comparison of Old Drug Discovery ("Gifts from Nature") to New Drug Discovery (Rational)

|  | "Gifts from Nature" | Rational Discovery |
|---|---|---|
| Disease understood (pathogenesis)? | No | Yes |
| Physiologic/Disease Model available for rapid screening? | Yes | +/− |
| Chemical entities from Nature? | Yes | No |
| Molecular screening assay used | No | Yes |
| Proven success? | Yes | +/− |
| Chronic diseases accessible to discovery? | No | Yes |
| Unintended activities (toxic) identified? | No | No |
| Unintended activities (secondary therapeutic) identified? | No | No |
| Combination therapies (synergy, interactions) identified? | Yes | No |

The methods of the present invention allow the researcher to rationally screen for unintended or unanticipated events elicited from compounds or combinations of compounds or mixtures of compounds and to do so in a high-throughput fashion. For example, the methods disclosed herein allow the study of relative molecular flux rates in hundreds or thousands of animals for periods of weeks or months. By using labeled water (e.g., $^2H_2O$) as the source of stable isotope, each animal (or human subject) drinks water containing labeled water, such as $^2H_2O$ and this continues for as long as is required by the labeling protocol. If the molecular flux rates of two or more biological molecules are determined by mass spectrometry, the method may be completely automated (autosampled, computerized data analysis and calculation of flux rates).

The methods disclosed herein enable the skilled artisan to measure the molecular flux rates of a variety of molecules of interest that comprise the important metabolic pathways found in living systems. In many instances, altered flux rates in and through metabolic pathways can be linked to certain diseases, and measuring the flux rates of the molecules comprising these pathways will provide information useful in detecting secondary therapeutic indications and/or unintended toxic effects of compounds or combinations of compounds or mixtures of compounds. Table 2 lists many of the molecules of interest comprising metabolic pathways in living systems:

TABLE 2

Some Biomolecules for Which Flux Rates (Synthesis and Breakdown Rates; Input and Removal Rates), Can Be Measured for Screening of Chemical Entities for Actions in Biological Systems

| Class | Examples |
| --- | --- |
| I) Lipids and derivatives | |
| Acylglycerides | Triglycerides |
|  | Phospholipids |
|  | Cardiolipin |
| Fatty acids | Palmitate |
|  | Arachidonic acid |
| Sterols | Cholesterol |
|  | Bile acids |
|  | Estrogen, testosterone |
|  | Glucocorticoids |
| Ceramides | Sphingomyelin |
|  | Galactocerebroside |
| II) Carbohydrates and derivatives | |
| Monosaccharides | Glucose |
|  | Galactose |
| Amino sugars | N-Acetyl-Galactosamine |
| Polysaccharides | Glycogen |
| Glycoproteins | Sialic acid |
| Glycolipids | Galactocerebrosides |
| Glycosaminoglycans | Hyaluronic acid |
|  | Chondroitin-sulfate |
|  | Heparan-sulfate |
| III) Proteins, peptides and amino acids | |
| Structural proteins | Collagen |
|  | Myosin |
| Secreted proteins | Albumin |
|  | Apolipoprotein B |
|  | Insulin |
|  | Immunoglobulins |
|  | Prostate-specific antigen |
|  | Fibrinogen |
|  | Interleukin-2 |
| Secreted or excreted peptides | N-terminal collagen telopeptides |
|  | Glutathione |
|  | Pyridinolines |
| Membrane proteins | Preadipocyte factor-1 |
|  | Histocompatibility antigens |
|  | T-cell receptors |
| Modified amino acids | Hydroxyproline |
|  | 3-Methyl-histidine |
| Intracellular proteins | Creatine |
| Enzymes | Cytochrome C oxidase |
| Transporters | Glut-4 |
| Transcription factors | PPAR-$\gamma$ |
| IV Nucleic acids | |
| Deoxyribonucleotides | Genomic DNA |
|  | Mitochondrial DNA |
|  | Viral or bacterial DNA |
| Ribonucleotides | Messenger RNA |
|  | Ribosomal RNA |

TABLE 2-continued

Some Biomolecules for Which Flux Rates (Synthesis and Breakdown Rates; Input and Removal Rates), Can Be Measured for Screening of Chemical Entities for Actions in Biological Systems

| Class | Examples |
| --- | --- |
| Free nucleosides/nucleotides | Deoxyadenosine |
|  | Deoxythymidine |
|  | Adenosine-triphosphate |
| Purine and pyrimidine bases | Cytidine |
|  | Adenine |
| Metabolic products of bases | Uric acid |
| Oligonucleotides | ALU sequences |
|  | 8-oxo-guanidine |
|  | Methyl-deoxycytosine |

The methods of the present invention allow for the high-throughput screening of compounds or combinations of compounds or mixtures of compounds for actions in biological systems, particularly for unanticipated or unintended actions, by measuring the molecular flux rates in metabolic pathways thought to be involved in diseases. In one embodiment, the molecular flux rates in the one or more metabolic pathways of interest being measured may be relevant to an underlying molecular pathogenesis, or causation of, one or more diseases. In another embodiment, the molecular flux rates in one or more metabolic pathways of interest may contribute to the initiation, progression, severity, pathology, aggressiveness, grade, activity, disability, mortality, morbidity, disease sub-classification or other underlying pathogenic or pathologic feature of the disease of interest.

In yet another embodiment, the molecular flux rates in one or more metabolic pathways of interest may contribute to the prognosis, survival, morbidity, mortality, stage, therapeutic response, symptomology, disability or other clinical factor of the disease of interest. Two or more molecular flux rates in metabolic pathways may be measured independently or concurrently.

Such metabolic pathways may include, but are not limited to, hepatocyte proliferation and destruction, renal tubular cell turnover, lymphocyte turnover, spermatocyte turnover, protein synthesis and breakdown in muscle and heart, liver collagen synthesis and breakdown, myelin synthesis and breakdown in brain or peripheral nerves, breast epithelial cell proliferation, colon epithelial cell proliferation, prostate epithelial cell proliferation, ovarian epithelial cell proliferation, endometrial cell proliferation, bronchial epithelial cell proliferation, pancreatic epithelial cell proliferation, pancreatic beta cell regeneration, keratin synthesis in skin, keratinocyte proliferation, carbohydrate metabolism (including pathways affected by insulin resistance), cholesterol metabolism and clearance (including reverse cholesterol transport), immunoglobulin synthesis, synthesis and breakdown of mitochondrial DNA, synthesis and breakdown of mitochondrial phospholipids, synthesis and breakdown of mitochondrial proteins, synthesis and breakdown of adipose lipids, and synthesis and breakdown of adipose cells.

Known animal models of disease may be used as part of the present invention. Such animal models of disease may include, but are not limited to, Alzheimer's disease, heart failure, renal disease, diabetic nephropathy, osteoporosis, hepatic fibrosis, cirrhosis, hepatocellular necrosis, pulmonary fibrosis, scleroderma, renal fibrosis, multiple sclerosis, arteriosclerosis, osteoarthritis, rheumatoid arthritis, psoriasis, skin photoaging, skin rashes, breast cancer, prostate cancer, colon cancer, pancreatic cancer, lung cancer, acquired immunodeficiency syndrome, immune defects, multiple myeloma, chronic lymphocytic leukemia, chronic myelocytic leukemia, diabetes, diabetic complications, insulin resistance, obesity, lipodystrophy, metabolic syndrome, muscle wasting, frailty, deconditioning, angiogenesis, hyperlipidemia, infertility, viral or bacterial infections, auto-immune disorders, and immune flares Table 3 contains exemplary examples of metabolic pathways and associated disease states. Although extensive, the list contained in Table 3 is not intended to be limiting, as one of skill would understand that the methods of the present invention are useful for any disease whose etiology is at least in part defined by one or more altered flux rates in one or more metabolic pathways.

TABLE 3

Examples of Metabolic Pathways that Can Be Measured (and Relevant Diseases) to Screen for Unanticipated or Unintended Actions in Biological Systems

| Metabolic Pathway | Disease |
|---|---|
| I) DNA replication (cell division) | |
| Hepatocytes | Hepatitis; hepatic necrosis |
| Lymphocytes (including antigen-specific T-cells) | AIDS; vaccination |
| Spermatocytes | Male infertility |
| Colonocytes | Colon cancer and colitis |
| Mammary epithelial cells | Breast cancer |
| Renal tubular cells | Nephrotoxins |
| Prostate epithelial cells | Prostate cancer; BPH |
| Tumor cells | Cancer, leukemia |
| Vascular smooth muscle cells | Atherosclerosis |
| Mitochondria | Metabolic fitness; mitochondrial diseases |
| Pancreatic β-cells | Type 1 diabetes |
| Bone marrow progenitor cells | Bone marrow failure |
| Keratinocytes | Psoriasis |
| Endometrial cells | Endometrial cancer |
| Endothelial cells | Angiogenesis |
| II) Fibrogenesis and bone deposition | |
| Liver collagen synthesis | Liver fibrosis; cirrhosis |
| Lung collagen synthesis | Pulmonary fibrosis |
| Cardiac collagen synthesis | Heart failure |
| Renal collagen synthesis | Renal fibrosis |
| Dermal collagen synthesis | Scleroderma |
| Bone collagen synthesis | Osteoporosis; Paget's Disease |
| Cartilage collagen synthesis | Osteoarthritis |
| III) Lipid synthesis and breakdown | |
| Adipose tissue triglycerides | Obesity; Lipodystrophy |
| Serum cholesterol | Hyperlipidemia |
| Brain myelination and demyelination | Multiple Sclerosis |
| Mitochondrial phospholipids | Metabolic fitness |
| Sterols | Gall bladder disease; dyslipidemia; hormonal disorders |
| IV) Tissue glycosaminoglycans | |
| Synovial fluid hyaluronic acid | Osteoarthritis; rheumatoid arthritis |
| Synovial fluid chondroitin-sulfate | Osteoarthritis; rheumatoid arthritis |
| Cartilage hyaluronic acid and chondroitin-sulfate | Osteoarthritis; rheumatoid arthritis |
| Tumor hyaluronic acid | Metastatic potential |
| V) Protein synthesis (general) | |
| Immunoglobulins | Multiple myeloma; vaccination |
| Albumin | Malnutrition |
| Apolipoprotein B or E | Hyperlipidemia |
| Muscle myosin | Frailty |
| Skin keratin | Psoriasis |
| Amyloid-β | Alzheimer's disease |
| Viral or bacterial proteins | Infectious diseases |
| Insulin | Diabetes mellitus |
| Interleukins and cytokines | Inflammation |
| Hair proteins | Hirsutism; baldness |
| Histocompatibility proteins | Transplantation |

TABLE 3-continued

Examples of Metabolic Pathways that Can Be Measured (and Relevant Diseases) to Screen for Unanticipated or Unintended Actions in Biological Systems

| Metabolic Pathway | Disease |
|---|---|
| Hemoglobin | Anemias |
| Histones | Gene regulation |
| Fibrinogen | Clotting disorders |
| VI) Carbohydrate synthesis | |
| Blood glucose | Diabetes mellitus |
| Galacto-cerebrosides | Multiple Sclerosis |
| Advanced glycosylation products | Diabetic complications |
| Tissue glycogen | Insulin resistance |

The methods of the present invention allow for the identification of secondary indications for FDA (or other corresponding agencies outside of the U.S.)-approved drugs. With regard to secondary (unintended) therapeutic actions of drugs, it should be noted that, once a drug is approved by the FDA, (or other corresponding agencies outside the U.S.) it may be prescribed by a physician for purposes other than the FDA-approved (i.e., intended and rigorously tested) indication or indications. Indeed, "off-label" use accounts for the majority (>60%) of prescriptions written in the U.S. Such off-label use often accounts for the greatest commercial and medical impact of approved drugs (Table 2, supra). Failure to recognize or be aware of such secondary (i.e., unintended or unanticipated) therapeutic actions has often prevented pharmaceutical companies from obtaining the full commercial advantage of their proprietary agents before expiration of patent protection. Therefore, new uses for approved agents represents one of the most attractive and commercially profitable approaches for developing new therapeutic agents in the United States, because approved agents have the largest human experience relative to potential toxicities, have already undergone full safety and dosing testing, and are familiar to medical providers.

Known or approved drug agents may be screened for actions on single or multiple metabolic pathways independently or concurrently. The drugs may be selected randomly or the drugs may be selected on the basis of a specific biochemical rationale or hypothesis concerning a hypothesized role in the molecular pathogenesis of one or more diseases. Non-approved drugs, such as new chemical entities, non-approved biological factors, drug leads (including biological leads), and the like also may be selected randomly or may be selected on the basis of a specific biochemical rationale or hypothesis concerning a hypothesized role in the molecular pathogenesis of one or more diseases.

Such known or approved drugs may include, but are not limited to, statins, glitazones, COX-2 inhibitors, NSAIDS, β-blockers, calcium channel blockers, ACE inhibitors, antibiotics, antiviral agents, hypolipidemic agents, antihypertensives, anti-inflammatory agents, antidepressants, anxiolytics, anti-psychotics, sedatives, analgesics, antihistamines, oral hypoglycemic agents, antispasmodics, antineoplastics, cancer chemotherapeutic agents, sex steroids, pituitary hormones, cytokines, chemokines, appetite suppressant agents, thyromimetics, anti-seizure agents, sympathomimetics, sulfa drugs, biguanides, and other classes of agents. Indeed, there are numerous examples of secondary claims or off-label uses of approved drugs in the current therapeutic armamentarium (Table 4).

TABLE 4

Examples of Secondary Indications or Off-Label Uses of Approved Drugs

Minoxidil (hair loss)
Metformin (PCO-NASH)
Quinidine (malaria patients w/A-Fib improved)
Chloroquine (malaria -> RA + SLE)
Carbonic anhydride inhibitors (sulfanilamide derivative)
Sulfonylureas (sulfa's -> hypoglycemia)
Prazosin (BPH)
Bisphosphonates
Megace (weight gain in cachexia)
β-agonists (muscle gain)
Retinoids (wrinkles)
Tegretol + Elavil (DM neuropathy)
MAO's (INH antidepressant activities)
ACE inhibitors (DM nephropathy; CHF fibrosis)
COX-2 (CLL; colon chemoprevention)
Sulfasaline (Crohn's disease)
Thalidomide (weight gain; apthous ulcers)
Statins (osteoporosis/Alzheimer's disease; multiple sclerosis)
Amiodarone (angina -> arrhythmias)
Chlorpropamide (DI)
Amantadine (Parkinson's disease)
Niacin (HLP)
Methotrexate (RA)
PTU (cirrhosis)
β-blockers/$Ca^{++}$ blockers (migraine)
Tegretol (manic-depression)
Dilantin (trigeminal neuralgia)
Diazoxide (insulinoma)

Combination therapies represent another area that the contemporary DDDA system misses entirely. Drugs may act synergistically on a disease process by acting on different steps in the disease pathway (FIG. 2). These interactions will not be observable through screening procedures that measure one targeted enzyme or gene at a time. Because drug combinations are themselves patentable and can provide an additional period of exclusivity to a pharmaceutical company, the failure to identify effective, unanticipated drug combinations represents a huge commercial loss to the industry. The methods of this invention allow combination therapies to be systematically identified by a high-throughput screening approach (Table 5).

TABLE 5

Examples of Combination Therapies

Cancer chemotherapies
Leukemia chemotherapies
HIV/AIDS (e.g., protease inhibitor/nucleoside/non-nucleoside reverse transcriptase inhibitor cocktails)
Bacterial infection (e.g., sulfonamide/trimethoprin)
Diabetes (e.g., bed-time insulin/day-time sulfonyl urea)
Anti-hypertensives (e.g., calcium-channel blockers/thiazole diuretics)
Heart disease (e.g., beta-blockers/nitrates for angina; digoxin/beta-blockers for congestive heart failure)

Agents with different sites of action in the same pathway may have complementary, synergistic, or antagonistic effects on flux rates through the pathway of interest in vivo (e.g., flux rates in de novo DNA synthesis: see FIG. 3).

These interactions between agents cannot be detected or quantified by use of contemporary or traditional assays that investigate one molecular target and step at a time in a disease-related pathway. Many examples of extremely useful combination drug therapies have emerged in medical therapeutics (see Table 5), generally by serendipitous discovery, trial-and-error in humans with a disease, or based on theoretical biochemical interactions. A method for systematically screening and evaluating combinations of agents for effects on fluxes through pathways, particularly for screening and evaluating known, approved drugs, had not previously been available. The invention disclosed herein would facilitate the process of identifying, developing and approving effective therapeutic combinations.

In another embodiment, the methods of the invention are useful in detecting toxic effects of compounds. Unanticipated toxicities of compounds often emerge in phase II-III FDA clinical trials or, even worse, during post-approval clinical use of a drug. Such toxicities are common and represent an enormous source of financial losses to the pharmaceutical industry. The failure of the DDDA system to identify most toxicities early in the DDDA process or to monitor for their occurrence prior to clinical signs and symptoms represents a basic failure of the current DDDA process that has an adverse impact on public health as well as pharmaceutical company commercial profitability. Such toxic effects (unanticipated toxicities) may include end-organ toxicity. End-organ toxicity may include, but is not limited by, hepatocyte proliferation and destruction, renal tubular cell turnover, lymphocyte turnover, spermatocyte turnover, protein synthesis and breakdown in muscle and heart, liver collagen synthesis and breakdown, myelin synthesis and breakdown in brain or peripheral nerves, breast epithelial cell proliferation, colon epithelial cell proliferation, prostate epithelial cell proliferation, ovarian epithelial cell proliferation, endometrial cell proliferation, bronchial epithelial cell proliferation, pancreatic epithelial cell proliferation, keratin synthesis in skin, keratinocyte proliferation, immunoglobulin synthesis, synthesis and breakdown of mitochondrial DNA, synthesis and breakdown of mitochondrial phospholipids, synthesis and breakdown of mitochondrial proteins, synthesis and breakdown of adipose lipids, and synthesis and breakdown of adipose cells.

E. Isotopically-Perturbed Molecules

In another variation, the methods provide for the production of isolated isotopically-perturbed molecules (e.g., labeled fatty acids, lipids, carbohydrates, proteins, nucleic acids and the like). These isolated isotopically-perturbed molecules comprise information useful in determining the flux of molecules within the metabolic pathways of interest. Once isolated from a cell and/or a tissue of an organism, one or more isolated isotopically-perturbed molecules are analyzed to extract information as described, supra.

F. Kits

The invention also provides kits for measuring and comparing molecular flux rates in vivo. The kits may include isotope-labeled precursor molecules, and may additionally include chemical compounds known in the art for separating, purifying, or isolating proteins, and/or chemicals necessary to obtain a tissue sample, automated calculation software for combinatorial analysis, and instructions for use of the kit.

Other kit components, such as tools for administration of water (e.g., measuring cup, needles, syringes, pipettes, IV tubing), may optionally be provided in the kit. Similarly, instruments for obtaining samples from the cell, tissue, or organism (e.g., specimen cups, needles, syringes, and tissue sampling devices) also may be optionally provided.

G. Information Storage Devices

The invention also provides for information storage devices such as paper reports or data storage devices comprising data collected from the methods of the present invention. An information storage device includes, but is not limited to, written reports on paper or similar tangible medium, written reports on plastic transparency sheets or microfiche, and data stored on optical or magnetic media (e.g., compact discs, digital video discs, magnetic discs, and the like), or computers storing the information whether temporarily or permanently. The data may be at least partially contained within a computer and may be in the form of an electronic mail message or attached to an electronic mail message as a separate electronic file. The data within the information storage devices may be "raw" (i.e., collected but unanalyzed), partially analyzed, or completely analyzed. Data analysis may be by way of computer or some other automated device or may be done manually. The information storage device may be used to download the data onto a separate data storage system (e.g., computer, hand-held computer, and the like) for further analysis or for display or both. Alternatively, the data within the information storage device may be printed onto paper, plastic transparency sheets, or other similar tangible medium for further analysis or for display or both.

H. Examples

The following non-limiting examples further illustrate the invention disclosed herein and one of skill in the art will appreciate that variations in the procedures described in the Examples, supra, and read in light of what is disclosed in the specification, are fully encompassed by the invention as claimed:

Example 1

Measurement Triglyceride (TG) Synthesis (Lipogenesis) and Breakdown (Lipolysis) in Rats after Exposure to Compounds To assess whether a compound inhibits lipogenesis (and therefore, a candidate drug for treating obesity or other metabolic disorders) Sprague-Dawley rats (200-300 g Simonsen Labs, Gilroy, Calif.) are either exposed to a compound or left unexposed (i.e., controls). Rats are administered compound or vehicle via gavage. One or several compounds may be administered. For example, thousands of compounds may be initially screened, pooled, rescreened, subpooled, etc., to screen for one or more active compounds. An initial priming dose of 99.8% $^2H_2O$ is given via intraperitoneal injection to achieve ca. 2.5% body water enrichment (assuming 60% body weight as water) followed by administration of 4% $^2H_2O$ in drinking water for up to 12 weeks.

Adipose tissue samples are placed in dual glass tissue grinders (e.g., Kontes tissue grinders, Kimble Kontes, Vineland, N.J.) with 1 ml methanol:chloroform (2:1), ground until homogenous then centrifuged to remove protein. The solution is extracted with 2 ml each chloroform and water. The aqueous phase is discarded and the lipid fraction is transesterified by incubation with 3N methanolic HCL (Sigma-Aldrich) at 55° C. for 60 min. Fatty acid methyl esters are separated from glycerol by the Folch technique, with the modification that pure water rather than 5% NaCl is used for the aqueous phase. The aqueous phase containing glycerol is then lyophilized and glycerol is converted to glycerol triacetate by incubation with acetic anhydride:pyridine, 2:1 as described elsewhere (Hellerstein, M. K., R. A. Neese, and J. M. Schwarz. Am J Physiol 265:E814-20, 1993, herein incorporated by reference). Some samples are extracted and then TG separated from other acylglycerides by thin layer chromatography (TLC) as described elsewhere (Jung, H. R., S. M. Turner, R. A. Neese, S. G. Young, and M. K. Hellerstein. Biochem J 343 Pt 2:473-8, 1999, herein incorporated by reference), then analyzed as described, supra.

Glycerol-triacetate is analyzed for isotope enrichment by GC/MS, as described, supra.

The fraction of TG that is newly synthesized, (f) is calculated as described, supra.

The theoretical plateau or asymptotic value ($A_1^\infty$) in TG-glycerol during $^2H_2O$ labeling is determined in two ways: by mass isotopomer distribution analysis (MIDA) of the combinatorial labeling pattern in glycerol ($A_{1\ mida}^\infty$) and by measurement of plateau enrichments reached in "fully replaced" TG depots ($A_1^\infty$ plateau) (see below). The standard precursor-product equation is then applied:

$$f = 1 - e^{-ks*t}$$

$$ks = -\ln(1-f)/t$$

Where ks represents the fractional replacement or synthesis rate constant and t is time of labeling.

The absolute synthesis rate of adipose TG is calculated by multiplying the measured fractional synthesis (ks) over the period of labeling times the pool size of TG. For the purpose of this calculation, TG content is assumed to be 10% of body weight in non-obese young rodents. The absolute synthesis rate of adipose tissue TG can be calculated as follows, $$\text{Absolute synthesis (mg/d)} = ks(d-1) \times TG \text{ content (mg)}$$

For statistical analysis, ANOVA is used to compare groups with p<0.05 as the criteria for significance. Curve fitting of label incorporation data is performed using Delta Graph (Delta Point, Inc.).

TG synthesis rates are then compared between exposed animals and unexposed animals to determine whether a compound (or combination of compounds or mixture of compounds) inhibits lipogenesis One can also assess whether a compound (or combination of compounds or mixture of compounds) stimulates lipolysis using the same protocols as described above. The net lipolytic (TG breakdown) rate in individual fat depots is calculated from the difference between the absolute rate of TG synthesis and the net rate of TG accumulation, where the latter is determined from the change in weight over time in a fat pad or in the whole body:

$$\text{Net lipolysis (mg/d)} = \text{Absolute } TG \text{ synthesis} - \text{net } TG \text{ accumulation} = ([ks(d-1) \times TG \text{ content (mg)}]) - [(\text{change in } TG \text{ content})/\text{time }(d)]$$

Compound-exposed animals are then compared to unexposed animals to determine if the compound (or combination of compounds or mixture of compounds) has lipolytic activity.

Example 2

Measurement of DNA Synthesis and Breakdown in Rats after Exposure to Compounds

DNA synthesis is a biomarker for cell proliferation. In some settings it may be desirable to stimulate cell proliferation (e.g., to stimulate wound healing) while in other settings it may be desirable to inhibit cell proliferation (e.g., cancer).

Rats are administered $^2H_2O$ as discussed in Example 1, supra.

Rats are either administered compounds (or combinations of compounds or mixtures of compounds) or vehicle (controls) as discussed in Example 1, supra.

DNA is then isolated from the tissue or cell of interest using a Qiagen kit (Qiagen, Valencia, Calif.), following the manufacturer's protocol.

Isotope enrichment is then analyzed and flux rates calculated as described, supra. DNA synthesis is then determined as described, supra, (and in U.S. Pat. No. 5,910,403, incorporated by reference). Compound-exposed animals are then compared to unexposed animals to determine if the compound (or combination of compounds or mixture of compounds) has an effect on DNA synthesis.

Example 3

Measurement of Neurogenesis in Rat Hippocampal Neuroprogenitor Cells after Exposure to Compounds Compounds (or combinations of compounds or mixtures of compounds) are tested on rats to determine whether one or more may have effects on neurogenesis. Compounds with neurogenic potential may find use in treating spinal cord injury, Parkinson's disease, Huntington's disease and other neurodegenerative disorders. Rats are divided into exposed and control groups and administered labeled water as in Example 1, supra. After exposure to compound or combinations of compounds or mixtures of compounds (or vehicle if control rat), by gavage, intrathecal, or intracranial administration (route of administration is dependent on the chemistry of the compound or combination of compounds or mixture of compounds, as is well known in the art) rats are deeply anesthetized with a mixture of ketamine, xylazine, and acepromazine. Rats are then decapitated and whole brains are removed.

For isolating tissue for neurogenesis analysis, the brain is bisected longitudinally and each hippocampal lobe is separated from the overlaying cortical white matter using the natural separation line along the alveus hippocampus. The white matter of the fimbria and subiculumis removed.

Tissues are finely minced and digested for 45 min in a solution of papain (2.5 U/ml; Worthington, Freehold, N.J.), DNase (250 U/ml, Worthington), and neutral protease (1 U/ml Dispase; Boehringer Mannheim, Indianapolis, Ind.) dissolved in HBSS. (Alternatively, tissue can also be digested for 45 min in DMEM containing a mixture of 0.1% papain and 0.01% DNase).

Cells and tissue fragments are washed three times with DMEM containing 10% FBS (Hyclone, Logan, Utah).

Whole digested tissue is then suspended in DMEM-10% FBS, filtered through a sterile 107 μM nylon mesh and thoroughly mixed with an equal volume of Percoll solution. The Percoll solution is made by mixing nine parts of Percoll (Amersham Pharmacia Biotech, Uppsala, Sweden) with one part 10×PBS (Irvine Scientific, Santa Ana, Calif.).

The cell suspension is then fractionated by centrifugation for 30 min, 18° C., at 20,000×g. Cell fractions are harvested and washed free of Percoll by three or more rinses in DMEM-10% FBS.

DNA synthesis is measured as in Example 2, supra.

Compound-exposed animals are then compared to unexposed animals to determine if the compound (or combination of compounds or mixture of compounds) has an effect on DNA synthesis in hippocampal neuroprogenitor cells.

Example 4

Measurement of Flux Rates of Alzheimer Disease-Related Proteins from Mice after Exposure to Compounds Mice are labeled with $^2H_2O$ using the procedures described in Example 1, supra, for rats. Mice are given compound via gavage, intrathecal, or intracranial administration. Urine is collected to isolate amyloid beta (Aβ) protein. Total urinary protein is concentrated and exchanged in a suitable buffer for immunoaffinity purification. After immunoaffinity purification, Aβ can be further purified using size exclusion and/or reversed phase chromatography. The identity of purified peptides is confirmed by ELISA, western blot, and LC-MS (ESI).

Mice are sacrificed and brain tissue is extracted and amyloid precursor protein (APP) and C-terminal fragment of APP (CTF) are obtained. Brain proteins are extracted in neutral buffer, insoluble material is removed, and proteins precipitated. Resulting material is exchanged into an ion exchange buffer, and purified by ion exchange chromatography and then size exclusion and/or reversed phase chromatography. The identity of purified protein is confirmed by ELISA and western blot.

Enrichments for Aβ, APP, and CTF are performed as described, supra. Molecular flux rates for Aβ, APP, and CTF are calculated as described, supra. Compound-exposed animals are then compared to unexposed animals to determine if the compound (or combination of compounds or mixture of compounds) has an effect on Aβ, APP, and CTF synthesis or degradation.

Example 5

Glycolytic Disposal of Glucose in Normal Rats after Exposure to Compounds

Glycolytic disposal is a biomarker for insulin resistance and type II diabetes (see Reaven G M. Banting Lecture 1988. Role of insulin resistance in human disease. *Diabetes* 37(12): 1595-607, 1988). Rats, as in Example 1, supra, are used to measure glycolytic disposal in vivo in response to compounds (or combinations of compounds or mixtures of compounds).

The $^2H$-glucose labeling protocol consists of an initial intraperitoneal (ip) injection of 99.9% [6,6-$^2H_2$] glucose. For labeling rats, 2 mg labeled glucose per gram body weight is introduced. Body water is collected as serum at various timepoints. Compounds (or combinations of compounds or mixtures of compounds) are administered by gavage.

Glycolysis is measured by measuring deuterium in body water as a percent of administered [6,6-$^2H_2$] glucose normalized to account for different molar quantities of deuterium in molecular glucose and molecular water. Deuterated water is measured as described, supra. Glycolysis from drug-exposed rats is compared with glycolysis from unexposed rats to determine if any compound (or combination of compounds or mixture of compounds) had an effect on glycolysis.

Example 6

Brain Galactocerebroside Turnover as a Measurement of Remyelination after Exposure of Compounds Rats are given deuterated water as in Example 1, supra. Rats are administered compounds (i.e., compounds not approved for inhibition of demyelination and/or stimulation of remyelination) via gavage, intrathecal, or intracranial administration. Demyelination is an important biomarker for multiple sclerosis (MS). Remyelination may indicate a potential drug candidate for treating MS.

Weigh a set of 2-mL microcentrifuge tubes. Brains are collected from rat carcasses and put it into the pre-weighed microcentrifuge tubes. The microcentrifuge tubes are weighed again. The net weight is the brain weight. The brain is put onto an ice-cooled glass plate, and 10 crystals of BHT are added. A razor blade is used to mince the brain for 1 minute. A spatula is used to put the minced brain back into the microcentrifuge tubes. The brain is minced well with a spatula. 80-120 mg of minced brain is put into 13×100 mm glass tubes with PTFE screw caps ensuring the tissue is at the bottom of the tube. The rest of the brain is stored in the microcentrifuge tubes at −20° C. 2 mL of chloroform-methanol 2:1 (v/v) with BHT is added into the glass tubes and the tubes are vortexed ensuring that all of the tissues are soaked in the solvent. Stand 3 h at room temperature in a dark area. The caps are taken off the glass tubes. The tubes are centrifuged at 2000 RCF for 10 minutes at room temperature. The supernatant (lipid extracts) is poured into 2-mL screw capped vials and the solid residue is discarded.

100 mL of developing solvent (chloroform-methanol-water: 69.15%:26.60%:4.26%) is added into the TLC separation tanks 1 h before adding the TLC plates. A 20 mL pipette is used to spot 20 mL of total cerebroside standard on lanes 1, 10, 19 of Whatman LK6DF silica gel 60 TLC plates. For each sample, a 20 mL pipette is used to spot 100 μL of lipid extracts on two neighboring lanes (50 mL/lane). Wait until TLC plates look visually dry. The TLC plates are developed in the developing tanks. Each tank holds two plates, facing each other. Normally it takes 40-45 minutes for the plates to be fully developed. After TLC plates develop, wait 15 minutes for the plates to dry. 20 iodine crystals are put into a tank specially used for iodine vapor. The tank is put on a heatblock set at 80° C. The dried TLC plates are put in the iodine tank to visualize the spots of lipids containing double bonds. The spots of total cerebroside standard are matched with those of samples. The TLC plate images are scanned by a computer. The silica gel is collected onto a weighing box and transferred to a 12×75 mm disposable glass tube. 1 mL of chloroform-methanol 2:1 is added with BHT and vortexed. Let stand until silica settles. The solvent is poured into a 13×100 mm screw cap tube. The solid residue is discarded. 1 mL of 3 N methanolic HCl is added into the tube and the tube is capped tightly. The tubes are put on a heatblock at 80° C. for 2 h. The tubes are then removed from the heating block and allowed to cool to room temperature. 1.5 mL H2O and 3 mL hexane are added into the tubes and the tubes are vortexed. 1.8-2 mL of the bottom layer (methyl glucose and methyl galactose) are transferred to GC vials. The GC vials are put into a fitted rotor of the Jouan 10.10 speedvac and the rotor is balanced and set at 60° C. Vacuum until the tubes are dry. 100 μL of acetic anhydride-pyridine 2:1 (v/v) is added to the GC vials and the vials are covered and allowed to stand for 1 h at room temperature. The vials are then blown down under N2 until dry. 100 μL ethyl acetate is added and the vials are vortexed. The mixture is transferred to GC inserts and the vials are capped with a cramper. The samples are run on the GC/MS and galactocerebroside enrichments are determined. The molecular flux rates of galactocerebroside is determined as described supra, from rats exposed to compounds (or combinations of compounds or mixtures of compounds) and unexposed (vehicle control) rats. Enrichments of galactocerebroside greater than galactocerebroside enrichments in control rats indicates increases synthesis of galactocerebroside and possible remyelination. Enrichments that are less than controls indicates demyelination.

Example 7

Unanticipated Neurogenesis after Exposure to Lipopolysaccharide (LPS)

Groups of mice (n=5/group) were given a bolus of $^2H_2O$ (Spectra Isotopes, Columbia, Md.) to 5% $^2H_2O$ in body water and were given 8% $^2H_2O$ as drinking water. Mice were maintained on $^2H_2O$ for 45 days, during which period they also received injections every other day of either lipopolysaccharide (LPS) (Sigma, St. Louis, Mo.) in saline at a dose of 1 or 4 mg/kg body weight, or no injection.

Mice were euthanized with carbon dioxide, and their brains were removed. Hippocampi were dissected out, trypsinized, and stained with tetanus toxoid (Ttx), a specific marker for neurons, and then stained with a FITC labeled anti-Ttx antibody (Roche, Basel Switzerland). Ttx and PI (DNA) positive cells were isolated on a cell sorter (Coulter EPICS Elite), and isolated cells were run through a commercially available kit (DNeasy tissue kit, Qiagen, Valencia, Calif.) to isolate their DNA. DNA was subsequently hydrolyzed, derivatized, and analyzed as described, supra.

Neurons were seen to turnover more rapidly in response to LPS in a dose dependent manner (see FIG. 4). LPS given as described is known to induce neuroinflammation in rodents. Previous work with neuroinflammatory stimuli using different, less sensitive techniques has shown a potential link between neuroinflammation and the suppression of neurogenesis. With this in mind, the Applicant had expected to observe the neurons to turn over more slowly since chronic exposure of neuroprogenitor cells to LPS would be expected to adversely effect the viability of neuroprogenitor cells and thereby decrease neurogenesis, as is well known in the art (see, e.g., Ekdahl C. T. et al. *Proc. Natl. Acad. Sci.* 2003 100(23):13632-13637, wherein neurogenesis was observed to decrease in the presence of chronic exposure to LPS). As can be seen in FIG. 5, the exact opposite was observed. In particular, the calculated fractional synthesis rate (f) of new neurons nearly doubled (from approximately 7% to nearly 14%) after exposure to LPS (see FIG. 4), when a reduction in f was the expected result. Since increases in neurogenesis are correlated with anti-depressant agents (e.g., fluoxetine), these results suggest that LPS may alleviate depression, a previously unknown indication of LPS.

Example 8

Unanticipated Decrease in Adipocyte Proliferation in ob/ob Mice after Exposure to Leptin Four week old, female, C57/bl6j mice (Jackson Labs Bar Harbor, Mich.) were studied: C57/bl6j $^{+/?}$ controls (con), ad libitum fed C57/bl6j$^{lep-/lep-}$ (ob/ob), leptin treated ob/ob (ob-lep) and food restricted ob/ob (ob-r). Mice were housed individually in hanging wire cages and fed AIN 93 purified diets (Bio Serv, Frenchtown, N.J.). Mice were given 3 days to acclimate to the environment, after which mice grew normally. All treatments and interventions began 5 days prior to the start of labeling with $^2H_2O$.

The food intake of the ob-r group was restricted and administered in a continuous manner with automatic pellet dispensers (Coulbourn Instruments, Allentown Pa.).

Ob-lep mice received murine leptin subcutaneously at a dose of 2 μg/day (Amgen, Thousand Oaks Calif.) via a 28 day Alzet mini osmotic pump (Alza Corp. Palo Alto Calif.).

Mice were injected with $^2H_2O$ (deuterated water) 0.012 ml/gm. The normal drinking water was then replaced with water enriched to 4% $^2H_2O$. $^2H_2O$ treatment had no impact on food intake or body weight. Twenty-one days following the start of $^2H_2O$ administration, mice were fasted for four hours, anesthetized with isoflurane and exsanguinated via heart puncture.

Adipose Tissue Preparation and Isolation of Adipocytes

Fat pads were isolated and dissected inguinal and retroperitoneal pads, the left and right sides were pooled for analysis.

Immediately following dissection, the fat pads were placed in HBSS with calcium in pre weighed tubes for isolation of mature adipocytes according to the method of Rodbell (Rodbell, M. Metabolism of isolated fat cells. Effects of hormones on glucose metabolism and lipolysis. *J. Biol. Chem.* 239, 375-380 (1964)). Minced tissue was placed in HBSS with 0.1% Type II collagenase (Worthington). Tissue was incubated at 37° for up to 90 minutes. Samples were spun at 800 rpm for 10 minutes. The adipose cell enriched fraction was carefully removed from the middle fraction and frozen.

DNA Isolation and Derivatization from Adipose Cells:

The frozen slurry of adipocytes was lyophilized, the dry weight of the sample was determined and then the samples were digested and DNA isolated as described elsewhere (Neese, R. A. et al. Advances in the Stable Isotope-Mass Spectrometric Measurement of DNA Synthesis and Cell Proliferation. *Anal Biochem* 298, 189-195. (2001)) using Quiagen DNeasy tissue kits. The yield of DNA from each sample was determined with a Pharmacia Biotec Genequant II spectrophotometer.

Ten to 25 µg of DNA was hydrolyzed to individual ribonucleic acids as described in detail elsewhere (Neese, R. A. et al. Advances in the Stable Isotope-Mass Spectrometric Measurement of DNA Synthesis and Cell Proliferation. *Anal Biochem* 298, 189-195. (2001)). Isolated deoxyadenosine reduced and acetylated as described previously (Neese, R. A. et al. Advances in the Stable Isotope-Mass Spectrometric Measurement of DNA Synthesis and Cell Proliferation. *Anal Biochem* 298, 189-195. (2001)). The resulting pentose-tetraacetate (PTA) derivative in ethyl acetate was injected into the GC/MS for measurement of isotope enrichments of the deoxyribose moiety of DNA.

Derivatization and Analysis of $H_2O$:

$^2H_2O$ enrichments in body water were measured in tetrabromoethylene derivatized from plasma samples as described in detail elsewhere (Neese, R. A. et al. Advances in the Stable Isotope-Mass Spectrometric Measurement of DNA Synthesis and Cell Proliferation. *Anal Biochem* 298, 189-195. (2001).

GC/MS Analyses:

Model 5970 and 5971 GC/MS or 5973 instruments (Agilent, Palo Alto, Calif.) were used for measuring isotopic enrichments of glycerol-triacetate fatty acid-methyl esters and tetrabromoethylene Tetrabromoacetylene was analyzed using a DB-225 fused silica column, monitoring m/z 265 and 266 (parent M0 and M1 masses). Standard curves of known $^2H_2O$ enrichment were run before and after each group of samples to calculate isotope enrichment.

PTA samples were analyzed for incorporation of deuterium on a HP model 5973 MS with a 6890 GC and auto-sampler (Agilent, Palo Alto, Calif.). Methane CI was used with a 30 m DB-225 column under selected ion monitoring of m/z 245-246 (representing the M0 and M1 masses). Natural abundance, (unenriched) dA samples were measured concurrently and the excess M1 (EM1) abundance in the adipose PTA samples were calculated by difference (subtraction of the M1 abundance measured in the unenriched standard from the M1 abundance in the sample). Bone marrow DNA samples were run simultaneously and used to represent a completely or near-completely turned over tissue for calculating fractional adipose cell replacement, as described previously (Neese, R. A. et al. Advances in the Stable Isotope-Mass Spectrometric Measurement of DNA Synthesis and Cell Proliferation. *Anal Biochem* 298, 189-195. (2001)).

Calculations
(see FIG. 5).

Example 9

Unanticipated Increase in Liver Cell Proliferation in Mice after Exposure to Low Dose of Griseofulvin Mice were given $^2H_2O$ (as described in Example 7, supra, except that mice were maintained on deuterated water for 5 days, the duration of the experiment) and divided into a control group (no exposure to griseofulvin), a low dose group (1% griseofulvin, the No Observable Effect Level and a dose that does not induce elevated levels of liver enzymes in plasma), a medium dose group (2% griseofulvin, a dose in which elevated levels of liver enzymes in the plasma begin to be detected), and a high dose group (5% griseofulvin, a dose that clearly elicits a toxic effect to the liver, as measured by elevated levels of liver enzymes in the plasma). Cell proliferation was measured as described, supra. Griseofulvin is recognized as a hepatotoxin, causing liver cell proliferation and porphyria. Griseofulvin was administered to mice in their chow (1% w/w) for 5 days. After 5 days of treatment, cell proliferation in exposed mice showed increased liver cell proliferation at a dose (1%) reported as a No Observable Effect Level (NOEL) (see FIG. 6). The 1% dose did not induce elevated levels of plasma liver enzymes, which is consistent with the NOEL (data not shown). The increase in liver cell proliferation at the NOEL dose (i.e., the low dose) was an unanticipated toxic response to griseofulvin since the expected result was a lack of observable toxicity based on the NOEL and reports in the literature.

Example 10

Unanticipated Decrease in Mammary Epithelial Cell Proliferation in Normal and Ovariectomized Rats after Exposure to Low Doses of Selective Estrogen Receptor Modulators Rats were maintained in the University of California Berkeley Animal Facility or the KineMed vivarium in a climate controlled environment with a 12 hour light/12 hour dark cycle. Animal care and experimental procedures were approved by the University of California, Berkeley, Animal Care and Use Committee or the KineMed's Internal Animal Care and Use Committee depending on the site of the study. Rats were maintained on standard rodent chow and water provided ad libitum. Rats were sacrificed by $CO_2$ asphxyiation or anesthetized with isoflurane prior to terminal bleed by heart puncture.

Stable Isotope Labeling.

Rats were labeled with deuterated water (heavy water, $^2H_2O$) by receiving a bolus i.p. injection of sterile 99.8% $^2H_2O$ with 0.9% NaCl to quickly bring them up to desired body water enrichment quickly followed by replacement of drinking water with an enriched with $^2H_2O$ to either 4 or 8% depending on the study. When 8% was used, injections were done with ½ the injection volume twice to avoid injecting to great a volume. The % $^2H_2O$ used for each study will be indicated in describing the study designs (below).

Selective Estrogen Receptor Modulator (SERM) Studies:

The anti-proliferative efficacy of two different SERMS was tested in intact female Sprague-Dawley rats and Sprague-Dawley rats that had been ovariectomized with or without 17 beta-estradiol replacement. Slow release pellets were purchased from Innovative Research. The levels of drugs chosen were at the very low end of what was previously reported to effect mammary gland biology and carcinogenesis (5 mg, (Weckbecker G, Tolcsvai L, Stolz B, Pollak M, and Bruns C. Somatostatin analogue octreotide enhances the antineoplastic effects of tamoxifen and ovariectomy on 7,12-dimethyl-benz(alpha)anthracene-induced rat mammary carcinomas. *Cancer Res* 54: 6334-6337, 1994)). Initially, 2.5, 5, and 10 mg tamoxifen pellets (designed to continuously release drug over 21 days) were selected in an attempt to produce a dose-response curve. Much lower doses of tamoxifen, 0.1, 0.5 and 1.0 mg were then investigated. Based on results of the tamoxifen study, raloxifene was also investigated at the lower doses (0.1-2.5 mg 21 day pellets) than reported in the literature (s.c. injection dose equivalent to ~5.9 mg 21-day pellet) (Kubatka P, Bojkova B, Kalicka K, Chamilova M, Adamekova E, Ahlers I, Ahiersova E, and Cermakova M. Preventive effects of raloxifene and melatonin in N-methyl-N-nitrosourea-induced mammary carcinogenesis in female rats. *Neoplasma* 48: 313-319, 2001).

Rats were anesthetized with isoflurane. Pellets of drugs, estradiol and/or placebo pellets were aseptically inserted s.c. above the shoulder through a small incision (<½ cm). Wound clips were used to close the incisions.

Bone Marrow Isolation:

Femoral bone marrow was flushed out with Medium 199 and collected. The cells were centrifuged at 100×g to collect the pellet.

Enzymatic Cell Dissociation of Mammary Gland:

MEC were isolated from rat tissue by enzymatic cell dissociation as previously described (Yang J, Guzman R, Richards J, Jentoft V, DeVault M R, Wellings S R, and Nandi S. Primary culture of human mammary epithelial cells embedded in collagen gels. *Journal of the National Cancer Institute* 65: 337-343, 1980). In brief, mammary tissue was enzymatically dissociated to a single cell suspension by digesting overnight at 37° C. in Medium 199 (Invitrogen, Carlsbad, Calif.) containing 0.5% collagenase type IV (Worthington Biochemical, Lakewood, N.J.) and a 1:100 dilution of antibiotic/antimycotic cocktail (Invitrogen, Carlsbad, Calif.). Mammary glands from one animal were finely sectioned before digesting in a total volume of ~50 ml. Digestate was then centrifuged at 300×g for 10 minutes, supernatant removed, and cell pellet resuspended in 2.5 ml of Medium 199 (warmed to 37° C.). To remove extracellular DNA and reduce cell clumping 100 μl/ml of DNAse I (2,000 Kunitz units/ml) (Sigma-Aldrich, St. Louis, Mo.) was added to the cells in warm medium. Cells were vortexed on highest setting for >1 minute, and cell suspension was filtered through 40 micron nylon mesh prior to MEC isolation. This step removed extracellular DNA thereby preventing contamination and clumping of cells during subsequent Percoll gradient separation or immunomagnetic bead isolation.

Isolation by Percoll Gradient Centrifugation:

Cells were resuspended in 2.5 ml of Medium 199 and layered on top of a previously prepared Percoll gradient (16 ml of Medium 199 plus 1.2 ml of 10× Hanks Balanced Salt Solution (GibcoBRL, Grand Island, N.Y.) plus 10.8 ml of Percoll centrifuged at 20,000×g for 1 hour). Centrifugation was at 800×g for 15 min to achieve cell separation. The middle layer (isolated MEC) was removed and washed once with Medium 199.

MEC Isolation by Immunomagnetic Bead Method

Cells were isolated using an immunomagnetic bead method (MACS™) per manufacturer's recommendations (Miltenyi Biotech Inc., Auburn, Calif.). In brief, cells were pelleted and rinsed twice with 1 ml of labeling buffer (0.5% bovine serum albumin and 2 mM EDTA). Cells were incubated in 100 μl of a 1:50 dilution of primary mouse anti-rat epithelial membrane antigen (EMA) antibody (University of Iowa, Developmental Studies Hybridoma Bank, clone Ha4C19, custom biotinylated by Vector Labs, Burlingame, Calif.) in labeling buffer for 30 minutes at 4° C. Cells were rinsed by adding 1 ml labeling buffer, pelleting at 300×g. For secondary labeling with streptavidin or anti-biotin magnetic beads (Miltenyi Biotech Inc., Auburn, Calif., 20 μl beads per $10^7$ cells in 80 μl labeling buffer) cells were incubated in the recommended concentration of immunomagnetic reagent in labeling buffer for 30 minutes at 4° C. Cells were rinsed using 1 ml labeling buffer, pelleted at 300×g and re-suspended in 500 μl of labeling buffer for loading onto magnetic columns (Miltenyi Biotech Inc., Auburn, Calif.). Columns were place in the magnetic holder and were preconditioned with labeling buffer, samples were loaded, rinsed 3 times with labeling buffer to elute unlabeled cells. Columns were then removed from the magnet and the positive cell fraction was plunged off column with 1 ml of labeling buffer and collected. Cells were rinsed in 1×PBS to remove excess EDTA (EDTA can interfere with DNA hydrolysis enzymes).

DNA Isolation, Hydrolysis to Nucleosides, and Derivatization for GC/MS Analysis:

The procedures for precipitation of DNA and hydrolysis to nucleosides have been described in detail previously (McCune J M, Hanley M B, Cesar D, Halvorsen R, Hoh R, Schmidt D, Wieder E, Deeks S, Siler S, Neese R, and Hellerstein M. Factors influencing T-cell turnover in HIV-1-seropositive patients [see comments]. *Journal of Clinical Investigation* 105: R1-8, 2000). In brief, cells (MEC and bone marrow cells) were lysed and DNA was isolated using Qiagen QiAmp columns. The DNA was subjected to enzymatic hydrolysis using nuclease P1 (Roche, Indianapolis, Ind.), snake venom phosphodiesterase I (Sigma, St Louis, Mo.), DNAse (Sigma, St. Louis) and alkaline phosphatase (Sigma, St Louis, Mo.) under basic conditions. Recently, a two enzyme method has been developed that considerably reduces the expense and increases the throughput. This method involves an acid hydrolysis with acid phosphatase and nuclease Si, both commercially available from a variety of sources.

Derivatization Methods:

In the initial studies in mice and hormone treated rats, the dA was converted to the aldonitriletriacetate (dRATA) derivative as previously described. The derivatization method has been previously described (Neese R A, Misell L M, Turner S, Chu A, Kim J, Cesar D, Hoh R, Antelo F, Strawford A, McCune J M, Christiansen M, and Hellerstein M K. Measurement in vivo of proliferation rates of slow turnover cells by $^2H_2O$ labeling of the deoxyribose moiety of DNA. *Proc Natl Aced Sci USA* 99: 15345-15350, 2002.). In addition, a newer more sensitive method of DNA derivitization was developed and used for subsequent studies of SERM drug treatment (Raloxifene and Tamoxifen). This pentafluorobenzyl derivative (PFBHA) was prepared by reaction of the enzymatic DNA digest with excess pentafluorobenzyl hydroxylamine under acidic conditions, followed by acetylation with acetic anhydride.

GC/MS Analysis:

An HP model 5971 or 5973 MS with 5890 GC and autosampler (Hewlett-Packard, Palo Alto, Calif.) were used. Abundances of ions at mass to charge ratio (m/z) 198, 199 were quantified for the dRATA derivative, (m/z) 245, 246 were quantified for the PTA derivative and (m/z) 435, 436 were quantified for the PFBHA derivative under selected ion recording mode for derivatized deoxyribose (Neese R A, Siler S Q, Cesar D, Antelo F, Lee D, Misell L, Patel K, Tehrani S, Shah P, and Hellerstein M K. Advances in the stable isotope-mass spectrophotometric measurement of DNA synthesis and cell proliferation. *Analytical Biochemistry* 298: 189, 2001). Background isotopic enrichment, of DNA standards ran concurrently with samples, and was subtracted from sample enrichments. EM+1 (excess M+1 over background enrichment) (m/z 199, 246 or 436) enrichments of MEC were divided by bone marrow (a fully-turned over tissue) EM+1 enrichments from the same animal to determine fractional turnover of MEC (Neese R A, Siler S Q, Cesar D, Antelo F, Lee D, Misell L, Patel K, Tehrani S, Shah P, and Hellerstein M K. Advances in the stable isotope-mass spectrophotometric measurement of DNA synthesis and cell proliferation. *Analytical Biochemistry* 298: 189, 2001).

Measurement of Body $^2H_2O$ Enrichments:

Body water enrichments were determined by GC/MS as described previously (Neese R A, Siler S Q, Cesar I D, Antelo F, Lee D, Misell L, Patel K, Tehrani S, Shah P, and Hellerstein M K. Advances in the stable isotope-mass spectrophotometric measurement of DNA synthesis and cell proliferation. *Analytical Biochemistry* 298: 189, 2001).

Calculations:

Enrichments of bone marrow have previously been shown by the inventor's lab to reach asymptotic values within 7-10 days of labeling in rodents (Neese R A, Misell L M, Turner S, Chu A, Kim H, Cesar D, Hoh R, Antelo F, Strawford A, McCune J M, Christiansen M, and Hellerstein M K. Measurement in vivo of proliferation rates of slow turnover cells by $^2H_2O$ labeling of the deoxyribose moiety of DNA. *Proc Natl Acad Sci USA* 99: 15345-15350, 2002) and can be used as an essentially completely turned-over comparison tissue in rats, to determine percent replacement of rat and mouse MEC (Neese R A, Siler S Q, Cesar D, Antelo F, Lee D, Misell L, Patel K, Tehrani S. Shah P, and Hellerstein M K. Advances in the stable isotope-mass spectrophotometric measurement of DNA synthesis and cell proliferation. *Analytical Blochemistry* 298: 189, 2001).

The proliferation and replacement rates of MEC after $^2H_2O$ labeling are calculated based on the precursor-product relationship as described, supra.

$$\text{Fraction of new cells}(f) = \frac{EM_1(MEC)}{EM_1(BM)},$$

where $EM_1$=excess abundance In the M+1 mass isotopomer of derivatized dR, and BM represents bone marrow cells.

$$\text{Fractional replacement rate constant}(k, \text{day}-1) = -\ln[l-f]\_T$$

$$\text{Half-life}(t1/2, d) = 0.693 \div k$$

SERM Treatment of Ovariectomized and Intact Rats:

Results for GC/MS analysis of the effects of SERMs on MEC proliferation rates suggest that both tamoxifen and raloxifene are efficacious anti-proliferative agents at even the lowest dose, a finding that was completely unexpected given the lack of any data to suggest that the SERMs would be active at such low doses. In fact, the literature teaches that much higher doses of SERMs are necessary to see an effect on the reduction in MEC proliferation but our data indicate the contrary as even extremely low doses have robust effects (see FIG. 7). Significant reductions of MEC proliferation were observed at all doses of tamoxifen and raloxifene when rats were treated with drug and labeled for 7 days whether in the presence or absence of estrogen (see FIG. 7).

Example 11

Unanticipated Major Contribution of Glyceroneogenesis in Adipose TG Synthesis after Exposure to Rosiglitazone Rosiglitazone has been reported to increase phosphoenolpyruvate-carboxykinase (PEPCK) expression and activity in adipocytes (Glorian, M., Duplus, E., Beale, E. G., Scott, D. K., Granner, D. K., and Forest, C. (2001) *Biochimie* 83, 933-943; Duplus, E., Benelli, C., Reis, A. F., Fouque, F., Velho, G., and Forest, C. (2003) *Biochimie* 85, 1257-1264; Tordjman, J., Khazen, W., Antoine, B., Chauvet, G., Quette, J., Fouque, F., Beale, E. G., Benelli, C., and Forest, C. (2003) *Biochimie* 85, 1213-1218) and has also been shown to increase the low levels of glycerol-kinase activity found in adipose tissue (Guan, H. P., Li, Y., Jensen, M. V., Newgard, C. B., Steppan, C. M., and Lazar, M. A. (2002) *Nat Med* 8, 1122-1128), which was thought to be the primary mechanism of adipose TG synthesis after exposure to thiazolidinediones. In contrast, based on in published in vitro data, glyceroneogenesis was thought to play a very minor role in this process. The Applicant has discovered, however, that rodents exposed to the thiazolidinedione rosiglitazone in fact have a marked increase in glyceroneogenesis and that this increase in glyceroneogenesis is the primary contributing factor in adipose triglyceride synthesis, which is contrary to the common wisdom in the art based on a significant body of in vitro data showing that glycerol kinase activity is the predominant mechanism underlying adipose TG synthesis.

Animal Studies.

Mice. Four-week-old male C57Bl/6J mice (16-18 g; Jackson Laboratories, Bar Harbor, Me.) were used. Mice were fed ad libitum a high carbohydrate, low fat (HC, 70% carbohydrate, 10% fat) diet or a low carbohydrate, high fat diet (LC, 35% carbohydrate, 45% fat) (Research Diets Inc., New Brunswick, N.J.). An additional group of mice were fed a HC diet containing rosiglitazone (6.34 mg/kcal diet), which resulted in a dose of approximately 3 mg/kg/mouse/day (Research Diets Inc., New Brunswick, N.J.). After 11 days on diet, all animals were given a priming dose of 99.8% 2H$_2$O-saline via intraperitoneal injection to achieve ~4.8% $^2H_2O$ enrichment in body water (30 µl/g mouse) followed by administration of 8% $^2H_2O$ in drinking water. Mice (n=6 per group) were sacrificed after 15 or 64 days on heavy water. Mesenteric, epidymial, retroperitoneal, and inguinal adipose tissue depots were removed, and blood and urine samples were obtained.

Rats. Sprague-Dawley rats (400-500 g, Charles River Laboratories, Wilmington, Mass.) were purchased with an indwelling carotid artery catheter in place. Rats were fed ad libitum a Purina chow diet. After an overnight fast, animals were anesthetized with isoflurane and a priming dose of 99.8% $^2H_2O$-saline was given via intraperitoneal injection, as above. After a minimum of 60 minutes, to allow for 2H2O equilibration with body water, two baseline blood samples were collected (times −30 and −15 min.). At time 0, fructose was infused intravenously (16-19 mg/kg/min for 4 hours). Blood samples were taken after 3 and 4 hours of fructose administration. Animals (n=4) were sacrificed after the 4 hour blood draw and a final blood sample was collected via cardiac puncture.

Isolation of Acylglyceride-Glycerol from Adipose Tissue:

Lipids from adipose were extracted by a modified Folch extraction (Folch, J., Lees, M., and Sloane Stanley, G. H. (1957) *J Biol Chem* 226, 497-509). The lipid fraction was transesterified by incubation with 3N methanolic HCl (Sigma-Aldrich, St. Louis, Mo.) at 55° C. for 60 min. Fatty acid methyl esters were separated from glycerol by the Folch technique. The aqueous phase containing glycerol was lyophilized, and glycerol was converted to glycerol triacetate by incubation with acetic anhydride-pyridine (2:1) as described elsewhere (Siler, S. Q., Neese, R. A., Parks, E. J., and Hellerstein, M. K. (1998) *J Lipid Res* 39, 2319-2328).

Isolation of TG-Glycerol from Plasma:

Plasma, obtained from fresh whole blood, was extracted by the Folch technique. TG was isolated by TLC as described previously (Jung, H. R., Turner, S. M., Neese, R. A., Young, S. G., and Hellerstein, M. K. (1999) *Biochem J* 343 Pt 2, 473-478). Glycerol isolation and derivatization were then performed as described, supra.

Measurements of 2H2O Enrichment in Body Water.

$^2H_2O$ enrichment in body water (from plasma or urine) was measured by one of two methods. Briefly, 15-20 μL of plasma or urine were reacted in an evacuated GC vial with calcium carbide to produce acetylene. The acetylene gas was then removed with a syringe and injected into a GC vial containing 10% bromine in carbon tetrachloride and incubated at room temperature for 2 h to produce tetrabromoethane. Excess bromine was neutralized with 25 μL of 10% cyclohexene, and the sample was suspended in ethyl acetate (Collins, M. L., Eng, S., Hoh, R., and Hellerstein, M. K. (2003) *J Appl Physiol* 94, 2203-2211). Alternatively, the acetylene gas was directly measured by a new mass spectrometric method (Previs, S. F., Hazey, J. W., Diraison, F., Beylot, M., David, F., and Brunengraber, H. (1996) *J Mass Spectrom* 31, 639-642). Briefly, 25 μl of sample was injected into a closed Exitainer vial containing calcium carbide in a dry helium atmosphere. A small amount (0.5 ml) of the acetylene gas generated from the reaction was removed and injected into another closed vial with a helium atmosphere for direct analysis. The two methods, used with standard curves, give identical results. However, the direct acetylene method is less time consuming, and thus became the preferred method during the course of this study.

GC-MS Analyses.

Glycerol-triacetate was analyzed for isotope enrichment by GC-MS as described previously (Slier, S. Q., Neese, R. A., Parks, E. 3., and Hellerstein, M. K. (1998) *J Lipid Res* 39, 2319-2328). Mass isotopomer abundances were analyzed by selected ion monitoring of mass-to-charge ratios (m/z) 159-161 (M0-M2). Tetrabromoethane was analyzed for isotope enrichment by a GC-MS method as described previously (Neese, R. A., Slier, S. Q., Cesar, D., Antelo, F., Lee, D., Misell, L., Patel, K., Tehrani, S., Shah, P., and Hellerstein, M. K. (2001) *Anal Biochem* 298, 189-195). A model 6890 GC with 5973 mass spectrometer (Agilent Technologies, Palo Alto, Calif.) fitted with a DB-225 fused silica column (J&W, Folsom, Calif.) was used in chemical ionization mode. The isotopic enrichment of acetylene (m/z 26 and 27) was measured by cycloidal mass spectrometry (Monitor Instruments, Pittsburgh, Pa.), and the percentage of body water enrichment was calculated by comparison to a standard curve prepared gravimetrically from water and $^2H_2O$.

Calculations

Body $^2H_2O$ Enrichment.

Isotope enrichments of body $^2H_2O$ were determined by comparison with standard curves using $^2H_2O$ mixed in known proportions with unlabeled water and conversion to tetrabromoethane, or more recently, acetylene. Mass spectrometric analysis was described previously (Neese, R. A., Siler, S. Q., Cesar, D., Antelo, F., Lee, D., Misell, L., Patel, K., Tehrani, S., Shah, P., and Hellerstein, M. K. (2001) *Anal Biochem* 298, 189-195).

[$^2$H]Glycerol Enrichment

Isotope enrichments of [$^2$H]glycerol derived from acylglycerides were calculated by subtraction of mass isotopomer abundances in unlabeled glycerol standards (Hellerstein, M. K., and Neese, R. A. (1999) *Am J Physiol* 276, E1146-1170). EM1 and EM2 were calculated as a fraction of the sum of mass isotopomers M0-M2, as previously described for MIDA calculations (Turner, S. M., Murphy, E. J., Neese, R. A., Antelo, F., Thomas, T., Agarwal, A., Go, C., and Hellerstein, M. K. (2003) *Am J Physiol Endocrinol Metab* 285, E790-803).

MIDA Calculations of n and $A^\infty 1$:

MIDA is a technique based on combinatorial analysis of the labeling patterns present in polymers, as described supra and in U.S. Pat. No. 5,338,586. Briefly, the EM2 to EM1 ratio (R) is one embodiment of this labeling pattern. R is dependent on two factors: the proportion (p) of labeled hydrogen atoms present in tissue water (i.e., the enrichment of $^2H_2O$ in tissue water) and the possible number of C—H bonds in glycerol that are derived from this tissue water (n). If one assumes that the 2H-isotopic enrichment (p) of hydrogen in each actively incorporated C—H of α-GP is equal to the 2H-enrichment of body water and that 2H2O enrichment is constant during the labeling period, n can be calculated from the measured p in body water and the measured R.

Using calculation algorithms based on combinatorial probabilities as previously described (Turner, S. M., Murphy, E. J., Neese, R. A., Antelo, F., Thomas, T., Agarwal, A., Go, C., and Hellerstein, M. K. (2003) *Am J Physiol Endocrinol Metab* 285, E790-803; Hellerstein, M. K., and Neese, R. A. (1999) *Am J Physiol* 276, E1146-1170), a "lookup" table can be generated, describing R over a given range of values of p for discrete values of n (n=3, n=4, n=5). By using the value of p from measured body water enrichment, the expected R at each corresponding n is compared to the measured value of R (based on the lookup table, e.g., p=4.00% yields R=0.121 for n=3, R=0.143 for n=4, R=0.166 for n=5). Because physiologic samples contain a mixture of glyc3.5 and glyc5 (see below), we treat n as a non-integral value for this modeling. A linear regression equation is then generated, reflecting the relationship between R and n at the experimentally determined p (the latter based on measured $^2H_2O$ enrichment), and the value for n is calculated from the measured R (e.g., if p=4.00%, the equation for n is n=43.86R−2.29, so for R=0.152, n=4.38).

Once n is established, one can then calculate $A^\infty 1$ or the theoretical asymptotic value for fully labeled TG-glycerol. Accurate determination of this asymptotic or plateau value is required for the determination of fractional synthesis (f) using the precursor-product or rise-to-plateau approach:

$$f = EM_1 / A^\infty_1$$

where $EM_1$ represents isotopic enrichment of the mass +1-labeled species of glycerol (i.e. the measured abundance in excess of natural abundance) and $A^\infty_1$ represents the asymptotic or plateau value possible for the isotopic enrichment of the mass +1 species of glycerol, calculated from p and a non-integer value of n.

Statistical Analyses.

One-way ANOVA with planned pair-wise comparisons was used with P <0.05 as the criterion for significance. An independent group t-test and a nonparametric Mann-Whitney test with P <0.05 as the criterion for significance was used for the fructose infusion comparison.

Results:

The experiment explored the role of glyceroneogenesis in adipose TG synthesis following PPAR-γ agonist treatment. PPAR-γ agonists, such as rosiglitazone, are insulin sensitizing agents that induce a number of actions, including stimulation of adipogenesis and increased fat storage. PPAR-γ is required for the transcription of the PEPCK gene in adipocytes and rosiglitazone has been shown to induce expression of PEPCK in adipose tissue (Duplus, E., Benelli, C., Reis, A. F., Fouque, F., Velho, G., and Forest, C. (2003) *Biochimie* 85, 1257-1264). Conversion of oxaloacetate to phosphoenolpyruvate via PEPCK is the rate-limiting step in glyceroneogenesis. Rosiglitazone has been shown to significantly increase glycerol-kinase activity in isolated adipocytes (Guam, H. P., Li, Y., Jensen, M. V., Newgard, C. B., Steppan, C. M., and Lazar, M. A. (2002) *Nat Med* 8, 1122-1128). A physiologically significant contribution to adipogenesis from increased glycerol kinase activity would result in a decrease in n, whereas an increased contribution from glyceroneogenesis should increase n. The latter was clearly observed (FIG. 8). The observed increase in n with rosiglitazone treatment provides in vivo evidence for the significance of up-regulation of glyceroneogenesis, presumably via increased PEPCK expression, relative to up-regulation of glycerol kinase. This finding was unexpected as discussed, supra.

I claim:

1. A method for high-throughput screening (HTS) of combinations or mixtures of two or more compounds for actions on molecular flux rates in one or more metabolic pathways, said method comprising:
   a) administering said two or more compounds to a living system;
   b) administering an isotope-labeled substrate to said living system for a period of time sufficient for said isotope-labeled substrate to enter into and pass through a metabolic pathway of interest and thereby enter into and label a targeted molecule or molecules of interest within said one or more metabolic pathways in said living system, wherein the isotope-labeled substrate is stable isotope-labeled water and the targeted molecule or molecules of interest is selected from the group consisting of lipids, carbohydrates, proteins, peptides, amino acids, and nucleic acids;
   c) obtaining one or more samples from said living system, wherein said one or more samples comprise one or more isotope-labeled targeted molecules of interest;
   d) measuring the isotopic content or the isotopic pattern of the isotope label of the targeted molecule or molecules of interest, or the rate of change of the isotopic content or the isotopic pattern of the isotope label of the targeted molecule or molecules of interest in the sample;
   e) calculating molecular flux rates of the targeted molecule or molecules of interest within said one or more metabolic pathways of interest;
   f) measuring the molecular flux rates in said one or more metabolic pathways of interest according to steps b) through e) in a living system not administered said two or more compounds; and
   g) comparing said molecular flux rates in said one or more metabolic pathways of interest in said living system administered said two or more compounds to said molecular flux rates in said one or more metabolic pathways in said living system not administered said two or more compounds to screen said compounds for one or more actions on said molecular flux rates.

2. The method of claim 1, wherein the molecular flux rates in said one or more metabolic pathways of interest are altered in a living system having a disease of interest relative to a living system not having a disease of interest.

3. The method of claim 2, wherein the molecular flux rates of said one or more metabolic pathways of two or more diseases are measured concurrently.

4. The method of claim 3, wherein the concurrent measurement of the molecular flux rates from said metabolic pathways of interest is achieved by use of mass spectrometry techniques.

5. The method of claim 4, wherein the isotope label used is a stable, non-radioactive isotope.

6. The method of claim 1, wherein the stable isotope-labeled water is $^2H_2O$.

7. The method of claim 1, wherein said two or more compounds comprise one or more known drug agents.

8. The method of claim 1, wherein said two or more compounds comprise one or more biological factors, wherein the one or more biological factors are isolated compounds made by a living system that are administered for screening purposes.

9. The method of claim 1, wherein said actions on molecular flux rates in one or more metabolic pathways of interest comprise a toxic effect selected from the group consisting of hepatocyte proliferation and destruction, renal tubular cell turnover, lymphocyte turnover, spermatocyte turnover, protein synthesis and breakdown in muscle and heart, liver collagen synthesis and breakdown, myelin synthesis and breakdown in brain or peripheral nerves, breast epithelial cell proliferation, colon epithelial cell proliferation, prostate epithelial cell proliferation, ovarian epithelial cell proliferation, endometrial cell proliferation, bronchial epithelial cell proliferation, pancreatic epithelial cell proliferation, keratin synthesis in skin, keratinocyte proliferation, immunoglobulin synthesis, synthesis and breakdown of mitochondrial DNA, synthesis and breakdown of mitochondrial phospholipids, synthesis and breakdown of mitochondrial proteins, synthesis and breakdown of adipose lipids, and synthesis and breakdown of adipose cells.

10. The method of claim 1, wherein one or more animal models of disease are used for evaluating said one or more actions of said two or more compounds on said molecular flux rates.

11. The method of claim 10, wherein said one or more animal models of disease are selected from a group consisting of diabetic nephropathy, diabetes, insulin resistance, lipodystrophy, angiogenesis, hyperlipidemia, heart failure, arteriosclerosis, and renal disease.

12. The method of claim 10, wherein said one or more animal model of disease are selected from a group consisting of hepatic fibrosis, cirrhosis, hepatocellular necrosis, pulmonary fibrosis, and renal fibrosis.

13. The method of claim 10, wherein said one or more animal model of disease are selected from a group consisting of psoriasis, multiple sclerosis, acquired immunodeficiency syndrome, scleroderma, skin photoaging, skin rashes, rheumatoid arthritis, Alzheimer's disease, chronic myelocytic leukemia, osteoporosis, and osteoarthritis.

14. The method of claim 10, wherein said animal model of disease is selected from a group consisting of breast cancer, prostate cancer, colon cancer, pancreatic cancer, lung cancer, multiple myeloma, and chronic lymphocytic leukemia.

* * * * *